United States Patent
Gusarova et al.

(10) Patent No.: US 10,582,702 B2
(45) Date of Patent: Mar. 10, 2020

(54) NON-HUMAN ANIMALS HAVING AN ENGINEERED ANGPTL8 GENE

(71) Applicant: REGENERON PHARMACEUTICALS, INC., Tarrytown, NY (US)

(72) Inventors: Viktoria Gusarova, Pleasantville, NY (US); Andrew J. Murphy, Croton-on-Hudson, NY (US); Jesper Gromada, Scarsdale, NY (US); Dayong Guo, Overland Park, KS (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 4 days.

(21) Appl. No.: 15/424,322

(22) Filed: Feb. 3, 2017

(65) Prior Publication Data
US 2017/0245481 A1    Aug. 31, 2017

Related U.S. Application Data

(60) Provisional application No. 62/291,446, filed on Feb. 4, 2016.

(51) Int. Cl.
| | | |
|---|---|---|
| *A01K 67/027* | (2006.01) | |
| *A61K 49/00* | (2006.01) | |
| *C07K 16/22* | (2006.01) | |
| *A61K 39/00* | (2006.01) | |

(52) U.S. Cl.
CPC ...... *A01K 67/0278* (2013.01); *A61K 49/0008* (2013.01); *C07K 16/22* (2013.01); *A01K 2207/15* (2013.01); *A01K 2217/072* (2013.01); *A01K 2217/206* (2013.01); *A01K 2227/10* (2013.01); *A01K 2227/105* (2013.01); *A01K 2267/0306* (2013.01); *A01K 2267/0375* (2013.01); *A61K 2039/505* (2013.01)

(58) Field of Classification Search
CPC ............ A01K 67/0278; A01K 2207/15; A01K 2217/072; A01K 2217/206; A01K 2227/10; A01K 2227/105; A01K 2267/0306; A61K 49/0008; A61K 2039/505; C07K 14/515; C07K 16/22
See application file for complete search history.

(56) References Cited

U.S. PATENT DOCUMENTS

| | | | | |
|---|---|---|---|---|
| 6,586,251 B2 * | 7/2003 | Economides | ...... | A01K 67/0275 435/463 |
| 2015/0106961 A1 | 4/2015 | Rojas et al. | | |
| 2015/0143558 A1 | 5/2015 | McWhirter et al. | | |
| 2015/0143559 A1 | 5/2015 | McWhirter et al. | | |

FOREIGN PATENT DOCUMENTS

| | | |
|---|---|---|
| WO | 2006/098887 A2 | 9/2006 |
| WO | 2011/020005 A1 | 2/2011 |
| WO | 2011/044050 A2 | 4/2011 |
| WO | 2012/112544 A2 | 8/2012 |
| WO | 2013/063556 A1 | 5/2013 |
| WO | 2013/192030 A1 | 12/2013 |
| WO | 2014/039782 A2 | 3/2014 |
| WO | 2015/042557 A1 | 3/2015 |
| WO | 2015/179317 A2 | 11/2015 |
| WO | 2015/196051 A1 | 12/2015 |
| WO | 2016/089692 A1 | 6/2016 |
| WO | 2016/094481 A1 | 6/2016 |
| WO | 2015/171861 A1 | 11/2016 |

OTHER PUBLICATIONS

"List of rodents". Encyclopædia Britannica. Encyclopædia Britannica Online. Encyclopædia Britannica Inc., 2018. Web. Sep. 10, 2018 <https://www.britannica.com/topic/list-of-rodents-2057092>.*
Wakchaure et al., IJETAE 5(11), 210-213, 2015.*
Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Graham et al., Genome Biology, 16:260, 2014.*
Ellenbroek, Disease Models & Mechanisms 9, 1079-1087, 2016.*
Creed et al., Movement Disorders, vol. 33, No. 5, 2018.*
Valenzuela et al., Nature Biotechnology, 21(6): 652-659, 2003.*
Fu et al., Sci. Rep. 4:5013-5013, 2014.*
Devoy A. et al., "Genomically Humanized Mice: Technologies and Promises", 13:14-20 (Jan. 2012).
Fu Z. et al., "A Lipasin/Angptl8 Monoclonal Antibody Lowers Mouse Serum Triglycerides Involving Increased Postprandial Activity of the Cardiac Lipoprotein Lipase", Scientific Reports 5(1):1-9 (Dec. 21, 2015).
Peloso G.M. et al., "Association of Low-Frequency and Rare Coding-Sequence Variants With Blood Lipids and Coronary Heart Disease in 56,000 Whites and Blacks", The American Journal of Human Genetics 94:223-232 (Feb. 6, 2014).
International Search Report and Written Opinion dated Apr. 19, 2017 received in International Application No. PCT/US2017/016487.
Anderson P., "Post-Transcriptional Control of Cytokine Production", Nature Immunology 9(4):353-359 (Apr. 2008).
Clapham K.R. et al., "A Null Mutation in ANGPTL8 Does Not Associate With Either Plasma Glucose or Type 2 Diabetes in Humans", BMC Endocrine Disorders 16:7 (2016).

(Continued)

*Primary Examiner* — Thaian N. Ton
(74) *Attorney, Agent, or Firm* — Scully, Scott, Murphy & Presser, P.C.; Eileen Woo

(57) ABSTRACT

Non-human animals, and methods and compositions for making and using the same, are provided, wherein said non-human animals comprise a humanization of an Angiopoietin-like protein 8 (ANGPTL8) gene. Said non-human animals may be described, in some embodiments, as having a genetic modification to an endogenous ANGPTL8 locus so that said non-human animals express a human ANGPTL8 polypeptide.

16 Claims, 17 Drawing Sheets

Specification includes a Sequence Listing.

(56) References Cited

OTHER PUBLICATIONS

Fu Z. et al., "Lipasin, Thermoregulated in Brown Fat, is a Novel But Atypical Member of the Angiopoietin-Like Protein Family", Biochemical and Biophysical Research Communications 430:1126-1131 (2013).
Gusarova V. et al., "ANGPTL8/Betatrophin Does Not Control Pancreatic Beta Cell Expansion", Cell 159:691-696 (Oct. 23, 2014).
Mattijssen F. et al., "Regulation of Triglyceride Metabolism by Angiopoietin-Like Proteins", Biochimica et Biophysica Acta 1821:782-789 (2012).
Quagliarini E et al., "Atypical Angiopoietin-Like Protein That Regulates ANGPTL3", PNAS 109(48):19751-19756 (Nov. 27, 2012).
Rongvaux A. et al., "Human Thrombopoietin Knockin Mice Efficiently Support Human Hematopoiesis In Vivo", PNAS 108(6):2378-2383 (Feb. 8, 2011).
Wang Y. et al., "Mice Lacking ANGPTL8 (Betatrophin) Manifest Disrupted Triglyceride Metabolism Without Impaired Glucose Homeostasis", PNAS 110(40):16109-16114 (Oct. 1, 2013).
Willinger T. et al., Improving Human Hemato-Lymphoid-System Mice by Cytokine Knock-in Gene Replacement, Trends in Immunology 32(7):321-327 (Jul. 2011).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).
Zhang R., "A Monoclonal Neutralizing Antibody Against Lipasin (Angptl8), a Novel Lipid Regulator, Reduces Serum Triglycerides in Mice by Enhancing Lipoprotein Lipase-Mediated Triglyceride Clearance", Endocrine Society's 97th Annual Meeting and Expo OR13-6, San Diego (Mar. 5-8, 2015).
Zhang R. et al., "A Dual Role of Lipasin (Betatrophin) in Lipid Metabolism and Glucose Homeostasis: Consensus and Controvery", Cardiovascular Diabetology 13:133 (2014).
Zhang R., "Lipasin, a Novel Nutritionally-Regulated Liver-Enriched Factor that Regulates Serum Triglyceride Levels", Biochemical and Biophysical Research Communications 424:786-792 (2012).
GenBank Accession No. NM_018687.6 (3 pages) (Aug. 25, 2016).
GenBank Accession No. NP_061157.3 (3 pages) (Aug. 25, 2016).
GenBank Accession No. NM_001271710.1 (2 pages) (Oct. 8, 2016).
GenBank Accession No. NM_001080940.1 (3 pages) (Nov. 11, 2015).
GenBank Accession No. NP_001258639.1 (2 pages) (Oct. 8, 2016).
GenBank Accession No. NP_001074409.1 (3 pages) (Nov. 11, 2015).

\* cited by examiner

```
hANGPTL8    MPVPALCLLWALAMVTRPASAAPMGGPELAQHEELTLLFHGTLQLGQALNGVYRTTEGRL
mAngptl8    MAVLALCLLWTLASAVRPAPVAPLGGPEPAQYEELTLLFHGALQLGQALNGVYRATEARL
rAngptl8    MVVPILCLLWALATAVRPAPVAPLGGPEPAQYEELTLLFHGALQLGQALNGVYKATEARL
engAngpt18  MPVPALCLLWALAMVTRPASAAPMGGPELAQHEELTLLFHGTLQLGQALNGVYRTTEGRL
            *  * ****:  *:**: * ** * *  **:*:******:*********::* * hANGPTL8    TKARNSLGLYGRTIELLGQEVSRGRDAAQELRASLLETQMEEDILQLQAEATAEVLGEVA
mAngptl8    TEAGHSLGLGLYDRALEFLGTEVRQGQDATQELRTSLSEIQVREDALHLRAEATARSLGEVA
rAngptl8    TEAGRNLGLFDQALEFLGREVNQGRDATRELRTSLSEIQAEEDTLHLRAEATARSLREVA
engAngpt18  TKARNSLGLYGRTIELLGQEVSRGRDAAQELRASLLETQMEEDILQLQAEATAEVLGEVA
            *:   .  :       *:  *:*: *:* ** *:*****. * *** hANGPTL8    QAQKVLRDSVQRLEVQLRSAWLGPAYREFEVLKAHADKQSHILWALTGHVQRQRREMVAQ
mAngptl8    RAQQALRDTVRRLQVQLRGAWLGQAHQEFETLKARADKQSHLLWALTGHVQRQQREMAEQ
rAngptl8    RAQHALRNSVRRLQVQLRGAWLGQAHQEFENLKDRADKQNHLLWALTGHVQRQQREMAEQ
engAngpt18  QAQKVLRDSVQRLEVQLRSAWLGPAYREFEVLKAHADKQSHILWALTGHVQRQRREMVAQ
            :: *:.*::.** *:*.  ****.*:*******:. * hANGPTL8    QHRLRQIQERLHTAALPA
mAngptl8    QQWLRQIQQRLHTAALPA
rAngptl8    QQWLRQIQQRLHMAALPA
engAngpt18  QHRLRQIQERLHTAALPA
            *: ******:*** ****
```

Figure 2

Figure 8A. *Rattus norvegicus* Angptl8 mRNA (SEQ ID NO:1, NM_001271710.1):

ATACCCCGAGACTGTCCACCATGGTTGTGCCTATTCTCTGCCTCCTATGGGC
CATAGCAACAGCAGTGCGACCTGCCCAGTGGCCCCTCTCGGTGGTCCAGA
GCCGGCCCAATATGAAGAGTTGACCCTGCTCTTTCACGGGGCCCTACAGCT
AGGTCAGGCCCTCAATGGTGTGTACAAAGCCACGGAAGCTCGCCTGACAG
AAGCTGGGCGCAACCTGGGCCTTTTGACCAAGCACTGGAATTTCTGGGAA
GAGAGGTCAATCAGGGCCGGGATGCAACACGGGAGCTTCGCACCAGCTTG
TCGGAGATTCAGGCAGAAGAGGACACTTTACACCTTCGAGCAGAAGCCACA
GCCCGATCGCTGAGGGAAGTGGCCCGGGCCCAGCATGCTCTGCGGAACAG
TGTACGGAGACTACAAGTGCAGCTGAGAGGTGCCTGGCTAGGCCAAGCCC
ACCAAGAATTTGAGAATTTAAAGGATCGAGCCGATAAGCAGAACCACCTCT
TGTGGGCTCTCACTGGCCACGTGCAGCGACAGCAGCGTGAGATGGCAGAG
CAGCAACAGTGGCTGCGGCAGATCCAGCAGAGACTCCACATGGCAGCCCT
CCCAGCCTGAGACTACCTGGATGCCACTGAGGACCAGTTGTGCTGCAGGGAAC
ACTGAATGCGCTCCACCGGGCCTATCTATGAGCAGGGCCGACAGAGCTGGCTGC
CCATCAGCTAGACTTGGCCGGTGCACCCCGCTTCCTGGCAGAGCAGAGACAGAA
GCAAGCAGGCGGGATGGAAGGCAGAAGACAGCCCCGTGGAGAAGGCTGGAGA
AGGACATGAGCTCCCTTATGCCCCACACCCCACAATAAAAAGAGGCAATCTAT
AAA

Figure 8B. *Rattus norvegicus* Angptl8 amino acid (SEQ ID NO:2, NP_001258639.1):

MVVPILCLLWAIATAVRPAPVAPLGGPEPAQYEELTLLFHGALQLGQALNGVYKAT
EARLTEAGRNLGLFDQALEFLGREVNQGRDATRELRTSLSEIQAEEDTLHLRAEATA
RSLREVARAQHALRNSVRRLQVQLRGAWLGQAHQEFENLKDRADKQNHLLWALT
GHVQRQQREMAEQQQWLRQIQQRLHMAALPA

Figure 8C. *Mus musculus* Angptl8 mRNA (SEQ ID NO: 3, NM_001080940.1):

TGTCAGCCATGGCTGTGCTTGCTCTCTGCCTCCTGTGGACCTTAGCATCAGC
AGTGCGACCCGCTCCAGTGGCCCCTCTGGGTGGTCCAGAGCCAGCTCAATA
TGAAGAGCTGACCCTGCTCTTTCACGGGGCCCTGCAGCTAGGCCAGGCCCT
CAATGGCGTGTACAGAGCCACAGAGGCTCGCCTGACAGAAGCTGGGCACA
GCCTGGGCCTCTATGACAGAGCACTGGAATTCCTGGGGACAGAAGTCAGG
CAGGGCCAGGATGCCACACAGGAGCTTCGCACCAGCCTGTCGGAGATTCA
GGTGGAAGAGGACGCTTTACACCTTCGAGCTGAAGCCACAGCCCGATCACT
GGGGGAAGTGGCCCGGGCCCAGCAGGCTCTGCGGGACACTGTACGGAGAC
TACAAGTGCAGCTGAGAGGCGCCTGGCTCGGTCAAGCCCACCAAGAATTTG
AGACCTTAAAGGCTCGAGCTGATAAGCAGAGCCACCTCTTATGGGCTCTCA
CTGGCCACGTGCAGCGACAGCAGCGGGAGATGGCAGAGCAGCAACAGTGG
CTGCGACAGATCCAGCAGAGACTCCACACAGCAGCCCTCCCAGCCTGAGAC
TACCTGGATGCCACCGAGGACCAGTTGTGCTGCAAGGAACACTGAAGCGCTCCA
CCAGGCCCATGAACAGGGCTGACAGAGCCGGCTGCCCATCAGCTGGACCTGGC
CAGTGCACCCCGCTTCCTGGCAGAGCGGAGACAGAAGCAAGCAGGCGGGATGG
AAGGCAGAAGACAGAGCCCTGTGGAGGAGGGCTGGAAAAAGACACGAGCCCC
CTTATGCCCACACACCCCACAATAAAGAGAACAGAGGCAATCTAAAAAAAAA
AAAAAAAAAAAAA

Figure 8D. *Mus musculus* Angptl8 amino acid (SEQ ID NO:4, NP_001074409.1):

MAVLALCLLWTLASAVRPAPVAPLGGPEPAQYEELTLLFHGALQLGQALNGVYRA
TEARLTEAGHSLGLYDRALEFLGTEVRQGQDATQELRTSLSEIQVEEDALHLRAEAT
ARSLGEVARAQQALRDTVRRLQVQLRGAWLGQAHQEFETLKARADKQSHLLWAL
TGHVQRQQREMAEQQQWLRQIQQRLHTAALPA

Figure 8E. *Homo sapiens* ANGPTL8 mRNA (SEQ ID NO:5, NM_018687.6):

ATACCTTAGACCCTCAGTCATGCCAGTGCCTGCTCTGTGCCTGCTCTGGGCC
CTGGCAATGGTGACCCGGCCTGCCTCAGCGGCCCCATGGGCGGCCCAGA
ACTGGCACAGCATGAGGAGCTGACCCTGCTCTTCCATGGGACCCTGCAGCT
GGGCCAGGCCCTCAACGGTGTGTACAGGACCACGGAGGGACGGCTGACAA
AGGCCAGGAACAGCCTGGGTCTCTATGGCCGCACAATAGAACTCCTGGGG
CAGGAGGTCAGCCGGGGCCGGGATGCAGCCCAGGAACTTCGGGCAAGCCT
GTTGGAGACTCAGATGGAGGAGGATATTCTGCAGCTGCAGGCAGAGGCCA
CAGCTGAGGTGCTGGGGGAGGTGGCCCAGGCACAGAAGGTGCTACGGGAC
AGCGTGCAGCGGCTAGAAGTCCAGCTGAGGAGCGCCTGGCTGGGCCCTGC
CTACCGAGAATTTGAGGTCTTAAAGGCTCACGCTGACAAGCAGAGCCACAT
CCTATGGGCCCTCACAGGCCACGTGCAGCGGCAGAGGCGGGAGATGGTGG
CACAGCAGCATCGGCTGCGACAGATCCAGGAGAGACTCCACACAGCGGCG
CTCCCAGCCTGAATCTGCCTGGATGGAACTGAGGACCAATCATGCTGCAAGGA
ACACTTCCACGCCCCGTGAGGCCCCTGTGCAGGGAGGAGCTGCCTGTTCACTGG
GATCAGCCAGGGCGCCGGGCCCCACTTCTGAGCACAGAGCAGAGACAGACGCA
GGCGGGGACAAAGGCAGAGGATGTAGCCCCATTGGGGAGGGGTGGAGGAAGG
ACATGTACCCTTTCATGCCTACACACCCTCATTAAAGCAGAGTCGTGGCATCTC
AAAAAAAAAAAAAAAAA

Figure 8F. *Homo sapiens* ANGPTL8 amino acid (SEQ ID NO:6, NP_061157.3):

MPVPALCLLWALAMVTRPASAAPMGGPELAQHEELTLLFHGTLQLGQALNGVYRT
TEGRLTKARNSLGLYGRTIELLGQEVSRGRDAAQELRASLLETQMEEDILQLQAEAT
AEVLGEVAQAQKVLRDSVQRLEVQLRSAWLGPAYREFEVLKAHADKQSHILWALT
GHVQRQRREMVAQQHRLRQIQERLHTAALPA

Figure 8G. Exemplary Engineered *Angptl8* mRNA (SEQ ID NO:7):

TGTCAGCCATG(CCAGTGCCTGCTCTGTGCCTGCTCTGGGCCCTGGCAATGG
TGACCCGGCCTGCCTCAGCGGCCCCATGGGCGGCCCAGAACTGGCACAG
CATGAGGAGCTGACCCTGCTCTTCCATGGGACCCTGCAGCTGGGCCAGGC
CCTCAACGGTGTGTACAGGACCACGGAGGGACGGCTGACAAAGGCCAGGA
ACAGCCTGGGTCTCTATGGCCGCACAATAGAACTCCTGGGGCAGGAGGTC
AGCCGGGGCCGGGATGCAGCCCAGGAACTTCGGGCAAGCCTGTTGGAGAC
TCAGATGGAGGAGGATATTCTGCAGCTGCAGGCAGAGGCCACAGCTGAGG
TGCTGGGGGAGGTGGCCCAGGCACAGAAGGTGCTACGGGACAGCGTGCAG
CGGCTAGAAGTCCAGCTGAGGAGCGCCTGGCTGGGCCCTGCCTACCGAGA
ATTTGAGGTCTTAAAGGCTCACGCTGACAAGCAGAGCCACATCCTATGGGC
CCTCACAGGCCACGTGCAGCGGCAGAGGCGGGAGATGGTGGCACAGCAGC
ATCGGCTGCGACAGATCCAGGAGAGACTCCACACAGCGGCGCTCCCAGCC
TGAATCTGCCTGGATGGAACTGAGGACCAATCATGCTGCAAGGAACACTTCCAC
GCCCCGTGAGGCCCCTGTGCAGGGAGGAGCTGCCTGTTCACTGGGATCAGCCAG
GGCGCCGGGCCCCACTTCTGAGCACAGAGCAGAGACAGACGCAGGCGGGGACA
AAGGCAGAGGATGTAGCCCCATTGGGGAGGGGTGGAGGAAGGACATGTACCCT
TTCATGCCTACACACCCCTCATTAAAGCAGAGTCGTGGCATCTCAAAAAAAAAA
AAAAAAA)

Figure 8H. Exemplary Engineered Angptl8 amino acid (SEQ ID NO:8):

MPVPALCLLWALAMVTRPASAAPMGGPELAQHEELTLLFHGTLQLGQALNGVYRT
TEGRLTKARNSLGLYGRTIELLGQEVSRGRDAAQELRASLLETQMEEDILQLQAEAT
AEVLGEVAQAQKVLRDSVQRLEVQLRSAWLGPAYREFEVLKAHADKQSHILWALT
GHVQRQRREMVAQQHRLRQIQERLHTAALPA

Figure 8I. Exemplary synthetic DNA fragment for engineering a non-human *Angptl8* gene (SEQ ID NO:9)

CCAGTGCCTGCTCTGTGCCTGCTCTGGGCCCTGGCAATGGTGACCCGGCCTGCCTCAGC
GGCCCCCATGGGCGGCCCAGAACTGGCACAGCATGAGGAGCTGACCCTGCTCTTCCATG
GGACCCTGCAGCTGGGCCAGGCCCTCAACGGTGTGTACAGGACCACGGAGGGACGGCT
GACAAAGGCCAGGAACAGCCTGGGTCTCTATGGCCGCACAATAGAACTCCTGGGGCAG
GAGGTCAGCCGGGGCCGGGATGCAGCCCAGGAACTTCGGGCAAGCCTGTTGGAGACTC
AGGTGGGCACCGTAGCTGCGACACTGTGGGGTGGCCAGGAGTCCAAAGAGGAGTTCGT
GTCTAGGGTAACCAACCATCCTGGTTTGCCCAGGACTGAAGGGATTCCTGGGATACAAG
ATTTTCAGCGATAAACTCAGGCAAGTCCTTAGGTACACAAAGATGAGTTGGACATCCTA
CTAGTGACCCACTGTTTATTAAGCAGATGGAGGAGGATATTCTGCAGCTGCAGGCAGAG
GCCACAGCTGAGGTGCTGGGGGAGGTGGCCCAGGCACAGAAGGTGCTACGGGACAGCG
TGCAGCGGCTAGAAGTCCAGCTGAGGAGCGCCTGGCTGGGCCCTGCCTACCGAGAATTT
GAGGTCTTAAAGGTAAGGAGCTCCCCCAACCCTAGTGGGCTGAGACCCTGATTTCCGGC
CAGAACTCGCTTCTGCACCTTGAGTCCCAAAGACCTCCCAGATCAGCCTCCCAGCTCTGT
GGCCTCTACCCTGCATGTCCCCAGACAAAACTCAAGTCCTTTTGTGTGCCTCAGTTTCCC
TTTTGTGTGCCTCAGTTGCAAATAAGGGCAACACCTGATATCTCACAGTAGGGCCAGGT
ACTCAATGCAGGTAAAATATTCAGCATGGGGCGGGCACACAGTTGGTGCTCAATAAATT
CTTTTTTTTTTTTTTTGAGACAGAGTCTCACTGTTGCCCAGGCTGGAGTGCAGTGGTGT
GATCTTGGCTCACTGCAACCTCCACCTCCTAGGTTCAAGTGATTCTCCTGCCTCAGCCTC
CTGAGTAGCTGGAATTACAGGTGCACCAGCTAATTTTGTATTTTTAGTAGAGATGGG
ATTTCACCATGTTGGCCAGGCTGGTCTCGAACTCCTGACCTCAAGGGATCTGCCTGCCTC
GGTTTCCCAAAGTGCTGGGATTACAGGTGTGAGCCACTACACCTGGCCAATAAATTCTT
ACTACTAGAGAAACTGGTAACATTTTGTGAGCACCCAGTAAGTACCCAGCACTGTTCTA
TGCCCTTTAATAATCCATATGATGGCCGGGCATGGTGGCTCATGCCTGTAATCCCAGCA
CTTTGGGTAGCTAAGGTGGGTGGAACACTTAAGGTCAGGAGTTCGAGACCACCCTGGCC
AACATGGTGAAACCCCGTCTCTACTAAAAATACAAAAAATTAGCTGGGCGTGGTGGCAC
ATGCCTGTAGTCCCAGCTACTCAGGAGGCTTAGGTAGGAGAATCGCTTGAACCTGGGAG
GTGGAGGTTGCAGTGAGCTGAGATCGTGTCATTGCACTCAGCCTGGGTGACAGAGAGA
GACTCAAAAAAAAAAAAAATCCATAGGATGTTCATCACCTCCCCATGAAGTGAGTCCT
ATTTTATCCCCATTTTACAGATGGGGAAACTGAGGCCAAAGAGCATTGTTGACTTGCTG
GGTCACACAGATACAATGAGGGGCTGGGCAGAGGGTCAGGGGATGGGAGGTGAGGT
GGCTGTCGGCTGAGGTTTCCATTCTGACCCCACAGGCTCACGCTGACAAGCAGAGCCA
CATCCTATGGGCCCTCACAGGCCACGTGCAGCGGCAGAGGCGGGAGATGGTGGCACAG
CAGCATCGGCTGCGACAGATCCAGGAGAGGTGAGCCTGGCAGGGGTTTGGCAGGCAGG
GCAGTTGGATGGGGGGCGCACAGGGCAGCTGGAAAGGGGCCCCCTCACCTGGGCTGAG
CCACATCTCCCTCCCAGACTCCACACAGCGGCGCTCCCAGCCTGAATCTGCCTGGATG
GAACTGAGGACCAATCATGCTGCAAGGAACACTTCCACGCCCCGTGAGGCCCCTGTGCA
GGGAGGAGCTGCCTGTTCACTGGGATCAGCCAGGGCGCCGGGCCCCACTTCTGAGCACA
GAGCAGAGACAGACGCAGGCGGGACAAAGGCAGAGGATGTAGCCCCATTGGGGAGG
GGTGGAGGAAGGACATGTACCCTTTCATGCCTACACACCCCTCATTAAAGCAGAGTCGT
GGCATCTCACCCAGGGTGTCTGTGTGTGTCCTTGGCTTAGGGAGACCCCACCCAGCATG
ATGTATGAATACCTCCCATTCAAGTGCCCA

Figure 8J. Exemplary engineered *Angptl8* allele including a selection cassette (SEQ ID NO:10)

[7182allele]CACGAAACTGTCAGCCATGCCAGTGCCTGCTCTGTGCCTGCTCTGGGCCC
TGGCAATGGTGACCCGGCCTGCCTCAGCGGCCCCATGGGCGGCCCAGAACTGGC
ACAGCATGAGGAGCTGACCCTGCTCTTCCATGGGACCCTGCAGCTGGGCCAGGCC
CTCAACGGTGTGTACAGGACCACGGAGGGACGGCTGACAAAGGCCAGGAACAGCC
TGGGTCTCTATGGCCGCACAATAGAACTCCTGGGGCAGGAGGTCAGCCGGGGCCG
GGATGCAGCCCAGGAACTTCGGGCAAGCCTGTTGGAGACTCAGGTGGGCACCGTA
GCTGCGACACTGTGGGTGGCCAGGAGTCCAAAGAGGAGTTCGTGTCTAGGGTAA
CCAACCATCCTGGTTTGCCCAGGACTGAAGGGATTCCTGGGATACAAGATTTTCAG
CGATAAACTCAGGCAAGTCCTTAGGTACACAAGATGAGTTGGACATCCTACTAGT
GACCCACTGTTTATTAAGCAGATGGAGGAGGATATTCTGCAGCTGCAGGCAGAGG
CCACAGCTGAGGTGCTGGGGGAGGTGGCCCAGGCACAGAAGGTGCTACGGGACA
GCGTGCAGCGGCTAGAAGTCCAGCTGAGGAGCGCCTGGCTGGGCCCTGCCTACCG
AGAATTTGAGGTCTTAAAGGTAAGGAGCTCCCCAACCCTAGTGGGCTGAGACCC
TGATTTCCGGCCAGAACTCGCTTCTGCACCTTGAGTCCCAAAGACCTCCCAGATCA
GCCTCCCAGCTCTGTGGCCTCTACCCTGCATGTCCCCAGACAAAACTCAAGTCCTT
TTGTGTGCCTCAGTTTCCCTTTTGTGTGCCTCAGTTGCAAATAAGGGCAACACCTG
ATATCTACAGTAGGGCCAGGTACTCAATGCAGGTAAAATATTCAGCATGGGGCG
GGCACACAGTTGGTGCTCAATAAATTCTTTTTTTTTTTTTTTGAGACAGAGTCTC
ACTGTTGCCCAGGCTGGAGTGCAGTGGTGTGATCTTGGCTCACTGCAACCTCCACC
TCCTAGGTTCAAGTGATTCTCCTGCCTCAGCCTCCTGAGTAGCTGGAATTACAGGT
GCACCAGCTAATTTTGTATTTTTAGTAGAGATGGGATTTCACCATGTTGGCCAG
GCTGGTCTCGAACTCCTGACCTCAAGGGATCTGCCTGCCTCGGTTTCCCAAAGTGC
TGGGATTACAGGTGTGAGCCACTACACCTGGCCAATAAATTCTTACTACTAGAGAA
ACTGGTAACATTTTGTGAGCACCCAGTAAGTACCCAGCACTGTTCTATGCCCTTTA
ATAATCCATATGATGGCCGGGCATGGTGGCTCATGCCTGTAATCCCAGCACTTTGG
GTAGCTAAGGTGGGTGGAACACTTAAGGTCAGGAGTTCGAGACCACCCTGGCCAA
CATGGTGAAACCCCGTCTCTACTAAAAATACAAAAAATTAGCTGGGCGTGGTGGCA
CATGCCTGTAGTCCCAGCTACTCAGGAGGCTTAGGTAGGAGAATCGCTTGAACCT
GGGAGGTGGAGGTTGCAGTGAGCTGAGATCGTGTCATTGCACTCAGCCTGGGTGA
CAGAGAGAGACTCAAAAAAAAAAAAAAATCCATAGGATGTTCATCACCTCCCCATG
AAGTGAGTCCTATTTTATCCCCATTTTACAGATGGGGAAACTGAGGCCAAAGAGCA
TTGTTGACTTGCTGGGTCACACAGATACAATGAGGGGCTGGGGCAGAGGGTCAGG
GGATGGGAGGTGAGGTGGCTGTCGGCTGAGGTTTCCATTCTGACCCCCACAGGCT
CACGCTGACAAGCAGAGCCACATCCTATGGGCCCTCACAGGCCACGTGCAGCGGC
AGAGGCGGGAGATGGTGGCACAGCAGCATCGGCTGCGACAGATCCAGGAGAGGT
GAGCCTGGCAGGGGTTTGGCAGGCAGGGCAGTTGGATGGGGGCGCACAGGGCA
GCTGGAAAGGGGCCCCCTCACCTGGGCTGAGCCACATCTCCCTCCCCAGACTCCA
CACAGCGGCGCTCCCAGCCTGAATCTGCCTGGATGGAACTGAGGACCAATCATGC
TGCAAGGAACACTTCCACGCCCCGTGAGGCCCCTGTGCAGGGAGGAGCTGCCTGT
TCACTGGGATCAGCCAGGGCGCCGGGCCCCACTTCTGAGCACAGAGCAGAGACAG Figure 8J (Continued)

ACGCAGGCGGGGACAAAGGCAGAGGATGTAGCCCCATTGGGGAGGGGTGGAGGA
AGGACATGTACCCTTTCATGCCTACACACCCCTCATTAAAGCAGAGTCGTGGCATC
TCACCCAGGGTGTCTGTGTGTGTCCTTGGCTTAGGGAGACCCCACCCAGCATGAT
GTATGAATACCTCCCATTCAAGTGCCCActcgagataacttcgtataatgtatgctatacgaagttatatgcatggcct
ccgcgccgggttttggcgcctcccgcgggcgcccccctcctcacggcgagcgctgccacgtcagacgaagggcgcagcgagcgtcctgatc
cttccgcccggacgctcaggacagcggccgctgctcataagactcggccttagaaccccagtatcagcagaaggacattttaggacgggactt
gggtgactctagggcactggttttcttccagagagcggaacaggcgaggaaaagtagtcccttctcggcgattctgcggagggatctccgtggg
gcggtgaacgccgatgattatataaggacgcgccgggtgtggcacagctagttccgtcgcagccgggattgggtcgcgggttcttgtttgtggatc
gctgtgatcgtcacttggtgagtagcgggctgctgggctggccggggcttcgtggccgccgggccgctcggtgggacggaagcgtgtggaga
gaccgccaagggctgtagtctgggtccgcgagcaaggttgccctgaactgggggttgggggggagcgcagcaaaatggcggctgttcccgagt
cttgaatggaagacgcttgtgaggcgggctgtgaggtcgttgaaacaaggtgggggggcatggtgggcggcaagaacccaaggtcttgaggcct
tcgctaatgcgggaaagctcttattcgggtgagatgggctggggcaccatctggggaccctgacgtgaagtttgtcactgactggagaactcggtt
tgtcgtctgttgcgggggcggcagttatggccggtgccgttgggcagtgcaccgtaccttttgggagcgcgcgccctcgtcgtgtcgtgacgtcac
ccgttctgttggcttataatgcagggtggggccacctgccggtaggtgtgcggtaggctttttctccgtcgcaggacgcagggttcgggcctagggt
aggctctcctgaatcgacaggcgccggacctctggtgagggagggataagtgaggcgtcagtttctttggtcggttttatgtacctatcttcttaag
tagctgaagctccggttttgaactatgcgctcggggttggcgagtgtgttttgtgaagttttttaggcaccttttgaaatgtaatcatttgggtcaatatgt
aattttcagtgttagactagtaaattgtccgctaaattctggccgttttggcttttttgttagacgtgttgacaattaatcatcggcatagtatatcggcata
gtataatacgacaaggtgaggaactaaaccatgggatcggccattgaacaagatggattgcacgcaggttctccggccgcttgggtggagaggc
tattcggctatgactgggcacaacagacaatcggctgctctgatgccgccgtgttccggctgtcagcgcaggggcgcccggttcttttgtcaaga
ccgacctgtccggtgccctgaatgaactgcaggacgaggcagcgcggctatcgtggctggccacgacgggcgttccttgcgcagctgtgctcg
acgttgtcactgaagcgggaagggactggctgctattgggcgaagtgccggggcaggatctcctgtcatctcaccttgctcctgccgagaaagta
tccatcatggctgatgcaatgcggcggctgcatacgcttgatccggctacctgcccattcgaccaccaagcgaaacatcgcatcgagcgagcac
gtactcggatggaagccggtcttgtcgatcaggatgatctggacgaagagcatcaggggctcgcgccagccgaactgttcgccaggctcaagg
cgcgcatgcccgacggcgatgatctcgtcgtgacccatggcgatgcctgcttgccgaatatcatggtggaaaatggccgcttttctggattcatcg
actgtggccggctgggtgtggcggaccgctatcaggacatagcgttggctacccgtgatattgctgaagagcttggcggcgaatgggctgaccg
cttcctcgtgctttacggtatcgccgctcccgattcgcagcgcatcgccttctatcgccttcttgacgagttcttctgagggatccgctgtaagtctg
cagaaattgatgatctattaaacaataaagatgtccactaaaatggaagttttcctgtcatactttgttaagaagggtgagaacagagtacctacatttt
gaatggaaggattggagctacgggggtggggtggggtgggattagataaatgcctgctctttactgaaggctctttactattgctttatgataatgtt
tcatagttggatatcataatttaaacaagcaaaaccaaattaagggccagctcattcctcccactcatgatctatagatctatagatctctcgtgggatc
attgttttctcttgattccactttgtggttctaagtactgtggttccaaatgtgtcagtttcatagcctgaagaacgagatcagcagcctctgttccaca
tacacttcattctcagtattgttttgccaagttctaattccatcagacctcgacctgcagcccctagcccgggcgccagtagcagcacccacgtccac
cttctgtctagtaatgtccaacacctccctcagtccaaacactgctctgcatccatgtggctcccattatacctgaagcacttgatggggcctcaatgt
tttactagagccaccccctgcaactctgagaccctctggatttgtctgtcagtgcctcactggggcgttggataatttcttaaaaggtcaagttccc
tcagcagcattctctgagcagtctgaagatgtgtgcttttcacagttcaaatccatgtggctgtttcacccacctgcctggccttgggttatctatcagg
acctagcctagaagcaggtgtgtggcacttaacacctaagctgagtgactaactgaacactcaagtggatgccatctttgtcacttcttgactgtgac
acaagcaactcctgatgccaaagccctgcccacccctctcatgcccatatttggacatggtacaggtcctcactggccatggtctgtgaggtcctg
gtcctctttgacttcataattcctagggggccactagtatctataagaggaagaggggtgctggctcccaggccacagcccacaaaattccacctgctc
acaggttggctggctcgacccaggtggtgtcccctgctctgagccagctcccggccaagccagcaccatgggtaccccaagaagaagagga
aggtgcgtaccgatttaaattccaatttactgaccgtacaccaaaatttgcctgcattaccggtcgatgcaacgagtgatgaggttcgcaagaacct
gatggacatgttcagggatcgccaggcgttttctgagcatacctggaaaatgcttctgtccgtttgccggtcgtgggcggcatggtgcaagttgaat
aaccggaaatggttcccgcagaacctgaagatgttcgcgattatcttctatatcttcaggcgcgcggtctggcagtaaaaactatccagcaacattt
gggccagctaaacatgcttcatcgtcggtccgggctgccacgaccaagtgacagcaatgctgtttcactggttatgcggcggatccgaaaagaaa
acgttgatgccggtgaacgtgcaaaacaggctctagcgttcgaacgcactgatttcgaccaggttcgttcactcatggaaaatagtgatcgctgcc

Figure 8J (Continued)

aggatatacgtaatctggcatttctggggattgcttataacaccctgttacgtatagccgaaattgccaggatcagggttaaagatatctcacgtactg
acggtgggagaatgttaatccatattggcagaacgaaaacgctggttagcaccgcaggtgtagagaaggcacttagcctgggggtaactaaact
ggtcgagcgatggatttccgtctctggtgtagctgatgatccgaataactacctgttttgccgggtcagaaaaaatggtgttgccgcgccatctgcc
accagccagctatcaactcgcgccctggaagggattttttgaagcaactcatcgattgatttacggcgctaaggtaaatataaaattttaagtgtataa
tgtgttaaactactgattctaattgtttgtgtatttaggatgactctggtcagagatacctggcctggtctggacacagtgcccgtgtcggagccgcg
cgagatatggcccgcgctggagtttcaataccggagatcatgcaagctggtggctggaccaatgtaaatattgtcatgaactatatccgtaacctgg
atagtgaaacaggggcaatggtgcgcctgctggaagatggcgattgatctagataagtaatgatcataatcagccatatcacatctgtagaggttt
acttgctttaaaaaacctcccacacctcccctgaacctgaaacataaaatgaatgcaattgttgttgttaaacctgccctagttgcggccaattccag
ctgagcgtgcctccgcaccattaccagttggtctggtgtcaaaaataataataaccgggcaggggggatctaagctctagataagtaatgatcata
atcagccatatcacatctgtagaggtttacttgctttaaaaaacctcccacacctcccctgaacctgaaacataaaatgaatgcaattgttgttgttaa
cttgtttattgcagcttataatggttacaaataaagcaatagcatcacaaatttcacaaataaagcattttttcactgcattctagttgtggtttgtccaaa
ctcatcaatgtatcttatcatgtctggaataacttcgtataatgtatgctatacgaagttatgctagtaactataacggtcctaaggtagcgagctagcG
ATGCCACCGAGGACCAGTTGTGCTGCAAGGAACACTGAAGCGCTCCACCAGGCCCATG
AACAGGGCTGACAGAG

Figure 8K. Exemplary engineered *Angptl8* allele after recombinase-mediated excision of a selection cassette (SEQ ID NO:11)

[7183allele]CACGAAACTGTCAGCCATGCCAGTGCCTGCTCTGTGCCTGCTCTGGGCCC
TGGCAATGGTGACCCGGCCTGCCTCAGCGGCCCCATGGGCGGCCCAGAACTGGC
ACAGCATGAGGAGCTGACCCTGCTCTTCCATGGGACCCTGCAGCTGGGCCAGGCC
CTCAACGGTGTGTACAGGACCACGGAGGGACGGCTGACAAAGGCCAGGAACAGCC
TGGGTCTCTATGGCCGCACAATAGAACTCCTGGGGCAGGAGGTCAGCCGGGGCCG
GGATGCAGCCCAGGAACTTCGGGCAAGCCTGTTGGAGACTCAGGTGGGCACCGTA
GCTGCGACACTGTGGGTGGCCAGGAGTCCAAAGAGGAGTTCGTGTCTAGGGTAA
CCAACCATCCTGGTTTGCCCAGGACTGAAGGGATTCCTGGGATACAAGATTTTCAG
CGATAAACTCAGGCAAGTCCTTAGGTACACAAAGATGAGTTGGACATCCTACTAGT
GACCCACTGTTTATTAAGCAGATGGAGGAGGATATTCTGCAGCTGCAGGCAGAGG
CCACAGCTGAGGTGCTGGGGAGGTGGCCCAGGCACAGAAGGTGCTACGGGACA
GCGTGCAGCGGCTAGAAGTCCAGCTGAGGAGCGCCTGGCTGGGCCCTGCCTACCG
AGAATTTGAGGTCTTAAAGGTAAGGAGCTCCCCAACCCTAGTGGGCTGAGACCC
TGATTTCCGGCCAGAACTCGCTTCTGCACCTTGAGTCCCAAAGACCTCCCAGATCA
GCCTCCCAGCTCTGTGGCCTCTACCCTGCATGTCCCCAGACAAAACTCAAGTCCTT
TTGTGTGCCTCAGTTTCCCTTTTGTGTGCCTCAGTTGCAAATAAGGGCAACACCTG
ATATCTACAGTAGGGCCAGGTACTCAATGCAGGTAAAATATTCAGCATGGGGCG
GGCACACAGTTGGTGCTCAATAAATTCTTTTTTTTTTTTTTGAGACAGAGTCTC
ACTGTTGCCCAGGCTGGAGTGCAGTGGTGTGATCTTGGCTCACTGCAACCTCCACC
TCCTAGGTTCAAGTGATTCTCCTGCCTCAGCCTCCTGAGTAGCTGGAATTACAGGT
GCACCAGCTAATTTTTGTATTTTTAGTAGAGATGGGATTTCACCATGTTGGCCAG
GCTGGTCTCGAACTCCTGACCTCAAGGGATCTGCCTGCCTCGGTTTCCCAAAGTGC
TGGGATTACAGGTGTGAGCCACTACACCTGGCCAATAAATTCTTACTACTAGAGAA
ACTGGTAACATTTTGTGAGCACCCAGTAAGTACCCAGCACTGTTCTATGCCCTTTA
ATAATCCATATGATGGCCGGGCATGGTGGCTCATGCCTGTAATCCCAGCACTTTGG
GTAGCTAAGGTGGGTGGAACACTTAAGGTCAGGAGTTCGAGACCACCCTGGCCAA
CATGGTGAAACCCCGTCTCTACTAAAAATACAAAAAATTAGCTGGGCGTGGTGGCA
CATGCCTGTAGTCCCAGCTACTCAGGAGGCTTAGGTAGGAGAATCGCTTGAACCT
GGGAGGTGGAGGTTGCAGTGAGCTGAGATCGTGTCATTGCACTCAGCCTGGGTGA
CAGAGAGAGACTCAAAAAAAAAAAAAATCCATAGGATGTTCATCACCTCCCCATG
AAGTGAGTCCTATTTTATCCCCATTTTACAGATGGGGAAACTGAGGCCAAAGAGCA
TTGTTGACTTGCTGGGTCACACAGATACAATGAGGGGCTGGGGCAGAGGGTCAGG
GGATGGGAGGTGAGGTGGCTGTCGGCTGAGGTTTCCATTCTGACCCCACAGGCT
CACGCTGACAAGCAGAGCCACATCCTATGGGCCCTCACAGGCCACGTGCAGCGGC
AGAGGCGGGAGATGGTGGCACAGCAGCATCGGCTGCGACAGATCCAGGAGAGGT
GAGCCTGGCAGGGGTTTGGCAGGCAGGGCAGTTGGATGGGGGGCGCACAGGGCA
GCTGGAAAGGGGCCCCCTCACCTGGGCTGAGCCACATCTCCCTCCCCAGACTCCA
CACAGCGGCGCTCCCAGCCTGAATCTGCCTGGATGGAACTGAGGACCAATCATGC
TGCAAGGAACACTTCCACGCCCGTGAGGCCCTGTGCAGGGAGGAGCTGCCTGT
TCACTGGGATCAGCCAGGGCGCCGGGCCCACTTCTGAGCACAGAGCAGAGACAG
ACGCAGGCGGGGACAAAGGCAGAGGATGTAGCCCCATTGGGGAGGGGTGGAGGA
AGGACATGTACCCTTTCATGCCTACACACCCCTCATTAAAGCAGAGTCGTGGCATC
TCACCCAGGGTGTCTGTGTGTGTCCTTGGCTTAGGGAGACCCCACCCAGCATGAT
GTATGAATACCTCCCATTCAAGTGCCCActcgagataacttcgtataatgtatgctatacgaagttatgctagtaacta
taacggtcctaaggtagcgagctagcGATGCCACCGAGGACCAGTTGTGCTGCAAGGAACACTGAAGC
GCTCCACCAGGCCCATGAACAGGGCTGACAGAG

Figure 9A.

(AAGGCAGCCG CAGCGGCCCG GGAACCACAC CCACGAAACT GTCAGCCATG)
CCAGTGCCTG CTCTGTGCCT GCTCTGGGCC CTGGCAATGG TGACCCGGCC
(SEQ ID NO: 15)

Figure 9B.

GGGAGACCCC ACCCAGCATG ATGTATGAAT ACCTCCCATT CAAGTGCCCA
(*CTCGAG* ATAACTTCG TATAATGTAT GCTATACGAA GTTAT ATGCATGGCC
TCCGCGCCGG GTTTTGGCGC CTCCCGCGGG CGCCCCCTC CTCACGGCGA
GCGCTGCCAC GTCAGACGAA GGGCGCAGCG AGCGTCCTGA) (SEQ ID NO:16)

Figure 9C.

(TTTCACTGCAT TCTAGTTGTG GTTTGTCCAA ACTCATCAAT GTATCTTATC
ATGTCTGGA ATAACTTCGTATAATGTATGCTATACGAAGTTAT
GCTAGTAACTATAACGGTCCTAAGGTAGCGA *GCTAGC*) GATGCCACCGA
GGACCAGTTGT GCTGCAAGGAA CACTGAAGCG CTCCACC (SEQ ID NO:17)

Figure 9D.

GGGAGACCCC ACCCAGCATG ATGTATGAAT ACCTCCCATT CAAGTGCCCA
(*GTCGAG* ATAACTTCGTATAATGTATGCTATACGAAGTTAT
GCTAGTAACTATAACGGTCCTAAGGTAGCGA *GCTAGC*) GATGCCACCG
AGGACCAGTT GTGCTGCAAG GAACACTGAA GCGCTCCACC (SEQ ID NO:18)

SEQUENCE LISTING

```
<160> NUMBER OF SEQ ID NOS: 30

<210> SEQ ID NO 1
<211> LENGTH: 878
<212> TYPE: DNA
<213> ORGANISM: Rattus norvegicus

<400> SEQUENCE: 1 ataccccga gactgtccac catggttgtg cctattctct gcctcctatg ggccatagca      60
acagcagtgc gacctgcccc agtggcccct ctcggtggtc cagagccggc ccaatatgaa    120
gagttgaccc tgctctttca cggggcccta cagctaggtc aggccctcaa tggtgtgtac    180
aaagccacgg aagctcgcct gacagaagct gggcgcaacc tgggccttt tgaccaagca    240 ctggaatttc tgggaagaga ggtcaatcag ggccgggatg caacacggga gcttcgcacc    300
agcttgtcgg agattcaggc agaagaggac actttacacc ttcgagcaga agccacagcc    360
cgatcgctga gggaagtggc ccgggcccag catgctctgc ggaacagtgt acggagacta    420
caagtgcagc tgagaggtgc ctggctaggc caagcccacc aagaatttga gaatttaaag    480
gatcgagccg ataagcagaa ccacctcttg tgggctctca ctggccacgt gcagcgacag    540
cagcgtgaga tggcagagca gcaacagtgg ctgcggcaga tccagcagag actccacatg    600
gcagccctcc cagcctgaga ctacctggat gccactgagg accagttgtg ctgcagggaa    660
cactgaatgc gctccaccgg gcctatctat gagcagggcc gacagagctg gctgcccatc    720
agctagactt ggccggtgca ccccgcttcc tggcagagca gagacagaag caagcaggcg    780
ggatggaagg cagaagacag ccccgtggag aaggctggag aaggacatga gctcccttat    840
```

```
gccccacacc ccacaataaa aaagaggcaa tctataaa                              878
```

```
<210> SEQ ID NO 2
<211> LENGTH: 198
<212> TYPE: PRT
<213> ORGANISM: Rattus norvegicus

<400> SEQUENCE: 2

Met Val Val Pro Ile Leu Cys Leu Leu Trp Ala Ile Ala Thr Ala Val
1               5                   10                  15

Arg Pro Ala Pro Val Ala Pro Leu Gly Gly Pro Glu Pro Ala Gln Tyr
            20                  25                  30

Glu Glu Leu Thr Leu Leu Phe His Gly Ala Leu Gln Leu Gly Gln Ala
        35                  40                  45

Leu Asn Gly Val Tyr Lys Ala Thr Glu Ala Arg Leu Thr Glu Ala Gly
    50                  55                  60

Arg Asn Leu Gly Leu Phe Asp Gln Ala Leu Glu Phe Leu Gly Arg Glu
65                  70                  75                  80

Val Asn Gln Gly Arg Asp Ala Thr Arg Glu Leu Arg Thr Ser Leu Ser
                85                  90                  95

Glu Ile Gln Ala Glu Glu Asp Thr Leu His Leu Arg Ala Glu Ala Thr
            100                 105                 110

Ala Arg Ser Leu Arg Glu Val Ala Arg Ala Gln His Ala Leu Arg Asn
        115                 120                 125

Ser Val Arg Arg Leu Gln Val Gln Leu Arg Gly Ala Trp Leu Gly Gln
    130                 135                 140

Ala His Gln Glu Phe Glu Asn Leu Lys Asp Arg Ala Asp Lys Gln Asn
145                 150                 155                 160

His Leu Leu Trp Ala Leu Thr Gly His Val Gln Arg Gln Gln Arg Glu
                165                 170                 175

Met Ala Glu Gln Gln Gln Trp Leu Arg Gln Ile Gln Gln Arg Leu His
            180                 185                 190

Met Ala Ala Leu Pro Ala
        195
```

```
<210> SEQ ID NO 3
<211> LENGTH: 887
<212> TYPE: DNA
<213> ORGANISM: Mus musculus

<400> SEQUENCE: 3
tgtcagccat ggctgtgctt gctctctgcc tcctgtggac cttagcatca gcagtgcgac    60
ccgctccagt ggcccctctg gtggtccag agccagctca atatgaagag ctgaccctgc   120
tctttcacgg ggccctgcag ctaggccagg ccctcaatgg cgtgtacaga gccacagagg   180
ctcgcctgac agaagctggg cacagcctgg gcctctatga cagagcactg gaattcctgg   240
ggacagaagt caggcagggc caggatgcca cacaggagct tcgcaccagc ctgtcggaga   300
ttcaggtgga agaggacgct ttacaccttc gagctgaagc cacagcccga tcactggggg   360
aagtggcccg ggcccagcag gctctgcggg acactgtacg agactacaa gtgcagctga   420 gaggcgcctg gctcggtcaa gcccaccaag aatttgagac cttaaaggct cgagctgata   480
agcagagcca cctcttatgg gctctcactg gccacgtgca gcgacagcag cgggagatgg   540
cagagcagca acagtggctg cgacagatcc agcagagact ccacacagca gccctcccag   600
cctgagacta cctggatgcc accgaggacc agttgtgctg caaggaacac tgaagcgctc   660
```

```
caccaggccc atgaacaggg ctgacagagc cggctgccca tcagctggac ctggccagtg    720
caccccgctt cctggcagag cggagacaga agcaagcagg cgggatggaa ggcagaagac    780
agagccctgt ggaggagggc tggaaaaaga cacgagcccc cttatgccca cacaccccac    840
aataaaagag aacagaggca atctaaaaaa aaaaaaaaaa aaaaaaa                  887
```

```
<210> SEQ ID NO 4
<211> LENGTH: 198
<212> TYPE: PRT
<213> ORGANISM: Mus musculus

<400> SEQUENCE: 4

Met Ala Val Leu Ala Leu Cys Leu Leu Trp Thr Leu Ala Ser Ala Val
1               5                   10                  15

Arg Pro Ala Pro Val Ala Pro Leu Gly Gly Pro Glu Pro Ala Gln Tyr
            20                  25                  30

Glu Glu Leu Thr Leu Leu Phe His Gly Ala Leu Gln Leu Gly Gln Ala
        35                  40                  45

Leu Asn Gly Val Tyr Arg Ala Thr Glu Ala Arg Leu Thr Glu Ala Gly
    50                  55                  60

His Ser Leu Gly Leu Tyr Asp Arg Ala Leu Glu Phe Leu Gly Thr Glu
65                  70                  75                  80

Val Arg Gln Gly Gln Asp Ala Thr Gln Glu Leu Arg Thr Ser Leu Ser
                85                  90                  95

Glu Ile Gln Val Glu Glu Asp Ala Leu His Leu Arg Ala Glu Ala Thr
            100                 105                 110

Ala Arg Ser Leu Gly Glu Val Ala Arg Ala Gln Gln Ala Leu Arg Asp
        115                 120                 125

Thr Val Arg Arg Leu Gln Val Gln Leu Arg Gly Ala Trp Leu Gly Gln
    130                 135                 140

Ala His Gln Glu Phe Glu Thr Leu Lys Ala Arg Ala Asp Lys Gln Ser
145                 150                 155                 160

His Leu Leu Trp Ala Leu Thr Gly His Val Gln Arg Gln Arg Glu
                165                 170                 175

Met Ala Glu Gln Gln Gln Trp Leu Arg Gln Ile Gln Gln Arg Leu His
            180                 185                 190

Thr Ala Ala Leu Pro Ala
        195
```

```
<210> SEQ ID NO 5
<211> LENGTH: 888
<212> TYPE: DNA
<213> ORGANISM: Homo sapiens

<400> SEQUENCE: 5
ataccttaga ccctcagtca tgccagtgcc tgctctgtgc ctgctctggg ccctggcaat    60
ggtgacccgg cctgcctcag cggcccccat gggcggccca gaactggcac agcatgagga   120
gctgaccctg ctcttccatg ggaccctgca gctgggccag gccctcaacg tgtgtacag    180 gaccacggag ggacggctga caaaggccag gaacagcctg gtctctatg ccgcacaat    240 agaactcctg gggcaggagg tcagccgggg ccgggatgca gcccaggaac ttcgggcaag   300
cctgttggag actcagatgg aggaggatat tctgcagctg caggcagagg ccacagctga   360
ggtgctgggg gaggtggccc aggcacagaa ggtgctacgg gacagcgtgc agcggctaga   420
agtccagctg aggagcgcct ggctgggccc tgcctaccga gaatttgagg tcttaaaggc   480
```

```
tcacgctgac aagcagagcc acatcctatg ggccctcaca ggccacgtgc agcggcagag    540
gcgggagatg gtggcacagc agcatcggct gcgacagatc caggagagac tccacacagc    600
ggcgctccca gcctgaatct gcctggatgg aactgaggac caatcatgct gcaaggaaca    660
cttccacgcc ccgtgaggcc cctgtgcagg gaggagctgc ctgttcactg ggatcagcca    720
gggcgccggg ccccacttct gagcacagag cagagacaga cgcaggcggg gacaaaggca    780
gaggatgtag ccccattggg gaggggtgga ggaaggacat gtacccttc atgcctacac    840 accccctcatt aaagcagagt cgtggcatct caaaaaaaaa aaaaaaaa              888
```

<210> SEQ ID NO 6
<211> LENGTH: 198
<212> TYPE: PRT
<213> ORGANISM: Homo sapiens

<400> SEQUENCE: 6

```
Met Pro Val Pro Ala Leu Cys Leu Leu Trp Ala Leu Ala Met Val Thr
 1               5                  10                  15

Arg Pro Ala Ser Ala Ala Pro Met Gly Gly Pro Glu Leu Ala Gln His
             20                  25                  30

Glu Glu Leu Thr Leu Leu Phe His Gly Thr Leu Gln Leu Gly Gln Ala
         35                  40                  45

Leu Asn Gly Val Tyr Arg Thr Thr Glu Gly Arg Leu Thr Lys Ala Arg
 50                  55                  60

Asn Ser Leu Gly Leu Tyr Gly Arg Thr Ile Glu Leu Leu Gly Gln Glu
 65                  70                  75                  80

Val Ser Arg Gly Arg Asp Ala Ala Gln Glu Leu Arg Ala Ser Leu Leu
                 85                  90                  95

Glu Thr Gln Met Glu Glu Asp Ile Leu Gln Leu Gln Ala Glu Ala Thr
            100                 105                 110

Ala Glu Val Leu Gly Glu Val Ala Gln Ala Gln Lys Val Leu Arg Asp
        115                 120                 125

Ser Val Gln Arg Leu Glu Val Gln Leu Arg Ser Ala Trp Leu Gly Pro
130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
        195
```

<210> SEQ ID NO 7
<211> LENGTH: 877
<212> TYPE: DNA
<213> ORGANISM: Artificial Sequence
<220> FEATURE:
<223> OTHER INFORMATION: Exemplary Engineered Angpt18 polynucleotide

<400> SEQUENCE: 7

```
tgtcagccat gccagtgcct gctctgtgcc tgctctgggc cctggcaatg gtgacccggc    60
ctgcctcagc ggcccccatg ggcggcccag aactggcaca gcatgaggag ctgaccctgc   120
tcttccatgg gaccctgcag ctgggccagg ccctcaacgg tgtgtacagg accacggagg   180
gacggctgac aaaggccagg aacagcctgg gtctctatgg ccgcacaata gaactcctgg   240
```

```
ggcaggaggt cagccggggc cgggatgcag cccaggaact tcgggcaagc ctgttggaga    300
ctcagatgga ggaggatatt ctgcagctgc aggcagaggc cacagctgag gtgctggggg    360
aggtggccca ggcacagaag gtgctacggg acagcgtgca gcggctagaa gtccagctga    420
ggagcgcctg gctgggccct gcctaccgag aatttgaggt cttaaaggct cacgctgaca    480
agcagagcca catcctatgg gccctcacag gccacgtgca gcggcagagg cgggagatgg    540
tggcacagca gcatcggctg cgacagatcc aggagagact ccacacagcg gcgctcccag    600
cctgaatctg cctggatgga actgaggacc aatcatgctg caaggaacac ttccacgccc    660
cgtgaggccc ctgtgcaggg aggagctgcc tgttcactgg gatcagccag ggcgccgggc    720 ccccacttctg agcacagagc agagacagac gcaggcgggg acaaaggcag aggatgtagc    780
cccattgggg aggggtggag gaaggacatg tacccttca tgcctacaca ccctcatta     840 aagcagagtc gtggcatctc aaaaaaaaaa aaaaaaa                             877
```

<210> SEQ ID NO 8
<211> LENGTH: 198
<212> TYPE: PRT
<213> ORGANISM: Artificial Sequence
<220> FEATURE:
<223> OTHER INFORMATION: Exemplary Engineered Angptl8 polypeptide

<400> SEQUENCE: 8

```
Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
            20                  25                  30

Glu Glu Leu Thr Leu Leu Phe His Gly Thr Leu Gln Leu Gly Gln Ala
        35                  40                  45

Leu Asn Gly Val Tyr Arg Thr Thr Glu Gly Arg Leu Thr Lys Ala Arg
    50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
            100                 105                 110

Ala Glu Val Leu Gly Glu Val Ala Gln Ala Gln Lys Val Leu Arg Asp
        115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
        195
```

<210> SEQ ID NO 9
<211> LENGTH: 2383
<212> TYPE: DNA
<213> ORGANISM: Artificial Sequence
<220> FEATURE:
<223> OTHER INFORMATION: Exemplary synthetic DNA fragment for engineering a non-human Angptl8 gene

<400> SEQUENCE: 9

```
ccagtgcctg ctctgtgcct gctctgggcc ctggcaatgg tgacccggcc tgcctcagcg      60
gcccccatgg gcggcccaga actggcacag catgaggagc tgaccctgct cttccatggg     120
accctgcagc tgggccaggc cctcaacggt gtgtacagga ccacggaggg acggctgaca     180
aaggccagga acagcctggg tctctatggc cgcacaatag aactcctggg gcaggaggtc     240
agccggggcc gggatgcagc ccaggaactt cgggcaagcc tgttggagac tcaggtgggc     300
accgtagctg cgacactgtg gggtggccag gagtccaaag aggagttcgt gtctagggta     360
accaaccatc ctggttttgcc caggactgaa gggattcctg ggatacaaga ttttcagcga     420
taaactcagg caagtcctta ggtacacaaa gatgagttgg acatcctact agtgacccac     480
tgtttattaa gcagatggag gaggatattc tgcagctgca ggcagaggcc acagctgagg     540
tgctggggga ggtggcccag gcacagaagg tgctacggga cagcgtgcag cggctagaag     600
tccagctgag gagcgcctgg ctgggccctg cctaccgaga atttgaggtc ttaaaggtaa     660
ggagctcccc caaccctagt gggctgagac cctgatttcc ggccagaact cgcttctgca     720
ccttgagtcc caaagacctc ccagatcagc ctcccagctc tgtggcctct accctgcatg     780
tccccagaca aaactcaagt cctttttgtgt gcctcagttt ccctttttgtg tgcctcagtt     840
gcaaataagg gcaacacctg atatctcaca gtagggccag gtactcaatg caggtaaaat     900
attcagcatg gggcgggcac acagttggtg ctcaataaat tcttttttttt ttttttttttg     960
agacagagtc tcactgttgc ccaggctgga gtgcagtggt gtgatcttgg ctcactgcaa    1020
cctccacctc ctaggttcaa gtgattctcc tgcctcagcc tcctgagtag ctggaattac    1080
aggtgcacca gctaattttt gtattttta gtagagatgg gatttcacca tgttggccag    1140
gctggtctcg aactcctgac ctcaagggat ctgcctgcct cggtttccca aagtgctggg    1200
attacaggtg tgagccacta cacctggcca ataaattctt actactagag aaactggtaa    1260
cattttgtga gcacccagta agtacccagc actgttctat gcccttttaat aatccatatg    1320
atggccgggc atggtggctc atgcctgtaa tcccagcact ttgggtagct aaggtgggtg    1380
gaacacttaa ggtcaggagt cgagaccac cctggccaac atggtgaaac cccgtctcta    1440
ctaaaaatac aaaaaattag ctgggcgtgg tggcacatgc ctgtagtccc agctactcag    1500
gaggcttagg taggagaatc gcttgaacct gggaggtgga ggttgcagtg agctgagatc    1560
gtgtcattgc actcagcctg ggtgacagag agagactcaa aaaaaaaaaa aaatccatag    1620
gatgttcatc acctccccat gaagtgagtc ctattttatc cccattttac agatggggaa    1680
actgaggcca aagagcattg ttgacttgct gggtcacaca gatacaatga ggggctgggg    1740
cagagggtca ggggatggga ggtgaggtgg ctgtcggctg aggtttccat tctgaccccc    1800
acaggctcac gctgacaagc agagccacat cctatgggcc ctcacaggcc acgtgcagcg    1860
gcagaggcgg gagatggtgg cacagcagca tcggctgcga cagatccagg agaggtgagc    1920
ctggcagggg tttggcaggc agggcagttg gatgggggc gcacagggca gctggaaagg    1980
ggcccctca cctgggctga gccacatctc cctccccaga ctccacacag cggcgctccc    2040
agcctgaatc tgcctggatg gaactgagga ccaatcatgc tgcaaggaac acttccacgc    2100
cccgtgagc ccctgtgcag ggaggagctg cctgttcact gggatcagcc agggcgccgg    2160
gccccacttc tgagcacaga gcagagacag acgcaggcgg ggacaaaggc agaggatgta    2220
gccccattgg ggaggggtgg aggaaggaca tgtacccttt catgcctaca caccccctcat    2280
```

```
taaagcagag tcgtggcatc tcacccaggg tgtctgtgtg tgtccttggc ttagggagac    2340
cccacccagc atgatgtatg aatacctccc attcaagtgc cca                     2383

<210> SEQ ID NO 10
<211> LENGTH: 7473
<212> TYPE: DNA
<213> ORGANISM: Artificial Sequence
<220> FEATURE:
<223> OTHER INFORMATION: Exemplary engineered Angptl8 allele including a
      selection cassette

<400> SEQUENCE: 10
cacgaaactg tcagccatgc cagtgcctgc tctgtgcctg ctctgggccc tggcaatggt      60
gacccggcct gcctcagcgg cccccatggg cggcccagaa ctggcacagc atgaggagct     120
gaccctgctc ttccatggga ccctgcagct gggccaggcc ctcaacggtg tgtacaggac     180
cacggaggga cggctgacaa aggccaggaa cagcctgggt ctctatggcc gcacaataga     240
actcctgggg caggaggtca gccggggccg ggatgcagcc caggaacttc gggcaagcct     300
gttggagact caggtgggca ccgtagctgc gacactgtgg ggtggccagg agtccaaaga     360
ggagttcgtg tctagggtaa ccaaccatcc tggtttgccc aggactgaag ggattcctgg     420
gatacaagat tttcagcgat aaactcaggc aagtccttag gtacacaaag atgagttgga     480
catcctacta gtgacccact gtttattaag cagatggagg aggatattct gcagctgcag     540
gcagaggcca cagctgaggt gctgggggag gtgcccagg cacagaaggt gctacgggac     600
agcgtgcagc ggctagaagt ccagctgagg acgcctggc tgggccctgc ctaccgagaa     660
tttgaggtct taaaggtaag gagctccccc aaccctagtg ggctgagacc ctgatttccg     720
gccagaactc gcttctgcac cttgagtccc aaagacctcc cagatcagcc tcccagctct     780
gtggcctcta ccctgcatgt ccccagacaa aactcaagtc cttttgtgtg cctcagtttc     840
ccttttgtgt gcctcagttg caaataaggg caacacctga tatctcacag tagggccagg     900
tactcaatgc aggtaaaata ttcagcatgg ggcgggcaca cagttggtgc tcaataaatt     960
cttttttttt ttttttttga cagagtctc actgttgcc caggctggag tgcagtggtg     1020
tgatcttggc tcactgcaac ctccacctcc taggttcaag tgattctcct gcctcagcct     1080
cctgagtagc tggaattaca ggtgcaccag ctaattttg tatttttag tagagatggg     1140 atttcaccat gttggccagg ctggtctcga actcctgacc tcagggatc tgcctgcctc     1200 ggtttcccaa agtgctggga ttacaggtgt gagccactac acctggccaa taaattctta     1260
ctactagaga aactggtaac attttgtgag cacccagtaa gtacccagca ctgttctatg     1320 cccttttaata atccatatga tggccgggca tggtggctca tgcctgtaat cccagcactt     1380
tgggtagcta aggtgggtgg aacacttaag gtcaggagtt cgagaccacc ctggccaaca     1440
tggtgaaacc ccgtctctac taaaaataca aaaattagc tgggcgtggt ggcacatgcc     1500
tgtagtccca gctactcagg aggcttaggt aggagaatcg cttgaacctg ggaggtggag     1560
gttgcagtga gctgagatcg tgtcattgca ctcagcctgg gtgacagaga gagactcaaa     1620
aaaaaaaaaa aatccatagg atgttcatca cctccccatg aagtgagtcc tattttatcc     1680 ccatttaca gatggggaaa ctgaggccaa agagcattgt tgacttgctg ggtcacacag     1740
atacaatgag gggctgggc agagggtcag gggatgggag gtgaggtggc tgtcggctga     1800
ggtttccatt ctgaccccca caggctcacg ctgacaagca gagccacatc ctatgggccc     1860
tcacaggcca cgtgcagcgg cagaggcggg agatggtggc acagcagcat cggctgcgac     1920
```

```
agatccagga gaggtgagcc tggcaggggt ttggcaggca gggcagttgg atgggggcg    1980
cacagggcag ctggaaaggg gccccctcac ctgggctgag ccacatctcc ctccccagac    2040
tccacacagc ggcgctccca gcctgaatct gcctggatgg aactgaggac caatcatgct    2100
gcaaggaaca cttccacgcc ccgtgaggcc cctgtgcagg gaggagctgc ctgttcactg    2160
ggatcagcca gggcgccggg ccccacttct gagcacagag cagagacaga cgcaggcggg    2220
gacaaaggca gaggatgtag ccccattggg gaggggtgga ggaaggacat gtacccttc    2280
atgcctacac acccctcatt aaagcagagt cgtggcatct cacccagggt gtctgtgtgt    2340
gtccttggct tagggagacc ccacccagca tgatgtatga ataccccca ttcaagtgcc    2400
cactcgagat aacttcgtat aatgtatgct atacgaagtt atatgcatgg cctccgcgcc    2460
gggttttggc gcctcccgcg ggcgcccccc tcctcacggc gagcgctgcc acgtcagacg    2520
aagggcgcag cgagcgtcct gatccttccg cccggacgct caggacagcg gcccgctgct    2580
cataagactc ggccttagaa ccccagtatc agcagaagga cattttagga cgggacttgg    2640
gtgactctag ggcactggtt ttctttccag agagcggaac aggcgaggaa aagtagtccc    2700
ttctcggcga ttctgcggag ggatctccgt ggggcggtga acgccgatga ttatataagg    2760
acgcgccggg tgtggcacag ctagttccgt cgcagccggg atttgggtcg cggttcttgt    2820
ttgtggatcg ctgtgatcgt cacttggtga gtagcgggct gctgggctgg ccggggcttt    2880
cgtggccgcc gggccgctcg gtgggacgga agcgtgtgga gagaccgcca agggctgtag    2940
tctgggtccg cgagcaaggt tgccctgaac tgggggttgg ggggagcgca gcaaaatggc    3000
ggctgttccc gagtcttgaa tggaagacgc ttgtgaggcg ggctgtgagg tcgttgaaac    3060
aaggtggggg gcatggtggg cggcaagaac ccaaggtctt gaggccttcg ctaatgcggg    3120
aaagctctta ttcgggtgag atgggctggg gcaccatctg ggaccctga cgtgaagttt    3180
gtcactgact ggagaactcg gtttgtcgtc tgttgcgggg gcggcagtta tggcggtgcc    3240
gttgggcagt gcacccgtac cttgggagc gcgcgccctc gtcgtgtcgt gacgtcaccc    3300
gttctgttgg cttataatgc agggtggggc cacctgccgg taggtgtgcg gtaggctttt    3360
ctccgtcgca ggacgcaggg ttcgggccta gggtaggctc tcctgaatcg acaggcgccg    3420
gacctctggt gaggggaggg ataagtgagg cgtcagtttc tttggtcggt tttatgtacc    3480
tatcttctta agtagctgaa gctccggttt tgaactatgc gctcgggtt ggcgagtgtg    3540
ttttgtgaag ttttttaggc acctttgaa atgtaatcat ttgggtcaat atgtaatttt    3600
cagtgttaga ctagtaaatt gtccgctaaa ttctggccgt ttttggcttt tttgttagac    3660
gtgttgacaa ttaatcatcg gcatagtata tcggcatagt ataatacgac aaggtgagga    3720
actaaaccat gggatcggcc attgaacaag atggattgca cgcaggttct ccggccgctt    3780
gggtggagag gctattcggc tatgactggg cacaacagac aatcggctgc tctgatgccg    3840
ccgtgttccg gctgtcagcg cagggcgccc cggttctttt tgtcaagacc gacctgtccg    3900
gtgccctgaa tgaactgcag gacgaggcag cgcggctatc gtggctggcc acgacgggcg    3960
ttccttgcgc agctgtgctc gacgttgtca ctgaagcggg aagggactgg ctgctattgg    4020
gcgaagtgcc ggggcaggat ctcctgtcat ctcaccttgc tcctgccgag aaagtatcca    4080
tcatggctga tgcaatgcgg cggctgcata cgcttgatcc ggctacctgc ccattcgacc    4140
accaagcgaa acatcgcatc gagcgagcac gtactcggat ggaagccggt cttgtcgatc    4200
aggatgatct ggacgaagag catcagggc tcgcgccagc cgaactgttc gccaggctca    4260
```

```
aggcgcgcat gcccgacggc gatgatctcg tcgtgaccca tggcgatgcc tgcttgccga    4320
atatcatggt ggaaaatggc cgcttttctg gattcatcga ctgtggccgg ctgggtgtgg    4380
cggaccgcta tcaggacata gcgttggcta cccgtgatat tgctgaagag cttggcggcg    4440
aatgggctga ccgcttcctc gtgctttacg gtatcgccgc tcccgattcg cagcgcatcg    4500
ccttctatcg ccttcttgac gagttcttct gaggggatcc gctgtaagtc tgcagaaatt    4560
gatgatctat aaacaataa agatgtccac taaaatggaa gttttcctg tcatactttg    4620 ttaagaaggg tgagaacaga gtacctacat tttgaatgga aggattggag ctacggggt    4680 gggggtgggg tgggattaga taaatgcctg ctctttactg aaggctcttt actattgctt    4740
tatgataatg tttcatagtt ggatatcata atttaaacaa gcaaaccaa attaagggcc    4800 agctcattcc tcccactcat gatctataga tctatagatc tctcgtggga tcattgtttt    4860
tctcttgatt cccactttgt ggttctaagt actgtggttt ccaaatgtgt cagtttcata    4920
gcctgaagaa cgagatcagc agcctctgtt ccacatacac ttcattctca gtattgtttt    4980
gccaagttct aattccatca gacctcgacc tgcagcccct agcccgggcg ccagtagcag    5040
cacccacgtc caccttctgt ctagtaatgt ccaacacctc cctcagtcca aacactgctc    5100
tgcatccatg tggctcccat ttatacctga agcacttgat ggggcctcaa tgttttacta    5160
gagcccaccc ccctgcaact ctgagaccct ctggatttgt ctgtcagtgc ctcactgggg    5220
cgttggataa tttcttaaaa ggtcaagttc cctcagcagc attctctgag cagtctgaag    5280
atgtgtgctt ttcacagttc aaatccatgt ggctgtttca cccacctgcc tggccttggg    5340
ttatctatca ggacctagcc tagaagcagg tgtgtggcac ttaacaccta agctgagtga    5400
ctaactgaac actcaagtgg atgccatctt tgtcacttct tgactgtgac acaagcaact    5460
cctgatgcca aagccctgcc caccctctc atgcccatat ttggacatgg tacaggtcct    5520
cactggccat ggtctgtgag gtcctggtcc tctttgactt cataattcct aggggccact    5580
agtatctata agaggaagag ggtgctggct cccaggccac agcccacaaa attccacctg    5640
ctcacaggtt ggctggctcg acccaggtgg tgtcccctgc tctgagccag ctcccggcca    5700
agccagcacc atgggtaccc ccaagaagaa gaggaaggtg cgtaccgatt taaattccaa    5760
tttactgacc gtacaccaaa atttgcctgc attaccggtc gatgcaacga gtgatgaggt    5820
tcgcaagaac ctgatggaca tgttcaggga tcgccaggcg ttttctgagc atacctggaa    5880
aatgcttctg tccgtttgcc ggtcgtgggc ggcatggtgc aagttgaata accggaaatg    5940
gtttcccgca gaacctgaag atgttcgcga ttatcttcta tatcttcagg cgcgcggtct    6000
ggcagtaaaa actatccagc aacatttggg ccagctaaac atgcttcatc gtcggtccgg    6060
gctgccacga ccaagtgaca gcaatgctgt ttcactggtt atgcggcgga tccgaaaaga    6120
aaacgttgat gccggtgaac gtgcaaaaca ggctctagcg ttcgaacgca ctgatttcga    6180
ccaggttcgt tcactcatgg aaaatagtga tcgctgccag gatatacgta atctggcatt    6240 tctgggatt gcttataaca ccctgttacg tatagccgaa attgccagga tcagggttaa    6300
agatatctca cgtactgacg gtgggagaat gttaatccat attggcagaa cgaaaacgct    6360
ggttagcacc gcaggtgtag agaaggcact tagcctgggg gtaactaaac tggtcgagcg    6420
atggatttcc gtctctggtg tagctgatga tccgaataac tacctgtttt gccgggtcag    6480
aaaaaatggt gttgccgcgc catctgccac cagccagcta tcaactcgcg ccctggaagg    6540 gattttgaa gcaactcatc gattgattta cggcgctaag gtaaatataa aatttttaag    6600
tgtataatgt gttaaactac tgattctaat tgtttgtgta ttttaggatg actctggtca    6660
```

```
gagatacctg gcctggtctg gacacagtgc ccgtgtcgga gccgcgcgag atatggcccg    6720
cgctggagtt tcaataccgg agatcatgca agctggtggc tggaccaatg taaatattgt    6780
catgaactat atccgtaacc tggatagtga acaggggca atggtgcgcc tgctggaaga     6840
tggcgattga tctagataag taatgatcat aatcagccat atcacatctg tagaggtttt    6900
acttgcttta aaaaacctcc cacacctccc cctgaacctg aaacataaaa tgaatgcaat    6960
tgttgttgtt aaacctgccc tagttgcggc caattccagc tgagcgtgcc tccgcaccat    7020
taccagttgg tctggtgtca aaaataataa taaccgggca gggggatct aagctctaga     7080 taagtaatga tcataatcag ccatatcaca tctgtagagg ttttacttgc tttaaaaaac    7140
ctcccacacc tcccctgaa  cctgaaacat aaaatgaatg caattgttgt tgttaacttg    7200
tttattgcag cttataatgg ttacaaataa agcaatagca tcacaaattt cacaaataaa    7260
gcattttttt cactgcattc tagttgtggt ttgtccaaac tcatcaatgt atcttatcat    7320
gtctggaata acttcgtata atgtatgcta tacgaagtta tgctagtaac tataacggtc    7380
ctaaggtagc gagctagcga tgccaccgag gaccagttgt gctgcaagga acactgaagc    7440
gctccaccag gcccatgaac agggctgaca gag                                 7473
```

<210> SEQ ID NO 11
<211> LENGTH: 2554
<212> TYPE: DNA
<213> ORGANISM: Artificial Sequence
<220> FEATURE:
<223> OTHER INFORMATION: Exemplary engineered Angptl8 allele after recombinase-mediated excision of a selection cassette

<400> SEQUENCE: 11

```
cacgaaactg tcagccatgc cagtgcctgc tctgtgcctg ctctgggccc tggcaatggt      60
gacccggcct gcctcagcgg cccccatggg cggcccagaa ctggcacagc atgaggagct     120
gaccctgctc ttccatggga ccctgcagct ggggccaggcc ctcaacggtg tgtacaggac    180
cacggaggga cggctgacaa aggccaggaa cagcctgggt ctctatggcc gcacaataga    240
actcctgggg caggaggtca gccggggccg ggatgcagcc caggaacttc gggcaagcct    300
gttggagact caggtgggca ccgtagctgc gacactgtgg ggtggccagg agtccaaaga    360
ggagttcgtg tctagggtaa ccaaccatcc tggtttgccc aggactgaag ggattcctgg    420
gatacaagat tttcagcgat aaactcaggc aagtccttag gtacacaaag atgagttgga    480
catcctacta gtgacccact gtttattaag cagatggagg aggatattct gcagctgcag    540
gcagaggcca cagctgaggt gctggggag  gtggcccagg cacagaaggt gctacgggac    600
agcgtgcagc ggctagaagt ccagctgagg agcgcctggc tgggccctgc ctaccgagaa    660
tttgaggtct taaaggtaag gagctccccc aaccctagtg ggctgagacc ctgatttccg    720
gccagaactc gcttctgcac cttgagtccc aaagacctcc cagatcagcc tcccagctct    780
gtggcctcta ccctgcatgt ccccagacaa aactcaagtc cttttgtgtg cctcagtttc    840 cctttttgtgt gcctcagttg caaataaggg caacacctga tatctcacag tagggccagg    900
tactcaatga aggtaaaata ttcagcatgg ggcgggcaca cagttggtgc tcaataaatt    960
cttttttttt tttttttga cacagagtct cactgttgcc caggctggag tgcagtggtg    1020
tgatcttggc tcactgcaac ctccacctcc taggttcaag tgattctcct gcctcagcct    1080
cctgagtagc tggaattaca ggtgcaccag ctaattttg tatttttag tagagatggg     1140 atttcaccat gttggccagg ctggtctcga actcctgacc tcaagggatc tgcctgcctc    1200
```

```
ggtttcccaa agtgctggga ttacaggtgt gagccactac acctggccaa taaattctta    1260
ctactagaga aactggtaac attttgtgag cacccagtaa gtacccagca ctgttctatg    1320 cccctttaata atccatatga tggccgggca tggtggctca tgcctgtaat cccagcactt    1380
tgggtagcta aggtgggtgg aacacttaag gtcaggagtt cgagaccacc ctggccaaca    1440
tggtgaaacc ccgtctctac taaaaataca aaaaattagc tgggcgtggt ggcacatgcc    1500
tgtagtccca gctactcagg aggcttaggt aggagaatcg cttgaacctg ggaggtggag    1560
gttgcagtga gctgagatcg tgtcattgca ctcagcctgg gtgacagaga gagactcaaa    1620
aaaaaaaaaa aatccatagg atgttcatca cctccccatg aagtgagtcc tattttatcc    1680 ccatttttaca gatggggaaa ctgaggccaa agagcattgt tgacttgctg ggtcacacag    1740
atacaatgag gggctgggc agagggtcag gggatgggag gtgaggtggc tgtcggctga    1800
ggtttccatt ctgaccccca caggctcacg ctgacaagca gagccacatc ctatgggccc    1860
tcacaggcca cgtgcagcgg cagaggcggg agatggtggc acagcagcat cggctgcgac    1920
agatccagga gaggtgagcc tggcaggggt ttggcaggca gggcagttgg atgggggcg    1980 cacagggcag ctggaaaggg gccccctcac ctgggctgag ccacatctcc ctccccagac    2040
tccacacagc ggcgctccca gcctgaatct gcctggatgg aactgaggac caatcatgct    2100
gcaaggaaca cttccacgcc ccgtgaggcc cctgtgcagg gaggagctgc ctgttcactg    2160
ggatcagcca gggcgccggg ccccacttct gagcacagag cagagacaga cgcaggcggg    2220
gacaaaggca gaggatgtag ccccattggg gaggggtgga ggaaggacat gtaccctttc    2280
atgcctacac acccctcatt aaagcagagt cgtggcatct cacccagggt gtctgtgtgt    2340
gtccttggct tagggagacc ccacccagca tgatgtatga ataccctccca ttcaagtgcc    2400 cactcgagat aacttcgtat aatgtatgct atacgaagtt atgctagtaa ctataacggt    2460
cctaaggtag cgagctagcg atgccaccga ggaccagttg tgctgcaagg aacactgaag    2520
cgctccacca ggcccatgaa cagggctgac agag                                2554
```

<210> SEQ ID NO 12
<211> LENGTH: 680
<212> TYPE: DNA
<213> ORGANISM: Artificial Sequence
<220> FEATURE:
<223> OTHER INFORMATION: Protamine 1 (Prm1) promoter

<400> SEQUENCE: 12

```
ccagtagcag cacccacgtc caccttctgt ctagtaatgt ccaacacctc cctcagtcca     60
aacactgctc tgcatccatg tggctcccat ttatacctga agcacttgat ggggcctcaa    120
tgttttacta gagcccaccc ccctgcaact ctgagaccct ctggatttgt ctgtcagtgc    180
ctcactgggg cgttggataa tttcttaaaa ggtcaagttc cctcagcagc attctctgag    240
cagtctgaag atgtgtgctt ttcacagttc aaatccatgt ggctgtttca cccacctgcc    300
tggccttggg ttatctatca ggacctagcc tagaagcagg tgtgtggcac ttaaacccta    360
agctgagtga ctaactgaac actcaagtgg atgccatctt tgtcacttct tgactgtgac    420
acaagcaact cctgatgcca aagccctgcc cacccctctc atgcccatat ttggacatgg    480
tacaggtcct cactggccat ggtctgtgag gtcctggtcc tctttgactt cataattcct    540
aggggccact agtatctata agaggaagag ggtgctggct cccaggccac agcccacaaa    600
attccacctg ctcacaggtt ggctggctcg acccaggtgg tgtccctgc tctgagccag    660
```
ctcccggcca agccagcacc 680

<210> SEQ ID NO 13
<211> LENGTH: 1052
<212> TYPE: DNA
<213> ORGANISM: Artificial Sequence
<220> FEATURE:
<223> OTHER INFORMATION: Blimp1 promoter 1kb

<400> SEQUENCE: 13

| | | | | | |
|---|---|---|---|---|---|
| tgccatcatc | acaggatgtc | cttccttctc | cagaagacag | actggggctg | aaggaaaagc | 60 |
| cggccaggct | cagaacgagc | cccactaatt | actgcctcca | acagctttcc | actcactgcc | 120 |
| cccagcccaa | catccccttt | ttaactggga | agcattccta | ctctccattg | tacgcacacg | 180 |
| ctcggaagcc | tggctgtggg | tttgggcatg | agaggcaggg | acaacaaaac | cagtatatat | 240 |
| gattataact | ttttcctgtt | tccctatttc | caaatggtcg | aaaggaggaa | gttaggtcta | 300 |
| cctaagctga | atgtattcag | ttagcaggag | aaatgaaatc | ctatacgttt | aatactagag | 360 |
| gagaaccgcc | ttagaatatt | tatttcattg | gcaatgactc | caggactaca | cagcgaaatt | 420 |
| gtattgcatg | tgctgccaaa | atactttagc | tctttccttc | gaagtacgtc | ggatcctgta | 480 |
| attgagacac | cgagtttagg | tgactagggt | tttcttttga | ggaggagtcc | cccaccccgc | 540 |
| cccgctctgc | cgcgacagga | agctagcgat | ccggaggact | tagaatacaa | tcgtagtgtg | 600 |
| ggtaaacatg | gagggcaagc | gcctgcaaag | ggaagtaaga | agattcccag | tccttgttga | 660 |
| aatccatttg | caaacagagg | aagctgccgc | gggtcgcagt | cggtggggg | aagccctgaa | 720 |
| ccccacgctg | cacggctggg | ctggccaggt | gcggccacgc | cccatcgcg | gcggctggta | 780 |
| ggagtgaatc | agaccgtcag | tattggtaaa | gaagtctgcg | gcagggcagg | gaggggaag | 840 |
| agtagtcagt | cgctcgctca | ctcgctcgct | cgcacagaca | ctgctgcagt | gacactcggc | 900 |
| cctccagtgt | cgcggagacg | caagagcagc | gcgcagcacc | tgtccgcccg | gagcgagccc | 960 |
| ggcccgcggc | cgtagaaaag | gagggaccgc | cgaggtgcgc | gtcagtactg | ctcagcccgg | 1020 |
| cagggacgcg | ggaggatgtg | gactgggtgg | ac | | | 1052 |

<210> SEQ ID NO 14
<211> LENGTH: 2008
<212> TYPE: DNA
<213> ORGANISM: Artificial Sequence
<220> FEATURE:
<223> OTHER INFORMATION: Blimp1 promoter 2kb

<400> SEQUENCE: 14

| | | | | | |
|---|---|---|---|---|---|
| gtggtgctga | ctcagcatcg | gttaataaac | cctctgcagg | aggctggatt | tcttttgttt | 60 |
| aattatcact | tggaccttc | tgagaactct | taagaattgt | tcattcgggt | ttttttgttt | 120 |
| tgttttggtt | tggtttttttt | gggttttttt | ttttttttt | ttttggttt | ttggagacag | 180 |
| ggtttctctg | tatatagccc | tggcacaaga | gcaagctaac | agcctgtttc | ttcttggtgc | 240 |
| tagcgccccc | tctggcagaa | aatgaaataa | caggtggacc | tacaaccccc | ccccccccc | 300 |
| ccagtgtatt | ctactcttgt | ccccggtata | aatttgattg | ttccgaacta | cataaattgt | 360 |
| agaaggattt | tttagatgca | catatcattt | tctgtgatac | cttccacaca | ccctccccc | 420 |
| ccaaaaaaat | ttttctggga | aagtttcttg | aaaggaaaac | agaagaacaa | gcctgtcttt | 480 |
| atgattgagt | tgggcttttg | ttttgctgtg | tttcatttct | tcctgtaaac | aaatactcaa | 540 |
| atgtccactt | cattgtatga | ctaagttggt | atcattaggt | tgggtctggg | tgtgtgaatg | 600 |
| tgggtgtgga | tctggatgtg | ggtgggtgtg | tatgccccgt | gtgtttagaa | tactagaaaa | 660 |

```
gataccacat cgtaaacttt tgggagagat gattttaaa aatgggggtg ggggtgaggg       720
gaacctgcga tgaggcaagc aagataaggg gaagacttga gtttctgtga tctaaaaagt      780
cgctgtgatg ggatgctggc tataaatggg cccttagcag cattgtttct gtgaattgga      840
ggatccctgc tgaaggcaaa agaccattga aggaagtacc gcatctggtt tgttttgtaa      900
tgagaagcag gaatgcaagg tccacgctct taataataaa caaacaggac attgtatgcc      960
atcatcacag gatgtccttc cttctccaga agacagactg gggctgaagg aaaagccggc     1020
caggctcaga acgagcccca ctaattactg cctccaacag ctttccactc actgccccca     1080
gcccaacatc ccctttttaa ctgggaagca ttcctactct ccattgtacg cacacgctcg     1140
gaagcctggc tgtgggtttg gcatgagag gcagggacaa caaaaccagt atatatgatt      1200
ataacttttt cctgtttccc tatttccaaa tggtcgaaag gaggaagtta ggtctaccta     1260
agctgaatgt attcagttag caggagaaat gaaatcctat acgtttaata ctagaggaga     1320
accgccttag aatatttatt tcattggcaa tgactccagg actacacagc gaaattgtat     1380
tgcatgtgct gccaaaatac tttagctctt tccttcgaag tacgtcggat cctgtaattg     1440
agacaccgag tttaggtgac tagggttttc ttttgaggag gagtccccca ccccgccccg     1500
ctctgccgcg acaggaagct agcgatccgg aggacttaga atacaatcgt agtgtgggta     1560
aacatggagg gcaagcgcct gcaaagggaa gtaagaagat tcccagtcct tgttgaaatc     1620
catttgcaaa cagaggaagc tgccgcgggt cgcagtcggt ggggggaagc cctgaacccc     1680
acgctgcacg gctgggctgg ccaggtgcgg ccacgccccc atcgcggcgg ctggtaggag     1740
tgaatcagac cgtcagtatt ggtaaagaag tctgcggcag ggcagggagg gggaagagta     1800
gtcagtcgct cgctcactcg ctcgctcgca cagacactgc tgcagtgaca ctcggccctc     1860
cagtgtcgcg gagacgcaag agcagcgcgc agcacctgtc cgcccggagc gagcccggcc     1920
cgcggccgta gaaaaggagg gaccgccgag gtgcgcgtca gtactgctca gcccggcagg     1980
gacgcgggag gatgtggact gggtggac                                       2008

<210> SEQ ID NO 15
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 15
aaggcagccg cagcggcccg ggaaccacac ccacgaaact gtcagccatg ccagtgcctg        60
ctctgtgcct gctctgggcc ctggcaatgg tgacccggcc                            100

<210> SEQ ID NO 16
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 16
gggagacccc acccagcatg atgtatgaat acctcccatt caagtgccca ctcgagataa        60
cttcgtataa tgtatgctat acgaagttat atgcatggcc tccgcgccgg gttttggcgc       120
ctcccgcggg cgcccccctc ctcacggcga                                       150

<210> SEQ ID NO 17
```

```
<211> LENGTH: 181
<212> TYPE: DNA
<213> ORGANISM: Artificial Sequence
<220> FEATURE:
<223> OTHER INFORMATION: Synthetic polynucleotide

<400> SEQUENCE: 17
tttcactgca ttctagttgt ggtttgtcca aactcatcaa tgtatcttat catgtctgga      60
ataacttcgt ataatgtatg ctatacgaag ttatgctagt aactataacg gtcctaaggt     120
agcgagctag cgatgccacc gaggaccagt tgtgctgcaa ggaacactga agcgctccac     180
c                                                                    181

<210> SEQ ID NO 18
<211> LENGTH: 177
<212> TYPE: DNA
<213> ORGANISM: Artificial Sequence
<220> FEATURE:
<223> OTHER INFORMATION: Synthetic polynucleotide

<400> SEQUENCE: 18
gggagacccc acccagcatg atgtatgaat acctcccatt caagtgccca gtcgagataa      60
cttcgtataa tgtatgctat acgaagttat gctagtaact ataacggtcc taaggtagcg     120
agctagcgat gccaccgagg accagttgtg ctgcaaggaa cactgaagcg ctccacc        177

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19
ggtgttggtg gcaggtaaga gt                                              22

<210> SEQ ID NO 20
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 20
tgaggaaatg gtaaacccag aacaga                                          26

<210> SEQ ID NO 21
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 21
tggtgtgtca tcagggtatg tttc                                            24

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22
tgagcctggt gggattactc t                                               21
```

<210> SEQ ID NO 23
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 23
tagcagtgga agttgcctag gtcc                                           24

<210> SEQ ID NO 24
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 24
ccgtcaaggc cagtgctt                                                  18

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
gcaagcctgt tggagactca g                                              21

<210> SEQ ID NO 26
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 26
caccgtagct gcgacactgt gg                                             22

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
agacacgaac tcctctttgg a                                              21

<210> SEQ ID NO 28
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 28
tgggctgagc cacatctc                                                  18

<210> SEQ ID NO 29
<211> LENGTH: 21
<212> TYPE: DNA
<213> ORGANISM: Artificial Sequence
<220> FEATURE:

```
<223> OTHER INFORMATION: synthetic oligonucleotide

<400> SEQUENCE: 29
cagactccac acagcggcgc t                                              21

<210> SEQ ID NO 30
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 30
tcagttccat ccaggcagat tc                                             22
```

NON-HUMAN ANIMALS HAVING AN ENGINEERED ANGPTL8 GENE

CROSS REFERENCE TO RELATED APPLICATION

This application claims the benefit of priority from U.S. Provisional Application No. 62/291,446, filed Feb. 4, 2016, the entire contents of which are incorporated herein by reference.

INCORPORATION BY REFERENCE OF SEQUENCE LISTING

The sequence listing in an ASCII text file, named as 34634_10232US01_SequenceListing of 38 kb, created on Feb. 2, 2017, and submitted to the United States Patent and Trademark Office via EFS-Web, is incorporated herein by reference.

BACKGROUND

According to the World Health Organization (WHO), cardiovascular diseases are the number one cause of death each year. In particular, it is estimated that 17.5 million people died from cardiovascular diseases in 2012, which accounts for about 31% of all global deaths. Cardiovascular diseases include disorders of the heart and blood and have several associated risk factors, which most notably include behavioral risk factors such as tobacco and/or alcohol use, unhealthy diet and obesity, and physical inactivity. Such behavioral risk factors include, for example, high blood pressure, high blood sugar and/or high blood lipid levels. Lipids (fat), which include both cholesterol and triglycerides, are not soluble in blood and are transported through the bloodstream via lipoproteins. Having high blood lipid levels can increase the risk for cardiovascular disease and require management via medicine, and, in some cases, surgery.

SUMMARY

The present invention encompasses the recognition that it is desirable to engineer non-human animals to permit improved in vivo systems for identifying and developing new therapeutics and/or therapeutic regimens that can be used for the treatment of metabolic disorders that are, in some embodiments, characterized by lipid dysfunction. The present invention also encompasses the recognition that it is desirable to engineer non-human animals to permit improved in vivo systems for identifying and developing new therapeutics that can be used to treat cardiovascular diseases, disorders or conditions. Further, the present invention also encompasses the recognition that non-human animals having an engineered Angiopoietin-like protein 8 (Angptl8) gene and/or otherwise expressing, containing (e.g., in the blood), or producing a human or humanized Angiopoietin-like protein 8 polypeptide are desirable, for example for use in identifying and developing therapeutics that can be used for the treatment of hypertriglyceridemia.

In some embodiments, non-human animals having a genome comprising an engineered Angptl8 gene are provided, which engineered Angptl8 gene includes genetic material from two different species (e.g., a human and a non-human). In some embodiments, such an engineered Angptl8 gene includes genetic material that encodes one or more coiled-coil domains of a human ANGPTL8 polypeptide. In some embodiments, such an engineered Angptl8 gene includes genetic material that encodes art N-terminal region, in whole or in part, of a human ANGPTL8 polypeptide. Thus, in some embodiments, an engineered Angptl8 gene of a non-human animal as described herein encodes an Angptl8 polypeptide that has a sequence that is all or substantially all human. In various embodiments, an Angptl8 polypeptide expressed by a non-human animal as described herein is expressed under the control of a non-human promoter (e.g., a non-human Angptl8 promoter).

In some embodiments, a non-human animal is provided, whose genome comprises an Angptl8 gene that comprises an endogenous portion and a human portion, wherein the endogenous and human portions are operably linked to non-human Angptl8 regulatory elements.

In some embodiments, a non-human animal is provided, that expresses a human ANGPTL8 polypeptide under the control of non-human Angptl8 regulatory elements.

In some embodiments, an endogenous portion of an Angptl8 gene includes or comprises an endogenous non-human Angptl8 promoter. In some embodiments, an endogenous portion of an Angptl8 gene includes or comprises a 3' region or sequence immediately downstream of the 3' untranslated region of an endogenous non-human Angptl8 gene at the endogenous non-human Angptl8 locus.

In some embodiments, an endogenous portion of an Angptl8 gene includes or comprises 5' and/or 3' untranslated regions (UTRs). In some embodiments, an endogenous portion of an Angptl8 gene includes 5' and/or 3' untranslated regions (UTRs) and further includes an endogenous Angptl8 ATG start codon. In some embodiments, 5' and 3' UTRs of an endogenous Angptl8 gene each have a sequence that is substantially identical or identical to the corresponding 5' and 3' UTRs that appear in a rodent Angptl8 gene. In some certain embodiments, 5' and 3' UTRs of an endogenous Angptl8 gene each have a sequence that is at least 50%, at least 55%, at least 60%, at least 65%, at least 70%, at least 75%, at least 80%, at least 85%, at least 90%, at least 95%, or at least 98% identical to the corresponding 5' and 3' UTRs that appear in SEQ ID NO:1 or SEQ ID NO:3.

In some embodiments, an Angptl8 gene as described herein encodes a polypeptide having a sequence at least 50%, at least 55%, at least 60%, at least 65%, at least 70%, at least 75%, at least 80%, at least 85%, at least 90%, at least 95%, or at least 98% identical to SEQ ID NO:6 or SEQ ID NO:8. In some embodiments, an Angptl8 gene as described herein encodes a polypeptide having a sequence that is substantially identical or identical to SEQ ID NO:6 or SEQ ID NO:8.

In some embodiments, a human portion includes or comprises exons 1-4, in whole or in part, of a human ANGPTL8 gene. In some embodiments, exons 1-4, in whole or in part, of a human ANGPTL8 gene are at least 50%, at least 55%, at least 60%, at least 65%, at least 70%, at least 75%, at least 80%, at least 85%, at least 90%, at least 95%, or at least 98% identical to the corresponding exons 1-4, in whole or in part, that appear in a human ANGPTL8 mRNA sequence of SEQ ID NO:5. In some embodiments, exons 1-4, in whole or in part, of a human ANGPTL8 gene are substantially identical or identical to the corresponding exons 1-4, in whole or in part, that appear in a human ANGPTL8 mRNA sequence of SEQ ID NO:5. In some embodiments, a human portion further comprises the 3'UTR of a human ANGPTL8 gene. In some embodiments, a human portion comprises a sequence that is codon-optimized for expression in a non-human animal.

In some embodiments, a human ANGPTL8 polypeptide includes or comprises an amino acid sequence that is at least 50%, at least 55%, at least 60%, at least 65%, at least 70%, at least 75%, at least 80%, at least 85%, at least 90%, at least 95%, or at least 98% identical to amino acid residues 22-198 of SEQ ID NO:6 or SEQ ID NO:8. In some embodiments, a human ANGPTL8 polypeptide includes or comprises an amino acid sequence that is substantially identical or identical to amino acid residues 22-198 of SEQ ID NO:6 or SEQ ID NO:8.

In sonic embodiments, a human ANGPTL8 polypeptide is encoded by a sequence that is at least 50%, at least 55%, at least 60%, at least 65%, at least 70%, at least 75%, at least 80%, at least 85%, at least 90%, at least 95%, or at least 98% identical to SEQ ID NO:9. In some embodiments, a human ANGPTL8 polypeptide is encoded by a sequence that is substantially identical or identical to SEQ ID NO:9. In some embodiments, a human ANGPTL8 polypeptide is encoded by a sequence that is codon-optimized.

In some embodiments, a human ANGPTL8 polypeptide is a variant human ANGPTL8 polypeptide. In some embodiments, a variant human ANGPTL8 polypeptide is characterized by an R59W amino acid substitution. In some embodiments, a variant human ANGPTL8 polypeptide is characterized by a Q121X amino acid substitution. In some embodiments, a variant human ANGPTL8 polypeptide is characterized by or is associated with lower plasma low-density lipoprotein (LDL)-cholesterol and/or high-density lipoprotein (HDL)-cholesterol levels. In some embodiments, a variant human ANGPTL8 polypeptide is characterized by or is associated with augmented triglyceride levels. In some embodiments, a human ANGPTL8 polypeptide is encoded by a nucleic acid sequence placed at an endogenous non-human Angptl8 locus.

In some embodiments, an isolated non-human cell or tissue is provided, whose genome comprises an Angptl8 gene as described herein. In some embodiments, a cell is a lymphocyte. In some embodiments, a cell is selected from a B cell, dendritic cell, macrophage, monocyte, and a T cell. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, an immortalized cell made, generated or produced from an isolated non-human cell as described herein is provided.

In some embodiments, a non-human embryonic stem (ES) cell s provided, whose genome comprises an Angptl8 gene as described herein. In some embodiments, a non-human embryonic stem cell is a rodent embryonic stem cell. In some certain embodiments, a rodent embryonic stem cell is a mouse embryonic stem cell and is from a 129 strain, C57BL strain, or a mixture thereof. In some certain embodiments, a rodent embryonic stem cell is a mouse embryonic stem cell and is a mixture of 129 and C57BL strains.

In some embodiments, use of a non-human embryonic stem cell as described herein to make a non-human animal is provided. In some certain embodiments, a non-human embryonic stem cell is a mouse embryonic stem cell and is used to make a mouse comprising an Angptl8 gene (or locus) as described herein. In some certain embodiments, a non-human embryonic stem cell is a rat embryonic stem cell and is used to make a rat comprising an Angptl8 gene (or locus) as described herein.

In some embodiments, a non-human embryo comprising, made from, obtained from, or generated from a non-human embryonic stem cell as described herein is provided. In some certain embodiments, a non-human embryo is a rodent embryo; in some embodiments, a mouse embryo; in some embodiments, a rat embryo.

In some embodiments, use of a non-human embryo described herein to make a non-human animal is provided. In some certain embodiments, a non-human embryo is a mouse embryo and is used to make a mouse comprising an Angptl8 gene (or locus) as described herein. In some certain embodiments, a non-human embryo is a rat embryo and is used to make a rat comprising an Angptl8 gene (or locus) as described herein.

In some embodiments, a kit is provided, comprising an isolated non-human cell or tissue as described herein, an immortalized cell as described herein, non-human embryonic stem cell as described herein, a non-human embryo as described herein, or a non-human animal as described herein.

In some embodiments, a kit as described herein, for use in the manufacture and/or development of a drug (e.g., an antibody or antigen-binding fragment thereof) for therapy or diagnosis is provided.

In some embodiments, a kit as described herein, for use in the manufacture and/or development of a drug (e.g., an antibody or antigen-binding fragment thereof) for the treatment, prevention or amelioration of a disease, disorder or condition is provided.

In some embodiments, a transgene, nucleic acid construct, DNA construct, or targeting vector as described herein is provided. In some certain embodiments, a transgene, nucleic acid construct, DNA construct, or targeting vector comprises an Angptl8 gene (or locus), in whole or in part, as described herein. In some certain embodiments, a transgene, nucleic acid construct, DNA construct, or targeting vector comprises a DNA fragment that includes an Angptl8 gene (or locus), in whole or in part, as described herein. In some certain embodiments, a transgene, nucleic acid construct, DNA construct, or targeting vector comprises an Angptl8 gene (or locus) that comprises any one of SEQ ID NO:9, SEQ ID NO:10, SEQ ID NO:15, SEQ ID NO:16 and SEQ ID NO:17. In some certain embodiments, a transgene, nucleic acid construct, DNA construct, or targeting vector comprises an Angptl8 gene (or locus) that comprises SEQ ID NO:15, SEQ ID NO:16 and SEQ ID NO:17. In some certain embodiments, a transgene, nucleic acid construct, DNA construct, or targeting vector further comprises one or more selection markers. In some certain embodiments, a transgene, nucleic acid construct, DNA construct, or targeting vector further comprises one or more site-specific recombination sites (e.g., loxP, Frt, or combinations thereof). In some certain embodiments, a transgene, nucleic acid construct, DNA construct, or targeting vector is depicted in FIG. 3.

In some embodiments, use of a transgene, nucleic acid construct, DNA construct, or targeting vector as described herein to make a non-human embryonic stem cell, non-human cell, non-human embryo and/or non-human animal is provided.

In some embodiments, a method of making a non-human animal that expresses a human ANGPTL8 polypeptide from an endogenous Angptl8 gene is provided, the method comprising (a) placing a genomic fragment into an endogenous Angptl8 gene in a non-human embryonic stem cell, said genomic fragment comprising a nucleotide sequence that encodes a human ANGPTL8 polypeptide in whole or in part; (b) obtaining a non-human embryonic stem cell generated in (a); and, (c) creating a non-human animal using the non-human embryonic stem cell of (b).

In some embodiments, a nucleotide sequence comprises exons 1-4, in whole or in part, of a human ANGPTL8 gene. In some embodiments, a nucleotide sequence further comprises a 3' UTR of a human ANGPTL8 gene. In some embodiments, a nucleotide sequence encodes the mature form (i.e., without a signal peptide) of a human ANGPTL8 polypeptide. In some embodiments, a nucleotide sequence encodes amino acids 22-60, 77-134, 156-193 or 22-198 of a human ANGPTL8 polypeptide. In some embodiments, a nucleotide sequence comprises one or more selection markers. In some embodiments, a nucleotide sequence comprises one or more site-specific recombination sites. In some embodiments, a nucleotide sequence comprises a recombinase gene and a selection marker flanked by recombinase recognition sites, which recombinase recognition sites are oriented to direct an excision. In some embodiments, a recombinase gene is operably linked to a promoter that drives expression of the recombinase gene in differentiated cells and does not drive expression of the recombinase gene in undifferentiated cells. In some embodiments, a recombinase gene is operably linked to a promoter that is transcriptionally competent and developmentally regulated. In some embodiments, a promoter that is transcriptionally competent and developmentally regulated is or comprises SEQ ID NO:12, SEQ ID NO:13, or SEQ ID NO:14; in some certain embodiments, a promoter that is transcriptionally competent and developmentally regulated is or comprises SEQ ID NO:12. In sonic embodiments, a nucleotide sequence comprises one or more sequences that are codon-optimized for expression in a non-human animal. In some embodiments of a method of making a non-human animal that expresses a human ANGPTL8 polypeptide from an endogenous Angptl8 gene, the method further comprises a step of breeding the rodent generated in (c) so that a rodent homozygous for expressing a human ANGPTL8 polypeptide from an endogenous Angptl8 gene is created.

In some embodiments, a method of making a non-human animal whose genome comprises an Angptl8 gene that encodes a human ANGPTL8 polypeptide is provided, the method comprising modifying the genome of a non-human animal so that it comprises an Angptl8 gene that encodes a human ANGPTL8 polypeptide under the control of non-human animal Angptl8 regulatory sequences, thereby making said non-human animal.

In some embodiments, an Angptl8 gene is modified to include exons 1-4, in whole or in part, of a human ANGPTL8 gene. In some embodiments, an Angptl8 gene is modified to include exons 1-4, in whole or in part, of a human ANGPTL8 gene and modified to further include the 3' UTR of a human ANGPTL8 gene.

In some embodiments, a non-human animal obtainable by (made from, obtained from, or generated from) any one of the methods as described herein is provided.

In some embodiments, a method of assessing triglyceride-lowering efficacy of a drug targeting human ANGPTL8 is provided, the method comprising the steps of administering the drug to a non-human animal as described herein, and performing an assay to determine one or more triglyceride-lowering properties of the drug targeting human ANGPTL8.

In some embodiments, a method of assessing the pharmacokinetic properties of a drug targeting human ANGPTL8 is provided, the method comprising the steps of administering the drug to a non-human animal as described herein, and performing an assay to determine one or more pharmacokinetic properties of the drug targeting human ANGPTL8.

In some embodiments, a drug targeting human ANGPTL8 is an ANGPTL8 antagonist. In some embodiments, a drug targeting human ANGPTL8 is an ANGPTL8 agonist. In some embodiments, a drug targeting human ANGPTL8 is an anti-ANGPTL8 antibody. In some embodiments, a drug targeting human ANGPTL8 is administered to the rodent intravenously, intraperitoneally or subcutaneously.

In some embodiments, a non-human animal is provided, whose genome comprises an engineered Angptl8 gene that includes an endogenous portion that comprises the 5' UTR of an endogenous Angptl8 gene, and a human portion that comprises exons 1-4, in whole or in part, and the 3' UTR of a human ANGPTL8 gene, wherein the human portion is operably linked to an endogenous non-human Angptl8 ATG start codon and operably linked to an endogenous non-human Angptl8 promoter, and wherein the non-human animal expresses a human ANGPTL8 polypeptide in its serum. The engineered Angptl8 gene may also include or is linked to or followed by the 3' UTR of an endogenous Angptl8 gene, and/or a 3' sequence immediately downstream of the 3' UTR of an endogenous Angptl8 gene at an endogenous Angptl8 locus.

In some embodiments, a non-human animal model of hypertriglyceridemia is provided, which non-human animal expresses a human ANGPTL8 polypeptide as described herein.

In some embodiments, a non-human animal model of hypertriglyceridemia is provided, which non-human animal has a genome comprising an Angptl8 gene as described herein.

In some embodiments, a non-human animal or cell as described herein is provided, for use in the manufacture and/or development of a drug for therapy or diagnosis.

In some embodiments, use of a non-human animal or cell as described herein in the manufacture and/or development of a drug or vaccine for use in medicine, such as use as a medicament is provided.

In some embodiments, a non-human animal or cell as described herein is provided, for use in the manufacture of a medicament for the treatment, prevention or amelioration of a disease, disorder or condition. In some embodiments, a disease, disorder or condition is hypertriglyceridemia. In some embodiments, a disease, disorder or condition is a cardiovascular disease, disorder or condition.

In some embodiments, use of a non-human animal or cell as described herein in the manufacture of a medicament for the treatment of a disease, disorder or condition characterized by lipid dysfunction is provided.

In some embodiments, use of a non-human animal or cell as described herein in the manufacture and/or development of an antibody that binds human ANGPTL8 is provided.

In various embodiments, non-human Angptl8 regulatory elements include a non-human Angptl8 promoter; in some certain embodiments, an endogenous non-human Angptl8 promoter.

In various embodiments, an Angptl8 gene as described herein is a humanized Angptl8 gene.

In various embodiments, a human portion of an Angptl8 gene encodes an amino acid sequence that encodes, inter cilia, an amino acid sequence of a human ANGPTL8 polypeptide that is responsible for lipid binding or binding ANGPTL3.

In various embodiments, a human portion of an Angptl8 polypeptide comprises an amino acid sequence of the coiled-coil domain(s) or the N-terminal region of a human ANGPTL8 polypeptide.

In various embodiments, non-human animals as described herein express a human ANGPTL8 polypeptide that is detectable in the serum of the non-human animal. In various embodiments, non-human animals as described herein do not detectably express an endogenous Angptl8 polypeptide in the serum of the non-human animal.

In various embodiments, non-human animals as described herein comprise an Angptl8 gene (or locus) that includes SEQ ID NO:9 or SEQ ID NO:11. In various embodiments, non-human animals as described herein comprise an Angptl8 gene (or locus) that includes SEQ ID NO:15 and SEQ ID NO:18.

In various embodiments, a non-human animal as described herein is a rodent; in some embodiments, a mouse; in some embodiments, a rat. In some embodiments, a mouse as described herein is selected from the group consisting of a 129 strain, a BALB/C strain, a C57BL/6 strain, and a mixed 129xC57BL/6 strain; in sonic certain embodiments, a C57BL/6 strain.

As used in this application, the terms "about" and "approximately" are used as equivalents. Any numerals used in this application with or without about/approximately are meant to cover any normal fluctuations appreciated by one of ordinary skill in the relevant art.

BRIEF DESCRIPTION OF THE DRAWING

The Drawing included herein, which is composed of the following Figures, is for illustration purposes only and not for limitation.

FIG. 2 shows an alignment of representative amino acid sequences of human ANGPTL8 (hANGPTL8 SEQ ID NO:6), mouse Angptl8 (mAngptl8, SEQ ID NO:4), rat Angptl8 (rAngptl8, SEQ ID NO:2) and engineered Angptl8 (engAngptl8; SEQ NO:8). Asterisk (*) indicates identical amino acids; colon (:) indicates conservative substitutions; period (.) indicates semiconservative substitutions; blank indicates non-conservative substitutions; boxed amino acid residues indicate signal peptide.

FIGS. 8A-8K. For mRNA sequences, bold font indicates coding sequence and consecutive exons, where indicated, are separated by alternating underlined text; for engineered mRNA sequences, human sequences are contained within parentheses. For amino acid sequences, signal sequences are indicated by underlined font. 8A. *Rattus norvegicus* Angptl8 mRNA (SEQ ID NO:1, NCBI Reference Sequence NM_001271710.1). 8B. *Rattus norvegicus* Angptl8 amino acid (SEQ ID NO:2, NCBI Reference Sequence: NP_001258639.1). 8C. *Mus musculus* Angptl8 mRNA (SEQ ID NO: 3, NCBI Reference Sequence: NM_001080940.1). 8D. *Mus musculus* Angptl8 amino acid (SEQ ID NO:4, NCBI Reference Sequence: NP_001074409.1). 8E. *HOMO sapiens* ANGPTL8 mRNA (SEQ ID NO:5, NCBI Reference Sequence: NM_018687.6). 8F. *Homo sapiens* ANGPTL8 amino acid (SEQ ID NO:6, NCBI Reference Sequence: NP_061157.3). 8G. Exemplary Engineered Angptl8 mRNA (SEQ ID NO:7). 8H. Exemplary Engineered Angptl8 amino acid (SEQ ID NO:8). 8I. Exemplary synthetic DNA fragment for engineering a non-human Angptl8 gene (SEQ ID NO:9; ~2,383 bp including exons 1-4 and a 3' UTR of a human ANGPTL3 gene). 8J. Exemplary engineered Angptl8 allele including a selection cassette (SEQ ID NO:10; human sequence indicated in bold uppercase font, selection cassette sequence indicated in lowercase font, and mouse sequence indicated by regular uppercase font). 8K. Exemplary engineered Angptl8 allele after recombinase-mediated excision of a selection cassette (SEQ ID NO:11; human sequence indicated in bold uppercase font, sequence remaining after recombinase-mediated deletion of a selection cassette indicated in lowercase font, and mouse sequence indicated by regular uppercase font).

FIG. 9A. The nucleotide sequence across the upstream insertion point is shown which indicates endogenous mouse sequence (contained within the parentheses below with the ATG start codon in bold font) contiguous with human ANGPTL8 genomic sequence at the insertion point.

FIG. 9B. The nucleotide sequence across the 5' end of the self-deleting neomycin cassette is shown, which indicates human ANGPTL8 genomic sequence contiguous with cassette sequence (contained within the parentheses below with an XhoI site italicized and a loxP site in bold font) downstream of the insertion point.

FIG. 9C. The nucleotide sequence across the downstream insertion point at the 3' end of the self-deleting neomycin cassette is shown, which indicates cassette sequence (contained within the parentheses below with a loxP site in bold font, an I-CeuI recognition site underlined and an NheI recognition site italicized) contiguous with mouse Angptl8 genomic sequence.

FIG. 9D. The nucleotide sequence across the downstream insertion point after deletion of the neomycin cassette (77 bp remaining between a human ANGPTL8 3'UTR and a mouse Angptl8 3'UTR) is shown, which indicates human and mouse genomic sequence juxtaposed with remaining cassette sequence (contained within the parentheses below with XhoI and NheI recognition sites italicized, a loxP site in bold, and an I-CeuI restriction site underlined).

DEFINITIONS

Figure 1:
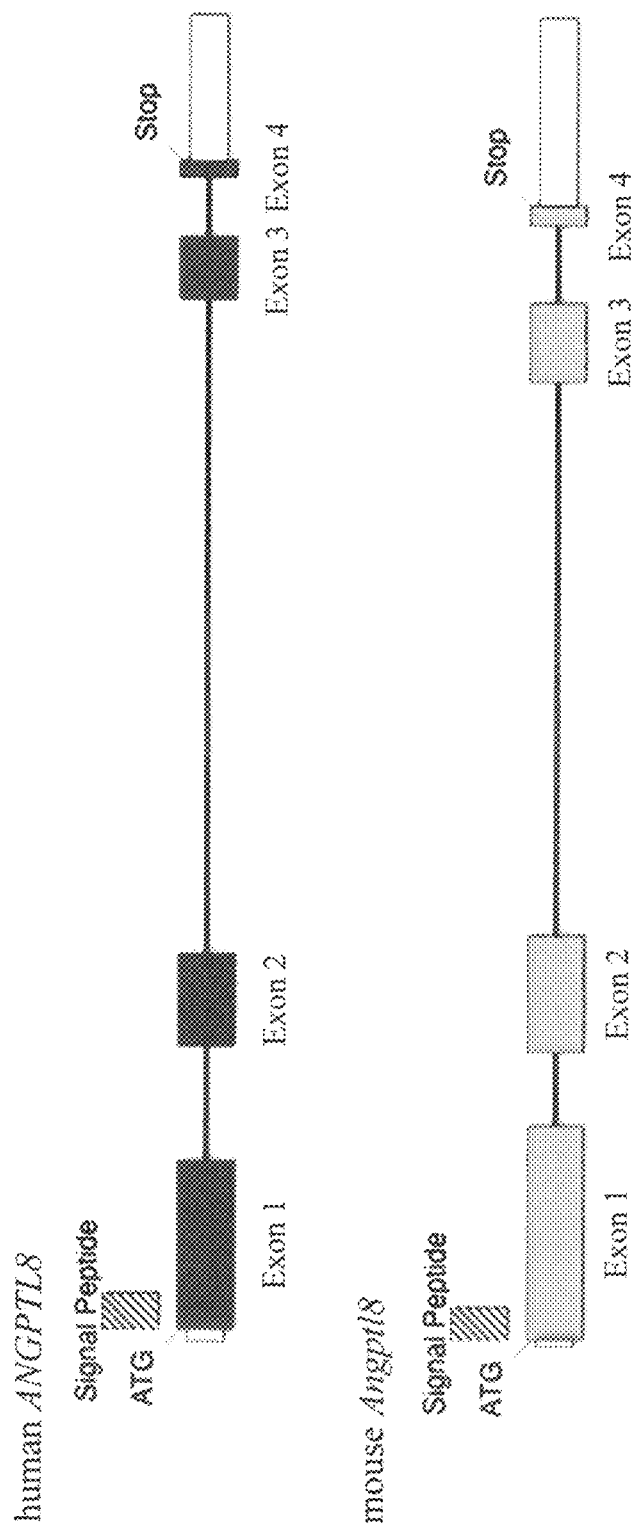
FIG. 1 shows a representative diagram, not to scale, of the genomic organization of non-human (e.g., mouse) and human Angiopoietin-like protein 8 (ANGPTL8) genes. Exons are numbered below each exon. Untranslated regions (open boxes) are also indicated for each gene. Relative portions of coding sequence that encode signal peptides are indicated above exon 1 for each gene.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All patent and non-patent publications mentioned herein are hereby incorporated by reference.

Approximately: as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: as used herein, refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Comparable: as used herein, refers to two or more agents, entities, situations, sets of conditions, etc. that may not be identical to one another but that are sufficiently similar to permit comparison between them so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Conservative: as used herein, refers to instances when describing a conservative amino acid substitution, including a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445. In some embodiments, a substitution is a moderately conservative substitution wherein the substitution has a nonnegative value in the PAM250 log-likelihood matrix.

Control: as used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may refer to a "control animal". A "control animal" may have a modification as described herein, a modification that is different as described herein, or no modification (i.e., a wild-type animal). In one experiment, the "test" (i.e., the variable being tested) is applied. In the second experiment, the "control" (i.e., the variable being tested) is not applied. In some embodiments, a control is a historical control (i.e., of a test or assay performed previously, or an amount or result that is previously known). In some embodiments, a control is or comprises a printed or otherwise saved record. A control may be a positive control or a negative control.

Disruption: as used herein, refers to the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

Determining, measuring, evaluating, assessing, assaying and analyzing: are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Endogenous locus or endogenous gene: as used herein, refers to a genetic locus found in a parent or reference organism prior to introduction of an alteration, disruption, deletion, insertion, modification, replacement, or substitution as described herein. In some embodiments, the endogenous locus has a sequence found in nature. In some embodiments, the endogenous locus is a wild-type locus. In some embodiments, the reference organism is a wild-type organism. In some embodiments, the reference organism is an engineered organism. In some embodiments, the reference organism is a laboratory-bred organism (whether wild-type or engineered).

Endogenous promoter: as used herein, refers to a promoter that is naturally associated, e.g., in a wild-type organism, with an endogenous gene.

Engineered: as used herein refers, in general, to the aspect of having been manipulated by the hand of man. For example, in some embodiments, a polynucleotide may be considered to be "engineered" when two or more sequences that are not linked together in that order in nature are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively or additionally, in sonic embodiments, "engineering" may involve use of in vitro chemical synthesis methodologies and/or recombinant nucleic acid technologies such as, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation [e.g., electroporation, lipofection, etc.]) are well known in the art and described in various general and more specific references that are cited and/or discussed throughout the present specification. See e.g., Sambrook et al., Molecular Cloning: A Laboratory Manual (2d ed., Cold Spring Harbor Laboratory Press, Cold Spring Harbor, N.Y., 1989).

Gene: as used herein, refers to a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity we note that, as used in the present application, the term "gene" generally refers to a portion of a nucleic acid that encodes a polypeptide; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

Heterologous: as used herein, refers to an agent or entity from a different source. For example, when used in reference to a polypeptide, gene, or gene product present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

Host cell: as used herein, refers to a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, a host cell is or comprises a prokaryotic or eukaryotic cell. In general, a host cell is any cell that is suitable for receiving and/or producing a heterologous nucleic acid or polypeptide, regardless of the Kingdom of life to which the cell is designated. Exemplary cells include those of prokaryotes and eukaryotes (single-cell or multiple-cell), bacterial cells (e.g., strains of *E. coli*, *Bacillus* spp., *Streptomyces* spp., etc.), mycobacteria cells, fungal cells, yeast cells (e.g., *S. cerevisiae*, *S. pombe*, *P. pastoris*, *P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

Humanized: is used herein in accordance with its art-understood meaning to refer to nucleic acids or polypeptides whose structures (i.e., nucleotide or amino acid sequences) include portions that correspond substantially or identically with structures of a particular gene or polypeptide found in nature in a non-human animal, and also include portions that differ from that found in the relevant particular non-human gene or protein and instead correspond more closely with comparable structures found in a corresponding human gene or polypeptide. In some embodiments, a "humanized" gene is one that encodes a polypeptide having substantially the amino acid sequence as that of a human polypeptide (e.g., a human protein or portion thereof—e.g., characteristic portion thereof). For example, in the case of a membrane receptor, a "humanized" gene may encode a polypeptide having an extracellular portion, in whole or in part, having an amino acid sequence as that of a human extracellular portion and the remaining sequence as that of a non-human (e.g., mouse) polypeptide. In the case of a secreted polypeptide, a "humanized" gene may encode a polypeptide having a mature peptide, in whole or in part, having a sequence as that of a human mature peptide and the signal sequence as that of a non-human (e.g., mouse) peptide. In some embodiments, a humanized gene comprises at least a portion of a DNA sequence of a human gene. In some embodiments, a humanized gene comprises an entire DNA sequence of a human gene or the DNA sequence of a human gene that encodes a mature peptide or polypeptide corresponding to a mature human peptide or polypeptide. In some embodiments, a humanized polypeptide comprises a sequence having a portion that appears in a human polypeptide. In some embodiments, a humanized polypeptide comprises an entire sequence of a human polypeptide and is expressed from an endogenous locus of a non-human animal that corresponds to the homolog or ortholog of the human gene.

Identity: as used herein in connection with a comparison of sequences, refers to identity as determined by a number of different algorithms known in the art that can be used to measure nucleotide and/or amino acid sequence identity. In some embodiments, identities as described herein are determined using a ClustalW v.1.83 (slow) alignment employing an open gap penalty of 10.0, an extend gap penalty of 0.1, and using a Gonnet similarity matrix (MACVECTOR™ 10.0.2, MacVector Inc., 2008).

In vitro: as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature, Thus, for instance, in some embodiments, a polypeptide that is chemically synthesized or is synthesized in a different cellular system from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

Locus or Loci: as used herein, includes a specific location(s) of a gene (or significant sequence), DNA sequence, polypeptide-encoding sequence, or position on a chromosome of the genome of an organism. For example, an "Angptl8 locus" may refer to the specific location of an Angptl8 gene, Angptl8 DNA sequence, Angptl8-encoding sequence, or Angptl8 position on a chromosome of the genome of an organism that has been identified as to where such a sequence resides. An "Angptl8 locus" may comprise a regulatory element of an Angptl8 gene, including, but not limited to, an enhancer, a promoter, 5' and/or 3' UTR, or a combination thereof. Those of ordinary skill in the art will appreciate that chromosomes may, in some embodiments, contain hundreds or even thousands of genes and demonstrate physical co-localization of similar genetic loci when comparing between different species. Such genetic loci may be described as having shared synteny.

Non-human animal: as used herein, refers to any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human animal as described herein is a mammal. In some embodiments, a non-human mammal is a primate, a goat, a sheep, a pig, a dog, a cow, or a rodent. In some embodiments, a non-human animal as described herein is a small mammal, e.g., of the superfamily Dipodoidea or Muroidea. In some embodiments, a genetically modified animal as described herein is a rodent. In some embodiments, a rodent as described herein is selected from a mouse, a rat, and a hamster. In some embodiments, a rodent as described herein is selected from the superfamily Muroidea. In some embodiments, a genetically modified animal as described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In some certain embodiments, a genetically modified rodent as described herein is selected from a true mouse or rat (family Muridae), a gerbil, a spiny mouse, and a crested rat. In some certain embodiments, a genetically modified mouse as described herein is from a member of the family Muridae. In some embodiment, a non-human animal as described herein is a rodent. In some certain embodiments, a rodent as described herein is selected from a mouse and a rat. In some embodiments, a non-human animal as described herein is a mouse.

In some embodiments, a non-human animal as described herein is a rodent, that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse as described herein is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotech. 29(5):1024-1028, 1030, 1032). In some certain embodiments, a genetically modified mouse as described herein is a mix of an aforementioned 129 strain and an aforementioned C57BL/6 strain. In some certain embodiments, a mouse as described herein is a mix of aforementioned 129 strains, or a mix of aforementioned BL/6 strains. In sonic certain embodiments, a 129 strain of the mix as described herein is a 129S6 (129/SvEvTac) strain. In some embodiments, a mouse as described herein is a BALB strain, e.g., BALB/c strain. In some embodiments, a mouse as described herein is a mix of a BALB strain and another aforementioned strain.

In some embodiments, a non-human animal as described herein is a rat. In some certain embodiments, a rat as described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Nucleic acid: as used herein, in its broadest sense, refers to any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In sonic embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

Operably linked: as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence", as used herein, refers to polynucleotide sequences, which are necessary to effect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Patient or subject: as used herein, refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a non-human animal. In some embodiments, a patient or subject (e.g., a non-human animal patient) may have a modification as described herein, a modification that is different as described herein or no modification (i.e., a wild-type non-human animal patient). In some embodiments, a non-human animal is suffering from or susceptible to one or more disorders or conditions. In some embodiments, a non-human animal displays one or more symptoms of a disease, disorder or condition. In sonic embodiments, a non-human animal has been diagnosed with one or more diseases, disorders or conditions.

Polypeptide: as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and or produced through action of the hand of man.

Promoter or Promoter sequence: as used herein, refers to a DNA regulatory region capable of being bound by an RNA polymerase in a cell (e.g., directly or through other promoter-bound polypeptides or substances) and initiating transcription of a coding sequence. A promoter sequence is, in general, bound at its 3' terminus by the transcription initiation site and extends upstream (5' direction) to include the minimum number of bases or elements necessary to initiate transcription at any level. The promoter may be operably associated with or operably linked to expression control sequences, including enhancer and repressor sequences or with a nucleic acid of interest that is to be expressed. In some embodiments, a promoter may be inducible. In sonic embodiments, an inducible promoter may be unidirectional or bi-directional. In some embodiments, a promoter may be a constitutive promoter. In some embodiments, a promoter can be a hybrid promoter, in which the sequence containing a transcriptional regulatory region is obtained from one source and the sequence containing a transcription initiation region is obtained from a second source. Systems for linking control elements to coding sequences within a transgene are well known in the art. For example, general molecular biological and recombinant DNA techniques are described in Principles of Gene Manipulation: An Introduction to Genetic Manipulation, $5^{th}$ Ed., ed. By Old, R. W. and S. B. Primrose, Blackwell Science, Inc., 1994; Molecular Cloning: A Laboratory Manual, $2^{nd}$ Ed., ed. by Sambrook, J. et al., Cold Spring Harbor Laboratory Press: 1989.

Recombinant: as used herein, is intended to refer to polypeptides that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997, TIB Tech. 15:62-70; Azzazy H., and Highsmith W. E., 2002, Clin. Biochem. 35:425-45; Gavilondo J. V., and Larrick J. W., 2002, Bio-Tech. 29:128-45; Hoogenboom H., and Chames P., 2000, Immunology Today 21:371-8), antibodies isolated from an animal (e.g., a mouse) that is transgenic for human immunoglobulin genes (see e.g., Taylor, L. D. et al., 1992, Nucl. Acids Res. 20:6287-95; Kellermann S-A., and Green L. L., 2002, Curr. Opin. Biotechnol. 13:593-7; Little M. et al., 2000, Immunol. Today 21:364-370; Murphy, A. J. et al., 2014, Proc. Natl. Acad. Sci. U.S.A. 111(14):5153-8) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silica. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

Replacement: as used herein, refers to a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice acceptor site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, a replacement nucleic acid sequence is or comprises an engineered nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a polypeptide that has a similar function as a polypeptide encoded by the endogenous sequence (e.g., the endogenous genomic sequence encodes a Angptl8 polypeptide, and the DNA fragment encodes one or more human ANGPTL8 polypeptides, in whole or in part). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

Reference: as used herein, describes a standard or control agent, cohort, individual, population, sample, sequence or value against which an agent, animal, cohort, individual, population, sample, sequence or value of interest is compared. In some embodiments, a reference agent, cohort, individual, population, sample, sequence or value is tested and/or determined substantially simultaneously with the testing or determination of the agent, cohort, individual, population, sample, sequence or value of interest. In some embodiments, a reference agent, cohort, individual, population, sample, sequence or value is a historical reference, optionally embodied in a tangible medium. In some embodiments, a reference may refer to a control. As used herein, a "reference" may refer to a "reference animal". A "reference animal" may have a modification as described herein, a modification that is different as described herein or no modification (i.e., a wild-type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

Substantially: as used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: as used herein, refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, Basic local alignment search tool, J. Mol. Biol., 215(3): 403-410; Altschul et al., 1996, Methods Enzymol. 266:160-80; Altschul et al., 1997, Nucleic Acids Res. 25:3389-3402; Baxevanis et al., 1998 Bioinformatics: A Practical Guide to the Analysis of Genes and Proteins, Wiley; and Misener et al. (eds.) (1999) Bioinformatics Methods and Protocols (Methods in Molecular Biology, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

Substantial identity: as used herein, refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, Basic local alignment search tool, J. Mol. Biol., 215(3): 403-410; Altschul et al., 1996, Methods Enzymol. 266:160-80; Altschul et al., 1997, Nucleic Acids Res. 25:3389-3402; Baxevanis et al., 1998, Bioinformatics: A Practical Guide to the Analysis of Genes and Proteins, Wiley; Misener et al., (eds.) (1999) Bioinformatics Methods and Protocols (Methods in Molecular Biology, Vol. 132), Humana Press. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

Targeting vector or targeting construct: as used herein, refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP and/or Frt sites) are also included. In some embodiments, a targeting construct further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct further comprises a gene of interest in whole or in part, wherein the gene of interest is a heterologous gene that encodes a polypeptide, in whole or in part, that has a similar function as a polypeptide encoded by an endogenous sequence. In some embodiments, a targeting construct further comprises a humanized gene of interest, in whole or in part, wherein the humanized gene of interest encodes a polypeptide, in whole or in part, that has a similar function as a polypeptide encoded by the endogenous sequence. In some embodiments, a targeting construct further comprises an engineered gene of interest, in whole or in part, wherein the engineered gene of interest encodes a polypeptide, in whole or in part, that has a similar function as a polypeptide encoded by an endogenous sequence.

Variant: as used herein, refers to an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a "variant" has 10, 9, 8, 7, 6, 5, 4, 3, 2, or 1 substituted residue as compared with a parent. Often, a "variant" has a very small number (e.g., fewer than 5, 4, 3, or 1) of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

Vector: as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors".

Wild-type: as used herein, has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention provides, among other things, improved and/or engineered non-human animals having heterologous genetic material encoding an Angiopoietin-like protein 8 (ANGPTL8) for determining the therapeutic efficacy of ANGPTL8 modulators (e.g., an anti-ANGPTL8 antibodies) for the treatment of metabolic disorders, and assays measuring lipid (e.g., triglyceride) metabolism, glucose homeostasis, various effects on body weight, composition and energy expenditure. It is contemplated that such non-human animals provide an improvement in determining the therapeutic efficacy of ANGPTL8 modulators and their potential for ANGPTL8 blockade. Therefore, the present invention is particularly useful for the development of anti-ANGPTL8 therapies for the treatment of diseases, disorders or conditions that result from or are characterized by various metabolic disorders, including triglyceride dysfunction, glucose intolerance and dyslipidemia (Zhang and Abou-Samra, Cardiovascular Diabetology 2014, 13:133). In particular, the present invention encompasses the engineering of a non-human (e.g., murine) Angptl8 gene resulting in expression of a human ANGPTL8 polypeptide in the serum of the non-human animal. Such non-human animals have the capacity to provide an in vivo animal model for determining the efficacy of anti-ANGPTL8 therapeutics in the treatment of metabolic disorders and/or cardiovascular diseases, disorders and/or conditions. In some embodiments, non-human animals as described herein demonstrate augmented triglyceride levels as compared to wild-type non-human animals. In some embodiments, non-human animals as described herein provide an in vivo animal model for lipoprotein metabolism. In some embodiments, non-human animals as described herein provide an in vivo animal model for hypertriglyceridemia.

In some embodiments, Angptl8 polypeptides expressed (or secreted) by a non-human animal as described herein comprise a sequence corresponding to amino acids 22-60, 77-134, 156-193 or 22-198 of a human ANGPTL8 polypeptide. In some embodiments, Angptl8 polypeptides encoded by genetic material within the genome of non-human animals described herein comprise a sequence corresponding to the signal peptide a murine Angptl8 polypeptide. In some embodiments, non-human animals as described herein comprise, at an endogenous Angptl8 locus, an Angptl8 gene that contains genetic material from the non-human animal and a heterologous species (e.g., a human). In some embodiments, non-human animals as described herein comprise an engineered Angptl8 gene, wherein the engineered Angptl8 gene comprises exons 1-4 of a human ANGPTL8 gene, in whole or in part. In some embodiments, non-human animals as described herein comprise an engineered Angptl8 gene, wherein the engineered Angptl8 gene comprises the coding portion of exon 1 and exons 2-4 of a human ANGPTL8 gene. In some embodiments, non-human animals as described herein comprise an engineered Angptl8 gene, wherein the engineered Angptl8 gene comprises the coding portion of exon 1 (or the coding portion of exon 1 excluding the start codon), exon 2, exon 3 and exon 4 (which includes the 3' UTR) of a human ANGPTL8 gene. In some certain embodiments, non-human animals as described herein comprise an engineered Angptl8 gene, wherein the engineered Angptl8 gene comprises ~2,383 bp of a human ANGPTL8 gene corresponding to the coding portion of exon 1 beginning from immediately after the start codon through exon 4 including the 3' UTR (e.g., ~256 bp) of a human ANGPTL8 gene. In some embodiments, non-human animals as described herein comprise an engineered Angptl8 gene at an endogenous Angptl8 locus, wherein the engineered Angptl8 gene comprises the 5' UTR of an endogenous Angptl8 gene, the coding portion of exon 1, exon 2, exon 3 and exon 4 (which includes the 3' UTR) of a human ANGPTL8 gene, operably linked to an endogenous Angptl8 promoter; and in some embodiments, in creating such an engineered Angptl8 gene, the coding portion of exon 1, exons 2-3, and the coding portion of exon 4 of the endogenous Angptl8 gene at said endogenous Angptl8 locus have been deleted. In various embodiments, non-human animals as described herein do not detectably express an endogenous Angptl8 polypeptide, in whole or in part.

Various aspects of the invention are described in detail in the following sections. The use of sections is not meant to limit the invention. Each section can apply to any aspect of the invention. In this application, the use of "or" means "and/or" unless stated otherwise.

Angiopoietin-Like Protein 8 (ANGPTL8)

ANGPTL8 (also referred to as TD26, RIFL, Lipasin, C19orf80 and Betatrophin) is a newly recognized ANGPTL family member that has been implicated in both triglyceride and glucose metabolism. Phylogenetic analysis has revealed that ANGPTL8 is closely related to ANGPTL3 and ANGPTL4 (Fu, Z. et. al., 2013, Biochem. Biophys. Res. Commun. 430:1126-31; Quagliarini F. et al; 2012, PNAS 109:19751-19756). ANGPTL8 is a secreted polypeptide expressed primarily in liver and adipose tissue, and, unlike related family members ANGPTL3 and ANGPTL4, lacks a C-terminal fibrinogen-like domain, but contains an N-terminal coiled-coil domain, much like other ANGPTL family members (Mattijssen F., and Kersten S, Biochim Biophys Acta 1821, 2012:782-789).

Hepatic overexpression of ANGPTL8 is associated with hypertriglyceridemia, whereas inactivation of Angptl8 causes a reduction in plasma triglyceride levels (Quagliarini, F. et. al., 2012, Proc. Natl. Acad. Sci. USA 109(48):19751-6; Wang, Y. et. al., 2013, Proc. Natl. Acad. Sci. USA 110: 16109-14). Despite reports that ANGPTL8 is involved in the regulation of lipids, the responsible mechanism is still under debate. To give but one example, one mechanism reasons that ANGPTL8 inhibits lipoprotein lipase activity, resulting in reduced triglyceride hydrolysis and clearance (Zhang, R. et. al., 2012, Biochem. Biophys. Res. Commun 424:786-92). ANGPTL8 has also been reported to play a role in beta cell proliferation and beta cell mass in mice where insulin resistance was induced by insulin receptor antagonist 5961 (Yi, P. et. al. 2013, Cell 153:747-58). However, subsequent studies have revealed that ANGPTL8 is not required for beta cell function or the beta cell growth response to insulin resistance. Further, overexpression of ANGPTL8 does not increase beta cell area or improve glycemic control (Gusarova, V. et. at, 2014, Cell 159:691-6). Since hepatic overexpression of ANGPTL8 is associated with hypertriglyceridemia and inactivation of Angptl8 results in a reduction in plasma triglyceride levels, an inhibitor or antagonist of ANGPTL8 may prove effective in treating a disease characterized, in part, by elevated triglyceride levels, such as, but not limited to, hypertriglyceridemia. According to one report using wild-type mice, a monoclonal antibody to lipasin decreased serum triglyceride levels when injected intraperitoneally (Zhang, R., 2015, Endocrine Society's 97th Annual Meeting, Presentation No. OR13-6, March 5-8, San Diego, Calif.).

A more thorough and detailed understanding of ANGPTL8-mediated functions and the ANGPTL8 pathway in lipid metabolism, glucose homeostasis, effect on body weight, body composition, energy expenditure and cardiovascular function, is needed to develop practical targeted therapies for future treatment of human patients suffering from hypertriglyceridemia and other diseases, disorders or conditions characterized by elevated triglyceride and lipid levels.

ANGPTL8 Sequences

ANGPTL8 (also referred to as TD26, RIFL, Lipasin, C19orf80 and Betatrophin) is a member of the Angiopoietin family of proteins. "ANGPTL8", as used herein, refers to a human ANGPTL8 polypeptide, and in some embodiments, a human ANGPTL8 polypeptide, without a signal peptide (e.g., a polypeptide comprising the amino acid sequence as set forth in 22-198 of SEQ ID NO:6). Exemplary human ANGPTL8 amino acid (including the signal peptide) and mRNA sequences can be found in GenBank accession numbers NP_061157.3 (SEQ ID NO:6) and NM_018687.6 (SEQ ID NO:5), respectively (see FIGS. 8D and 8E). The N-terminal coiled-coil domains of human ANGPTL8 spans amino acid residues ~77-134 and 156-193 of SEQ ID NO:6.

Exemplary rodent (e.g., rat and mouse), human and engineered Angptl8 sequences are set forth in FIGS. 8A-8H. An exemplary synthetic DNA fragment for engineering a non-human Angptl8 gene as described herein is also set forth in FIG. 8I. For mRNA sequences, bold font indicates coding sequence and consecutive exons, where indicated, are separated by alternating underlined text; for engineered mRNA sequences, human sequences are contained within parentheses. For amino acid sequences, signal sequences are indicated by underlined font.

DNA Constructs and Production of Non-Human Animals Having a Humanized ANGPTL8 Gene Typically, a polynucleotide molecule containing an Angptl8 gene (e.g., a heterologous or engineered Angptl8 gene), in whole or in part, is inserted into a vector, preferably a DNA vector, in order to replicate the polynucleotide molecule in a suitable host cell.

Depending on size, an Angptl8 gene or Angptl8-encoding sequence as can be cloned directly from cDNA sources available from commercial suppliers or designed in silico based on published sequences available from GenBank. Alternatively, bacterial artificial chromosome (BAC) libraries can provide heterologous Angptl8 sequences from genes of interest (e.g., a heterologous Angptl8 gene). BAC libraries contain an average insert size of 100-150 kb and are capable of harboring inserts as large as 300 kb (Shizuya, H. et al., 1992, Proc. Natl. Acad. Sci., U.S.A. 89:8794-7; Swiatek, P. J. and T. Gridley, 1993, Genes Dev. 7:2071-84; Kim, U. J. et al., 1996, Genomics 34:213-8; herein incorporated by reference). For example, human and mouse genomic BAC libraries have been constructed and are commercially available (e.g., Invitrogen, Carlsbad Calif.). Genomic BAC libraries can also serve as a source of heterologous Angptl8 sequences as well as transcriptional control regions.

Alternatively, heterologous Angptl8 sequences may be isolated, cloned and/or transferred from yeast artificial chromosomes (YACs). An entire heterologous gene or locus can be cloned and contained within one or a few YACs. If multiple YACs are employed and contain regions of overlapping homology, they can be recombined within yeast host strains to produce a single construct representing the entire locus. YAC arms can be additionally modified with mammalian selection cassettes by retrofitting to assist in introducing the constructs into embryonic stems cells or embryos by methods known in the art and/or described herein.

Exemplary mRNA and amino acid sequences for use in constructing a humanized Angptl8 gene in a non-human animal are provided above. Other heterologous Angptl8 sequences can also be found in the GenBank database or other sequence databases known in the art.

DNA constructs containing Angptl8 sequences as described herein, in some embodiments, comprise human ANGPTL8 genomic (or cDNA) sequences encoding at least about amino acids 22-60, 77-134, 156-193 or 22-198 of a human ANGPTL8 polypeptide operably linked to non-human regulatory sequences (e.g., a rodent promoter) for expression in a transgenic non-human animal. In some embodiments, DNA constructs containing Angptl8 sequences as described herein comprise human ANGPTL8 genomic (or cDNA) sequences encoding at least about amino acids 22-60, 77-134, 156-193 or 22-198 of a human ANGPTL8 polypeptide operably linked to a non-human Angptl8 promoter and one or more non-human Angptl8 untranslated regions (e.g., 5' and/or 3' UTRs). Human and/or non-human Angptl8 sequences included in DNA constructs described herein may be identical or substantially identical with human and/or non-human Angptl8 sequences found in nature (e.g., genomic), artificial (e.g., synthetic) or may be engineered by the hand of man. In some embodiments, Angptl8 sequences are synthetic in origin, and include a sequence or sequences that are found in a human ANGPTL8 gene found in nature. For example, a DNA construct can include synthetic DNA that corresponds to exons 1-4 of a human ANGPTL8 gene, and that encodes at least about amino acids 22-60, 77-134, 156-193 or 22-198 of a human ANGPTL8 polypeptide, operably linked to non-human Angptl8 regulatory (e.g., promoter) and non-coding sequences (e.g., one or more non-human UTRs) so that a Angptl8 polypeptide having a sequence that is all or substantially all human is encoded by the resulting DNA construct. Alternatively, a DNA construct can include synthetic DNA that corresponds to the genetic material that encodes a functional portion of a human ANGPTL8 polypeptide (e.g., one or more coiled-coil domains, an N-terminal region) operably linked to non-human Angptl8 regulatory (e.g., promoter) and coding sequences (e.g., one or more non-human exons) so that Angptl8 polypeptide having human and non-human portions is encoded by the resulting DNA construct. In some embodiments, Angptl8 sequences comprise a sequence naturally associated with a heterologous Angptl8 gene (e.g., a human ANGPTL8 gene). In some embodiments, Angptl8 sequences comprise a sequence that is not naturally associated with a heterologous Angptl8 gene. In some embodiments, Angptl8 sequences comprise a sequence that is optimized for expression in a non-human animal. In some embodiments, heterologous Angptl8 sequences operably linked to non-human Angptl8 sequences each encode a portion of an Angptl8 polypeptide that appears in separate polypeptides in nature. If additional sequences are useful in optimizing expression of heterologous Angptl8 sequences, such sequences can be cloned using existing sequences as probes. Additional sequences necessary for maximizing expression of a heterologous Angptl8 gene or heterologous Angptl8-encoding sequence can be obtained from genomic sequences or other sources depending on the desired outcome.

DNA constructs can be prepared using methods known in the art. For example, a DNA construct can be prepared as part of a larger plasmid. Such preparation allows the cloning and selection of the correct constructions in an efficient manner as is known in the art. DNA fragments containing one or more nucleotide coding sequences as described herein can be located between convenient restriction sites on the plasmid so that they can be easily isolated from the remaining plasmid sequences for incorporation into the desired animal.

Various methods employed in preparation of plasmids and host organisms containing them are known in the art. For other suitable expression systems for both prokaryotic and eukaryotic cells, as well as general recombinant procedures, see Principles of Gene Manipulation: An Introduction to Genetic Manipulation, 5$^{th}$ Ed., ed. By Old, R. W. and S. B. Primrose, Blackwell Science, Inc., 1994; Molecular Cloning: A Laboratory Manual, 2$^{nd}$ Ed., ed. by Sambrook, J. et al., Cold Spring Harbor Laboratory Press: 1989.

Non-human animals are provided that express human ANGPTL8 polypeptides, in whole or in part, in the serum of the non-human animals resulting from a genetic modification of an endogenous locus (e.g., an Angptl8 locus) of the non-human animal that encodes an Angptl8 polypeptide. Suitable examples described herein include rodents, in particular, mice.

A humanized Angptl8 gene, in some embodiments, comprises genetic material from a heterologous species (e.g., humans), wherein the humanized Angptl8 gene encodes an Angptl8 polypeptide that comprises the encoded portion of the genetic material from the heterologous species. In some embodiments, a humanized Angptl8 gene as described herein comprises genomic DNA of a heterologous species that encodes an Angptl8 polypeptide that is expressed in the serum of the non-human animal, wherein the Angptl8 polypeptide has a sequence that is all or substantially all human. Non-human animals, embryos, cells and targeting constructs for making non-human animals, non-human embryos, and cells containing said humanized Angptl8 gene are also provided.

In some embodiments, an endogenous Angptl8 gene is deleted. In some embodiments, an endogenous Angptl8 gene is altered, wherein a portion of the endogenous Angptl8 gene is replaced with a heterologous sequence (e.g., a human ANGPTL8 sequence, in whole or in part). In some embodiments, all or substantially all of an endogenous Angptl8 gene is replaced with a heterologous gene (e.g., a human ANGPTL8 gene, in whole or in part) In some embodiments, a portion of a heterologous Angptl8 gene is inserted into an endogenous non-human Angptl8 gene at an endogenous Angptl8 locus. In some embodiments, the heterologous gene is a human gene. In some embodiments, the modification or humanization is made to one of the two copies of an endogenous Angptl8 gene, giving rise to a non-human animal that is heterozygous with respect to the humanized Angptl8 gene. In other embodiments, a non-human animal is provided that is homozygous for a humanized Angptl8 gene.

In some embodiments, a non-human animal as described herein contains a human ANGPTL8 gene, in whole or in part, at an endogenous non-human Angptl8 locus. In some embodiments, a non-human animal as described herein contains a human ANGPTL8 gene, in whole or in part, at a location other than an endogenous non-human Angptl8 locus. Thus, non-human animals as described herein can be characterized as having a humanized or heterologous Angptl8 gene. The replaced, inserted, modified or altered Angptl8 gene at the endogenous Angptl8 locus or a polypeptide expressed from such gene can be detected using a variety of methods including, for example, PCR, Western blot, Southern blot, restriction fragment length polymorphism (RFLP), or a gain or loss of allele assay. A humanized or heterologous Angptl8 gene randomly inserted into the non-human animal genome may be detected by the same or similar means. In some embodiments, a non-human animal as described herein is heterozygous with respect to a humanized or heterologous Angptl8 gene as described herein.

In various embodiments, a humanized Angptl8 gene as described herein includes an Angptl8 gene that has the coding portion of exon 1 (beginning from or immediately after the ATG start codon to the 3' end of exon 1), and exons 2-4, of a human ANGPTL8 gene.

In various embodiments, a humanized Angptl8 gene as described herein includes an Angptl8 gene that has a first, second, third and fourth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a first, second, third and fourth exon that appear in SEQ ID NO:5 or SEQ ID NO:7.

In various embodiments, a humanized Angptl8 gene as described herein includes a Angptl8 gene that has a first, second, third and fourth exon each having a sequence that is substantially identical or identical to a first, second, third and fourth exon that appear in SEQ ID NO:5 or SEQ ID NO:7.

In various embodiments, a humanized Angptl8 gene as described herein comprises a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:10 or SEQ ID NO:11.

In various embodiments, a humanized Angptl8 gene as described herein comprises a sequence that is substantially identical or identical to SEQ ID NO:10 or SEQ TD NO:11.

In various embodiments, a humanized Angptl8 gene as described herein is or comprises SEQ NO:10 or SEQ ID NO:11.

In various embodiments, a humanized Angptl8 gene as described herein comprises a 5' untranslated region having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a 5' untranslated region that appears in SEQ ID NO:1 or SEQ 1D NO:3, and/or a 3' untranslated region having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a 3' untranslated region that appears in SEQ ID NO:1 or SEQ ID NO:3.

In various embodiments, a humanized Angptl8 gene as described herein comprises a 5' untranslated region having a sequence that is substantially identical or identical to a 5' untranslated region that appears in SEQ ID NO:1 or SEQ ID NO:3, and/or a 3' untranslated region having a sequence that is substantially identical or identical to a 3' untranslated region that appears in SEQ ID NO:1 or SEQ ID NO:3.

In various embodiments, a humanized Angptl8 gene as described herein comprises a 5' untranslated region having a sequence that is substantially identical or identical to the 5' untranslated region of an endogenous non-human Angptl8 gene, and/or a 3' untranslated region having a sequence that is substantially identical or identical to the 3' untranslated region of a human ANGPTL8 gene. In particular embodiments, a humanized Angptl8 gene as described herein comprises a 5' untranslated region having a sequence that is substantially identical or identical to a 5' untranslated region that appears in SEQ ID NO:1 or SEQ ID NO:3, and/or a 3' untranslated region having a sequence that is substantially identical or identical to the 3' untranslated region that appears in SEQ ID NO:5 or SEQ ID NO:7.

In specific embodiments, a humanized Angptl8 gene as described herein comprises a 5' untranslated region of an endogenous non-human (e.g., mouse or rat) Angptl8 gene, the coding portion of exon 1 of a human ANGPTL8 gene, and exons 2-4 of a human ANGPTL8 gene, which include the 3' UTR of the human ANGPTL8 gene.

In various embodiments, a humanized Angptl8 gene as described herein comprises a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to a nucleotide coding sequence that appears in SEQ ID NO:5 or SEQ ID NO:7.

In various embodiments, a humanized Angptl8 gene as described herein comprises a nucleotide coding sequence (e.g., a cDNA sequence) that is substantially identical or identical to a nucleotide coding sequence that appears in SEQ ID NO:5 or SEQ ID NO:7.

In various embodiments, a humanized Angptl8 gene as described herein encodes an Angptl8 polypeptide that is identical or substantially identical to a human ANGPTL8 polypeptide. In various embodiments, a humanized Angptl8 gene as described herein encodes art Angptl8 polypeptide that is identical or substantially identical to a full-length human ANGPTL8 protein translated from a human ANGPTL8 gene (which includes a human ANGPTL8 signal peptide, or the first 21 amino acids of a human ANGPIL8 full-length protein).

In various embodiments, a humanized Angptl8 gene as described herein encodes an Angptl8 polypeptide having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence that appears in SEQ ID NO:6 or SEQ ID NO:8.

In various embodiments, a humanized Angptl8 gene as described herein encodes an Angptl8 polypeptide having an amino acid sequence that is substantially identical or identical to an amino acid sequence that appears in SEQ ID NO:6 or SEQ ID NO:8.

In various embodiments, an Angptl8 polypeptide produced by a non-human animal as described herein comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 22-198 of SEQ ID NO:6 or SEQ ID NO:8.

In various embodiments, an Angptl8 polypeptide produced by a non-human animal as described herein comprises an amino acid sequence that is substantially identical or identical to amino acid residues 22-198 of SEQ ID NO:6 or SEQ ID NO:8.

In various embodiments, an Angptl8 polypeptide produced by a non-human animal as described herein comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 77-134 of SEQ ID NO:6 or SEQ ID NO:8.

In various embodiments, an Angptl8 polypeptide produced by a non-human animal as described herein comprises an amino acid sequence that is substantially identical or identical to amino acid residues 77-134 of SEQ ID NO:6 or SEQ ID NO:8.

In various embodiments, an Angptl8 polypeptide produced by a non-human animal as described herein comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 156-193 of SEQ ID NO:6 or SEQ ID NO:8.

In various embodiments, an Angptl8 polypeptide produced by a non-human animal as described herein comprises an amino acid sequence that is substantially identical or identical to amino acid residues 156-193 of SEQ ID NO:6 or SEQ ID NO:8.

In various embodiments, an Angptl8 polypeptide produced by a non-human animal as described herein comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 22-60 of SEQ ID NO:6 or SEQ ID NO:8.

In various embodiments, an Angptl8 polypeptide produced by a non-human animal as described herein comprises an amino acid sequence that is substantially identical or identical to amino acid residues 22-60 of SEQ ID NO:6 or SEQ ID NO:8.

In various embodiments, an Angptl8 polypeptide produced by a non-human animal as described herein includes one or more coiled-coil domains, wherein said one or more coiled-coil domains comprise an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to one or more coiled-coil domains that appear in SEQ ID NO:6 or SEQ ID NO:8.

In various embodiments, an Angptl8 polypeptide produced by a non-human animal as described herein includes one or more coiled-coil domains, wherein said one or more coiled-coil domain comprise an amino acid sequence that is substantially identical or identical to one or more coiled-coil domains that appear in SEQ ID NO:6 or SEQ ID NO:8.

In various embodiments, an Angptl8 polypeptide produced by a non-human animal as described herein has an N-terminal region, which N-terminal region comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an N-terminal region that appears in SEQ ID NO:6 or SEQ ID NO:8.

In various embodiments, an Angptl8 polypeptide produced by a non-human animal as described herein has an N-terminal region, which N-terminal region comprises an amino acid sequence that is substantially identical or identical to an N-terminal region that appears in SEQ NO:6 or SEQ ID NO:8.

Compositions and methods for making non-human animals that express a human or humanized Angptl8 polypeptide, including specific polymorphic forms, allelic variants (e.g., single amino acid differences) or alternatively spliced isoforms, are provided, including compositions and methods for making non-human animals that express such polypeptides from a human promoter and a human regulatory sequence. In some embodiments, compositions and methods for making non-human animals that express such proteins from a non-human promoter and a non-human regulatory sequence are also provided. In some embodiments, compositions and methods for making non-human animals that express such proteins from an endogenous promoter and an endogenous regulatory sequence are also provided. In some certain embodiments, endogenous promoters and endogenous regulatory sequences are endogenous rodent promoters and endogenous rodent regulatory sequences. The methods include inserting the genetic material encoding a human ANGPTL8 polypeptide, in whole or in part, at a precise location in the genome of a non-human animal that corresponds to an endogenous Angpii8 gene thereby creating a humanized Angptl8 gene that expresses an Angptl8 polypeptide that is human in whole or in part. In some embodiments, methods include inserting genomic DNA corresponding to exons 1-4 of a human ANGPTL8 gene, in whole or in part, into an endogenous Angptl8 gene of the non-human animal thereby creating a humanized gene that encodes an Angptl8 polypeptide that contains a human portion containing amino acids encoded by the inserted exons.

Where appropriate, the coding region of the genetic material or polynucleotide sequence(s) encoding a human (or humanized) ANGPTL8 polypeptide, in whole or in part, may be modified to include codons that are optimized for expression from cells in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a human (or humanized) ANGPTL8 polypeptide, in whole or in part, may include an altered sequence to optimize codon usage for a particular cell type (e.g., a rodent cell). For example, the codons of the genomic DNA corresponding to exons 1-4 of a human ANGPTL8 gene, in whole or in part, to be inserted into an endogenous Angptl8 gene of a non-human animal (e.g., a rodent) may be optimized for expression in a cell of the non-human animal. Such a sequence may be described as a codon-optimized sequence.

Methods for generating transgenic non-human animals, including knockouts and knock-ins, are well known in the art (see, e.g., Gene Targeting: A Practical Approach, Joyner, ed., Oxford University Press, Inc. (2000)). For example, generation of transgenic rodents may optionally involve disruption of the genetic loci of one or more endogenous rodent genes (or gene segments) and introduction of one or more heterologous genes (or Angptl8-encoding sequences) into the rodent genome, in some embodiments, at the same location as an endogenous rodent gene (or gene segments).

In some embodiments, heterologous (e.g., human or humanized) Angptl8 genes or heterologous Angptl8-encoding sequences as described herein are randomly introduced in the genome of a rodent. In such embodiments, rodents comprising, containing or otherwise harboring randomly introduced heterologous (or humanized Angptl8 genes or heterologous Angptl8-encoding sequences) can be characterized as having a heterologous Angptl8 transgene or heterologous Angptl8 transgene construct. Typically, a transgene and/or transgene construct includes, among other things, a nucleic acid sequence (encoding e.g., a polypeptide of interest, in whole or in part) that is introduced into a non-human cell (e.g., a rodent embryonic stem cell) by the hand of man using methods described herein or otherwise known in the art. Further, a transgene may be partly or entirely heterologous, i.e., foreign, to a non-human animal or cell into which it is introduced. A transgene can further include one or more transcriptional regulatory sequences and any other nucleic acid, such as introns or promoters (e.g., constitutive, tissue-specific, etc.), which may be necessary for expression of a selected nucleic acid sequence. In some embodiments, heterologous (or humanized) Angptl8 genes or heterologous Angptl8-encoding sequences as described herein are introduced into an endogenous Angptl8 gene in the genome of a rodent; in some certain embodiments, an endogenous Angptl8 gene locus is altered, modified, or engineered to contain human ANGPTL8 sequences (or gene fragments) operably linked to one or more non-human Angptl8 sequences (or gene fragments).

As described herein, heterologous (or humanized) Angptl8 genes or heterologous Angptl8-encoding sequences are operably linked to expression control sequences such as a promoter to drive expression of the heterologous (or humanized) Angptl8 in the non-human animals. In some embodiments, such promoters are non-human Angptl8 promoters (e.g., a rodent Angptl8 promoters). Persons of skill upon reading this disclosure will recognize that other non-human promoters may be operably linked to heterologous Angptl8 sequences inserted into the genome of non-human animals as described herein regardless if such heterologous Angptl8 sequences are placed at the same location as an endogenous non-human gene or randomly integrated in the genome of the non-human animal. In some embodiments, a non-human promoter is or comprises a constitutive promoter. In some embodiments, a non-human promoter is or comprises a viral promoter (e.g., simian virus promoter, herpes simplex virus promoter, papilloma virus promoter, adenovirus promoter, retrovirus promoter, etc.). In some embodiments, a non-human promoter is a mammalian promoter. Suitable examples of promoters that can be used in accordance with the present invention include, but are not limited to, SRα promoters, human or murine CMV promoters, EF1α promoters and SV40 early promoter regions. Other promoters that control expression of desired polypeptides in a. tissue-specific manner are known in the art and can be employed in the methods described herein as desired. Further, promoters may be selected depending on a desired cell type for expression. Exemplary promoters can be found in, e.g., Villa-Komaroff et al., 1978, Proc. Natl. Acad. Sci. U.S.A. 75:3727-31; Benoist et al., 1981, Nature 290:304-10; Wagner et al., 1981, Proc. Natl. Acad. Sci. U.S.A. 78:1441-5; Brinster et al., 1982, Nature 296:39-42; DeBoer et al., 1983, Proc. Natl. Acad. Sci. U.S.A. 80:21-5; Boshart et al., 1985, Cell 41:521-30; Foecking et al., 1986, Gene 45:101-5; Takebe et al., 1988, Mol. Cell. Bio. 8:466-72.

A humanized Angptl8 gene approach employs a relatively minimal modification of the endogenous protein interactions and signaling and results in natural Angptl8-mediated functions and/or activity in the non-human animal, in various embodiments, because the genomic sequence of the Angptl8 sequences are modified in a single fragment and therefore retain normal functionality by including necessary regulatory sequences. Further, in various embodiments, the modification does not affect the secretion of a functional Angptl8 polypeptide in the serum and maintains normal functions andlor interactions via binding to various lipids (e.g., triglycerides).

A schematic illustration (not to scale) of the genomic organization of an endogenous murine Angptl8 gene and a human ANGPTL8 gene is provided in FIG. 1. An exemplary method for humanizing an endogenous murine Angptl8 gene using a genomic fragment containing exons 1-4 and a 3' UTR of a human ANGPTL8 gene is provided in FIG. 3. As illustrated, a 2,383 bp synthetic DNA fragment corresponding to exons 1-4 and a 3' UTR of a human ANGPTL8 gene is inserted into the place of a 1,576 bp sequence of an endogenous murine Angptl8 gene locus via homologous recombination with a targeting construct. The 2,383 bp synthetic DNA fragment may be cloned directly from human DNA or synthesized from a source sequence (e.g., GenBank accession no. NM_018687.6, SEQ ID NO:5). This genomic DNA includes the portion of the gene that encodes at least about amino acid residues 22-198 of a human ANGPTL8 polypeptide responsible for lipid binding.

Figure 3:
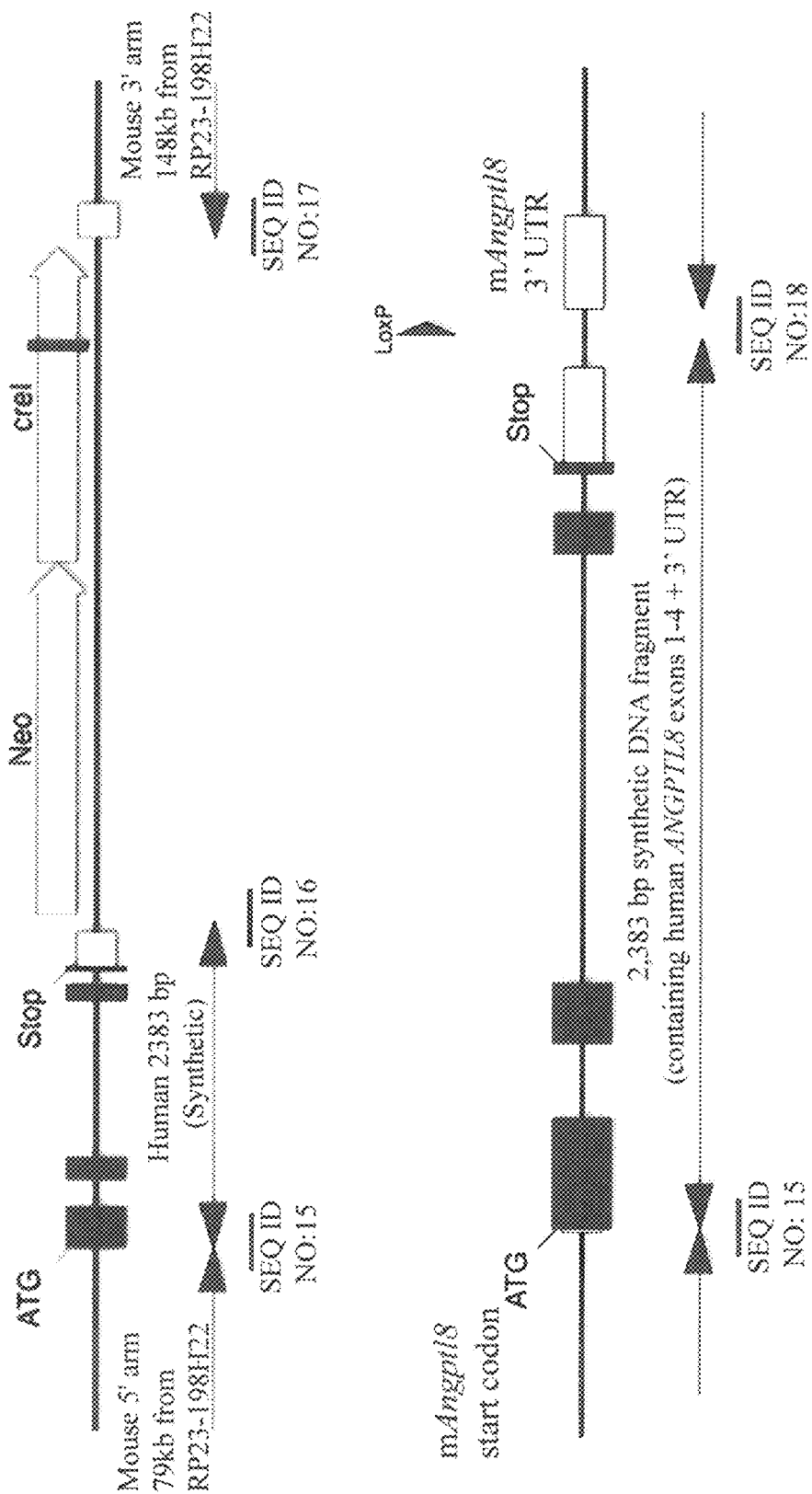
FIG. 3 shows a representative diagram, not to scale, of an exemplary method for humanization of a non-human Angptl8 gene. Top: a targeting vector made according to Example 1 for insertion into a murine Angptl8 locus via homologous recombination; Bottom: targeted murine Angptl8 locus after insertion of the targeting vector via homologous recombination and recombinase-mediated deletion of a selection cassette. Selected nucleotide junction locations are marked with a line below each junction and each indicated by SEQ ID NO.

A non-human animal (e.g., a mouse) having a humanized Angptl8 gene at an endogenous Angptl8 locus can be made by any method known in the art. For example, a targeting vector can be made that introduces a human ANGPTL8 gene, in whole or in part, with a selectable marker gene. FIG. 3 illustrates a targeting vector that contains an endogenous Angptl8 locus of a mouse genome comprising an insertion of a 2,383 bp synthetic DNA fragment that corresponds to exons 1-4 (specifically, the coding portion of exon 1, exon 2, exon 3 and exon 4 which includes the 3' UTR) of a human ANGPTL8 gene. As illustrated, the targeting construct contains a 5' homology arm containing sequence upstream of exon 1 (i.e., including the ATG start codon) of an endogenous murine Angptl8 gene (~79 kb), followed by the 2,383 bp synthetic DNA fragment, a drug selection cassette (e.g., a neomycin resistance gene flanked on both sides by loxP sequences; ~5 kb), and a 3' homology arm containing the 3' UTR of an endogenous murine Angptl8 gene (~148 kb). The targeting construct contains a self-deleting drug selection cassette (e.g., a neomycin resistance gene flanked by loxP sequences; see U.S. Pat. Nos. 8,697,851, 8,518,392 and 8,354,389, all of which are incorporated herein by reference). Upon electroporation in embryonic stem cells, a modified endogenous Angptl8 gene is created that includes 2,383 bp of a human ANGPTL8 gene (i.e., the coding portion of exon 1, exon 2, exon 3 and exon 4 which includes the 3' UTR) in the place of 1,576 bp of an endogenous wild-type Angptl8 gene, which is contained in the targeting vector. A humanized Angptl8 gene is created resulting in a cell or non-human animal that expresses a humanized Angptl8 polypeptide that contains amino acids encoded by the 2,383 bp synthetic DNA fragment. The drug selection cassette is removed in a development-dependent manner, i.e., progeny derived from mice whose germ line cells containing the humanized Angptl8 gene described above will shed the selectable marker from differentiated cells during development (see bottom of FIG. 3).

Exemplary promoters than can be operably linked with drug selection cassettes and/or recombinase genes included in targeting vectors described herein are provided below. Additional suitable promoters that can be used in targeting vectors described herein include those described in U.S. Pat. Nos. 8,697,851, 8,518,392 and 8,354,389; all of which are incorporated herein by reference). Exemplary promoter sequences include a Protamine 1 (Prm1) promoter (SEQ ID NO:12), a Blimp1 promoter 1 kb (SEQ ID NO:13), and a Blimp1 promoter 2 kb (SEQ ID NO:14).

In some embodiments, a non-human animal having a humanized Angptl8 gene as described herein can be characterized as transgenic for the humanized Angptl8 gene or a transgenic Angptl8 non-human animal. Such descriptions are used interchangeably herein and refer to any non-naturally occurring non-human animal in which one or more of the cells of the non-human animal contain a heterologous Angptl8 nucleic acid sequence and/or Angptl8-encoding sequence, in whole or in part, as described herein. In some embodiments, a heterologous Angptl8 nucleic acid sequence and/or Angptl8-encoding sequence, in whole or in part, is introduced into a cell, directly or indirectly by introduction into a precursor cell, by way of deliberate genetic manipulation, such as by microinjection or by infection with a recombinant virus. In such embodiments, genetic manipulation does not include classic breeding techniques, but rather is directed to introduction of recombinant DNA molecule(s) that contain a heterologous Angptl8 nucleic acid sequence and/or Angptl8-encoding sequence, in whole or in part, as described herein. Such a molecule may be integrated within a chromosome, or it may be extrachromosomally replicating DNA. As described herein, transgenic non-human animals includes animals that are heterozygous or homozygous for a heterologous Angptl8 nucleic acid sequence and/or Angptl8-encoding sequence, in whole or in part, and/or animals that have single or multiple copies of a heterologous Angptl8 nucleic acid sequence and/or Angptl8-encoding sequence, in whole or in part, as described herein.

A transgenic founder non-human animal can be identified based upon the presence of a humanized Angptl8 gene in its genome and/or expression of Angptl8 polypeptides containing amino acids encoded by the inserted genetic material in tissues or cells of the non-human animal. A transgenic founder non-human animal can then be used to breed additional non-human animals carrying the humanized Angptl8 gene thereby creating a series of non-human animals each carrying one or more copies of a humanized Angptl8 gene. Moreover, transgenic non-human animals carrying a humanized Angptl8 gene can further be bred to other transgenic non-human animals carrying other transgenes (e.g., human immunoglobulin genes) as desired.

Transgenic non-human animals may also be produced to contain selected systems that allow for regulated or directed expression of the humanized. Angptl8 gene (or humanized Angptl8 transgene). Exemplary systems include the Cre/loxP recombinase system of bacteriophage P1 (see, e.g., Lakso, M. et al., 1992, Proc. Natl. Acad. Sci. U.S.A. 89:6232-6) and the FLP/Frt recombinase system of S. cerevisiae (O'Gorman, S. et al, 1991, Science 251:1351-5). Such animals can be provided through the construction of "double" transgenic animals, e.g., by mating two transgenic animals, one containing a transgene comprising a selected modification (e.g., a humanized Angptl8 gene or transgene) and the other containing a transgene encoding a recombinase (e.g., a Cre recombinase).

Although embodiments employing a humanized Angptl8 gene in a mouse (i.e., a mouse with a Angptl8 gene that encodes a Angptl8 polypeptide having a human sequence, in whole or in part) are extensively discussed herein, other non-human animals that comprise a humanized Angptl8 gene are also provided. In some embodiments, such non-human animals comprise a humanized Angptl8 gene operably linked to a rodent Angptl8 promoter. In some embodiments, such non-human animals comprise a humanized Angptl8 gene operably linked to an endogenous Angptl8 promoter; in some embodiments, an endogenous rodent Angptl8 promoter. In some embodiments, such non-human animals express a humanized Angptl8 polypeptide from an endogenous locus, wherein the humanized Angptl8 polypeptide comprises at least amino acid residues 22-60, 77-134, 156-193 or 22-198 of a human ANGPTL8 polypeptide. Such non-human animals include any of those which can be genetically modified to express a Angptl8 polypeptide as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

For example, a rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, a rat pluripotent and/or totipotent cell can be from a DA strain or an ACI strain. An ACI rat strain is characterized as having black agouti, with white belly and feet and an $RT1^{av1}$ haplotype. Such strains are available from a variety of sources including Harlan Laboratories. An example of a rat ES cell line from an ACI rat is an ACI.G1 rat ES cell. A Dark Agouti (DA) rat strain is characterized as having an agouti coat and an $RT1^{av1}$ haplotype. Such rats are available from a variety of sources including Charles River and Harlan Laboratories. Examples of a rat ES cell line from a DA rat are the DA.2B rat ES cell line and the DA.2C rat ES cell line. In some cases, rat pluripotent and/or totipotent cells are from an inbred rat strain. See, e.g., U.S. Patent Application Publication No. 2014-0235933 A1 incorporated herein by reference.

Methods for modifying a non-human animal genome (e.g., a pig, cow, rodent, chicken, etc. genome) include, e.g., employing a zinc finger nuclease (ZFN), a transcription activator-like effector nuclease (TALEN), or a Cas protein (i.e., a CRISPR/Cas system) to modify a genome to include a humanized Angptl8 gene.

Methods Employing Non-Human Animals Having a Humanized ANGPTL8 Gene

The present invention is, among other things, based on the recognition that the creation of an in vivo system that exploits regulatory molecules of lipid metabolism can be made using a humanized Angptl8 gene as described herein. Such an in vivo system allows for the development of therapeutics and/or therapeutic regimens that focus on ameliorating the effects of lipid dysfunction in human patients. Further, such an in vivo system also provides for the development of therapeutics and/or therapeutic regimens that focus on altering Angiopoietin-associated regulation of lipid metabolism in hypertriglyceridemia and/or cardiovascular diseases, disorders or conditions.

Non-human animals as described herein provide an improved in vivo system and source of biological materials (e.g., cells) expressing human (or humanized) ANGPTL8 that are useful for a variety of assays. In various embodiments, non-human animals as described herein are used to develop therapeutics that target human ANGPTL8 and/or modulate human ANGPTL8 signaling (e.g., disrupting interactions with human ANGPTL8 binding partners, such as ANGPTL3). In various embodiments, non-human animals as described herein are used to screen and develop candidate therapeutics (e.g., antibodies) that block interaction of human ANGPTL8 with human ANGPTL3. In various embodiments, non-human animals as described herein are used to determine the binding profile of antagonists and/or agonists of human ANGPTL8 in a non-human animal as described herein; in some embodiments, non-human animals as described herein are used to determine the epitope or epitopes of one or more candidate therapeutic antibodies that bind human ANGPTL8.

In various embodiments, non-human animals as described herein are used to determine the pharmacokinetic profiles of anti-ANGPTL8 antibodies. In various embodiments, one or more non-human animals as described herein and one or more control or reference non-human animals are each exposed to one or more candidate therapeutic anti-ANGPTL8 antibodies at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mng, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals as described herein are used to measure the therapeutic effect of blocking or modulating human ANGPTL8 signaling and the effect on gene expression as a result of cellular changes. In various embodiments, a non-human animal as described herein or cells isolated therefrom are exposed to a candidate therapeutic that binds a human ANGPTL8 polypeptide (or a portion of a human ANGPTL8 polypeptide) in the non-human animal and, after a subsequent period of time, analyzed for effects on ANGPTL8-dependent processes, for example, triglyceride metabolism, lipoprotein lipase activity and uptake of various lipoproteins (e.g., low-density lipoprotein, LDL).

Non-human animals as described herein express human (or humanized) ANGPTL8 polypeptide, thus cells, cell lines, and cell cultures can be generated to serve as a source of human ANGPTL8 for use in binding and functional assays, e.g., to assay for binding or function of a ANGPTL8 antagonist or agonist, particularly where the antagonist or agonist is specific for a human ANGPTL8 sequence or epitope or, alternatively, specific for a human ANGPTL8 sequence or epitope that associates with ANGPTL3. In various embodiments, ANGPTL8 epitopes bound by candidate therapeutic antibodies can be determined using cells isolated from non-human animals as described herein. In various embodiments, a human (or humanized) ANGPTL8 polypeptide expressed by a non-human animal as described herein may comprise a variant amino acid sequence. In various embodiments, non-human animals as described herein express a human (or humanized) ANGPTL8 variant. In various embodiments, the variant is polymorphic at an amino acid position associated with ligand binding. In various embodiments, non-human animals as described herein are used to determine the effect of ligand binding through interaction with a polymorphic variant of human ANGPTL8. Exemplary variant human ANGPTL8 polypeptides include a variant characterized by an R59W (Quagliarini, F. et al., 2012, Proc. Nat. Acad. Sci. U.S.A. 109(48): 19751-6) or Q121X (Clapham et al., BMC Endocr Disord. 2016, 16:7) amino acid substitution. In some embodiments, a variant human ANGPTL8 polypeptide is associated with lower plasma low-density lipoprotein (LDL)-cholesterol and/or high-density lipoprotein (HDL)-cholesterol levels. In some embodiments, a variant human ANGPTL8 polypeptide is associated with lower plasma triglycerides and/or HDL-cholesterol levels.

Cells from non-human animals as described herein can be isolated and used on an ad hoc basis, or can be maintained in culture for many generations. In various embodiments, cells from a non-human animal as described herein are immortalized (e.g., via use of a virus) and maintained in culture indefinitely (e.g., in serial cultures).

Non-human animals as described herein provide an in vivo system for assessing the pharmacokinetic properties of a drug (e.g., an ANGPTL8 modulator). In various embodiments, a drug may be delivered or administered to one or more non-human animals as described herein, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs are monitored in or through the use of non-human animals as described herein.

In some embodiments, performing an assay includes determining the effect on the phenotype and/or genotype of the non-human animal to which the drug is administered. In some embodiments, performing an assay includes determining lot-to-lot variability for a drug. In some embodiments, performing an assay includes determining the differences between the effects of a drug administered to a non-human animal as described herein and a reference non-human animal. In various embodiments, reference non-human animals may have a modification as described herein, a modification that is different from one as described herein or no modification (i.e., a wild-type non-human animal).

Exemplary parameters that may be measured in non-human animals (or in and/or using cells isolated therefrom) for assessing the pharmacokinetic properties of a drug include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity and the like. In various embodiments, non-human animals as described herein are used to determine a pharmaceutically effective dose of a drug.

Non-human animals as described herein provide an in vivo system for the analysis and testing of a drug or vaccine. In various embodiments, a candidate drug or vaccine may be administered to one or more non-human animals as described herein, followed by monitoring of the non-human animals to determine one or more of the immune response to the drug or vaccine, the safety profile of the drug or vaccine, or the effect on a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Vaccine efficacy may be determined in a number of ways. Briefly, non-human animals described herein are vaccinated using methods known in the art and then challenged with a vaccine, or a vaccine is administered to already-infected non-human animals. The response of a non-human animal(s) to a vaccine may be measured by monitoring of, and/or performing one or more assays on, the non-human animal(s) (or cells isolated therefrom) to determine the efficacy of the vaccine. The response of a non-human animal(s) to the vaccine is then compared with control animals, using one or more measures known in the art and/or described herein.

Vaccine efficacy may further be determined by viral neutralization assays. Briefly, non-human animals described herein are immunized and serum is collected on various days post-immunization. Serial dilutions of serum are pre-incubated with a virus during which time antibodies in the serum that are specific for the virus will bind to it. The virus/serum mixture is then added to permissive cells to determine infectivity by a plaque assay or microneutralization assay. If antibodies in the serum neutralize the virus, there are fewer plaques or lower relative luciferase units compared to a control group.

In various embodiments, non-human animals as described herein are used in efficacy studies to determine the in vivo effect of anti-ANGPTL8 therapeutics (e.g., anti-ANGPTL8 antibodies) on circulating triglyceride levels. For example, non-human animals as described herein are bled prior to administration of candidate therapeutics or controls and organized into various treatment groups as desired. Candidate therapeutics or controls are administered at a desired dosage and bled on consecutive days after administration. Plasma levels of triglycerides, glucose and/or insulin may be measured using collected serum. Levels of candidate therapeutics may also be measured as desired. Exemplary assays that can be used for detection of various molecules include ELISA assays and others as described in Wang, Y. et al., 2013, Proc. Nat. Acad. Sci. U.S.A. 110(40):16109-114; Quagliarini, F. et al., 2012, Proc. Nat. Acad. Sci. U.S.A. 109(48):19751-6.

In various embodiments, non-human animals as described herein are used to determine lipoprotein lipase (LPL) activity after treatment with anti-ANGPTL8 therapeutics anti-ANGPTL8 antibodies). For example, non-human animals as described herein are bled prior to administration of candidate therapeutics or controls and put into various treatment groups as desired. Candidate therapeutics or controls are administered at a desired dosage and bled at consecutive days after administration. After sufficient time (e.g., several days), non-human animals are administered an anti-coagulant (e.g., heparin) so that LPL is released from vascular endothelial surfaces and blood is obtained from the non-human animals shortly thereafter. Post-heparin plasma is fractionated to separate LPL using heparin-Sepharose chromatography and LPL activities are assayed using a lipase substrate. For example, general methods and assays are described in Wang, Y. et al., 2013, Proc. Nat. Acad. Sci. U.S.A. 110(40):16109-114; Quagliarini, F. et al., 2012, Proc. Nat. Acad. Sci. U.S.A. 109(48): 19751-6.

In various embodiments, non-human animals as described herein are used in lipid tolerance tests to determine triglyceride clearance by acute fat loading after treatment with anti-ANGPTL8 therapeutics (e.g., anti-ANGPTL8 antibodies). For example, non-human animals as described herein are bled prior to administration of candidate therapeutics or controls and put into various treatment groups. Candidate therapeutics or controls are administered at a desired dosage. After several days, non-human animals are subjected to a fasting regimen following administration of a lipid emulsion (e.g., 20% concentration) according to body weight. Plasma triglyceride levels are determined in blood collected from non-human animals in each treatment group. For example, general methods and assays are described in Wang, Y. et al., 2013, Proc. Nat. Acad. Sci. U.S.A. 110(40):16109-114; Quagliarini, F. et al., 2012, Proc. Nat. Acad. Sci. U.S.A. 109(48):19751-6.

Non-human animals as described herein provide an improved in vivo system for the development and characterization of candidate therapeutics for use in hypertriglyceridemia. In various embodiments, non-human animals as described herein may be subjected to a specific feeding regimen (e.g. overfeeding or fasting), followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously. The non-human animals may be subjected to the feeding regimen for a sufficient time so that ANGPTL8 levels are at a high level in one or more locations (e.g., liver and/or adipose tissue) within the non-human animal. Plasma levels of triglyceride, glucose and/or insulin, and lipoprotein lipase activity, etc. may be measured both before and after administration of the candidate therapeutic(s). Cytoxicity of candidate therapeutics may also be measured in the non-human animal as desired.

Non-human animals as described herein may be used to develop one or more disease models to evaluate or assess candidate therapeutics and/or therapeutic regimens (e.g., monotherapy, combination therapy, dose range testing, etc.) to effectively treat diseases, disorders or conditions that affect humans. Various disease conditions may be established in non-human animals as described herein followed by administration of one or more candidate molecules (e.g., drugs targeting ANGPTL8) so that efficacy of the one or more candidate molecules in a disease condition can be determined. Non-human animals may be placed into different treatment groups according to dose so that an optimal dose or dose range that correlates with effective treatment of an established disease can be determined. In some embodiments, disease models include cardiovascular diseases, disorders or conditions.

Candidate molecules can be administered to non-human animal disease models using any method of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. When a combination therapy is evaluated in non-human animals as described herein, candidate molecules can be administered via the same administration route or via different administration routes. When a dosing regimen is evaluated in non-human animals as described herein, candidate molecules may be administered at bimonthly, monthly, triweekly, biweekly, weekly, daily, at variable intervals and/or in escalating concentrations to determine a dosing regimen that demonstrates a desired therapeutic or prophylactic effect in a non-human animal in which one or more disease models has been established.

Kits

The present, invention further provides a pack or kit comprising one or more containers filled with at least one non-human animal, non-human cell, DNA fragment (or construct), and/or targeting vector as described herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both, or a contract that governs the transfer of materials and/or biological products (e.g., a non-human animal or non-human cell as described herein) between two or more entities.

Other features of the invention will become apparent in the course of the following descriptions of exemplary embodiments, which are given for illustration and are not intended to be limiting thereof.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Modification of an Endogenous Angiopoietin-Like Protein 8 Gene

This example illustrates exemplary methods of modifying an endogenous Angptl8 gene in a non-human mammal such as a rodent (e.g., a mouse) so that said endogenous Angptl8 gene encodes a human ANGPTL8 polypeptide. The methods described in this example can be employed to modify an endogenous Angptl8 gene of a non-human animal using any human sequence (e.g., a variant), or combination of human sequences (or sequence fragments) as desired. In this example, a 2,383 bp synthetic DNA fragment containing exons 1-4 (excluding the ATG start codon) of a human ANGPTL8 gene that appears in GenBank accession NM_018687.6 (SEQ ID NO: 5) was employed for modifying an endogenous Angptl8 gene of a mouse. Alignment of mouse, human, and exemplary human ANGPTL8 polypeptide expressed by a rodent as described herein, with signal peptide indicated in boxes for each sequence, is depicted in FIG. 2. FIG. 3 shows a targeting vector for modifying an endogenous Angptl8 gene of a rodent to encode a human ANGPTL8 polypeptide that was constructed using VELOCIGENE® technology (see, e.g., U.S. Pat. No. 6,586,251 and Valenzuela et al., 2003, Nature Biotech. 21(6):652-659; herein incorporated by reference).

Briefly, mouse bacterial artificial chromosome (BAC) clone RP23-198h22 (Invitrogen) was modified to delete the sequence containing immediately downstream of the endogenous Angptl8 ATG start codon to 9 bp beyond the stop codon (i.e., exon 1 except the 5' 11 nucleotides, exons 2-3, and the 5' portion of exon 4 through 9 bp beyond the stop codon) and insert just downstream of the human ANGPTL8 ATG start codon to beyond the human ANGPTL8 3'UTR (i.e., the coding portion of exon 1 beginning just downstream of the ATG start codon through exon 4) using a 2,383 bp synthetic DNA fragment, which encodes a human ANGPTL8 polypeptide. Endogenous DNA containing the 5' and 3' untranslated regions (UTRs) as well as the endogenous Angptl8 ATG start codon were retained. Thus, exons 1-4 of a human ANGPTL8 gene, without the human ANGPTL8 start codon, was fused in frame to the endogenous Angptl8 ATG start codon. Sequence analysis of the 2,383 bp synthetic DNA fragment (i.e., corresponding to exons 1-4 of a human ANGPTL8 gene) confirmed all human ANGPTL8 exons and splicing signals. Sequence analysis revealed that the sequence matched the reference genome and ANGPTL8 transcript NM_018687.6.

The 2,383 bp synthetic DNA fragment was synthesized by Genescript Inc. (Piscataway, N.J.) and cloned into an ampicillin-resistant plasmid vector. Unique restriction enzyme recognition sites were employed to ligate a ~4,996 bp self-deleting neomycin cassette flanked by recombinase recognition sites (loxP-hUb1-em7-Neo-pA-mPrm1-Crei-loxP; see U.S. Pat. Nos. 8,697,851, 8,518,392 and 8,354, 389, all of which are incorporated herein by reference). Subsequent selection in bacterial cells was performed via plating on agar medium containing neomycin. The targeting vector was linearized prior to homologous recombination with mouse BAC clone RP23-198U22. By design, the junction between the human ANGPTL8 2,383 bp fragment and the mouse downstream sequence included a human ANGPTL8 3' UTR followed by a mouse Angptl8 3' UTR (FIG. 3). The resulting targeting vector contained, from 5' to 3', a 5' homology arm containing ~79 kb of mouse genomic DNA from BAC clone RP23-198h22, 2,383 bp synthetic DNA fragment (corresponding to exons 1-4 of a human ANGPTL8 gene), a self-deleting neomycin cassette flanked by loxP sites, and ~148 kb of mouse genomic DNA from BAC clone RP23-198h22.

The modified bMQ-400O17 BAC clone described above was used to electroporate mouse embryonic stem (ES) cells to create modified ES cells comprising an endogenous Angptl8 gene that is humanized from exon 1 (minus the ATG start codon) through exon 4 including a human ANGPTL8 3' UTR (i.e., deletion of 1,576 bp of an endogenous Angptl8 gene and insertion of 2.383 bp of human ANGPTL8-encoding sequence). Positively targeted ES cells containing the modified Angptl8 gene were identified by an assay (Valenzuela et al., supra) that detected the presence of the human ANGPTL8 sequences (e.g., exons 1-4) and confirmed the loss and/or retention of mouse Angptl8 sequences (e.g., exons 1-4 and/or 5' and 3' UTRs). Table 1 sets forth the primers and probes that were used to confirm modification of an endogenous Angptl8 gene as described above (FIG. 4).

The nucleotide sequence across the upstream insertion point included the following, which indicates endogenous mouse sequence (contained within the parentheses below with the ATG start codon in bold font) contiguous with human ANGPTL8 genomic sequence at the insertion point: (AAGGCAGCCG CAGCGGCCCG GGAACCACAC CCACGAAACT GTCAGCCATG) CCAGTGCCTG CTCTGTGCCT GCTCTGGGCC CTGGCAATGG TGAC-CCGGCC (SEQ ID NO: 15) (FIG. 9A). See, also, FIG. 3.

The nucleotide sequence across the 5' end of the self-deleting neomycin cassette included the following, which indicates human ANGPTL8 genomic sequence contiguous with cassette sequence (contained within the parentheses below with an XhoI site italicized and a loxP site in bold font) downstream of the insertion point: GGGAGACCCC ACCCAGCATG ATGTATGAAT ACCTCCCATT CAAGT-GCCCA (CTCGAG ATAACTTCG TATAATGTAT GCTATACGAA GTTAT ATGCATGGCC TCCGCGCCGG GTTTTGGCGC CTCCCGCGGG CGCCCCCCTC CTCACGGCGA GCGCTGCCAC GTCAGACGAA GGGCGCAGCG AGCGTCCTGA) (SEQ ID NO:16) (FIG. 9B). See, also, FIG. 3.

The nucleotide sequence across the downstream insertion point at the 3° end of the self-deleting neomycin cassette included the following, which indicates cassette sequence (contained within the parentheses below with a loxP site in bold font, an I-CeuI recognition site underlined and an NheI recognition site italicized) contiguous with mouse Angptl8 genomic sequence:

(SEQ ID NO: 17)
(TTTCACTGCAT TCTAGTTGTG GTTTGTCCAA ACTCATCAAT

GTATCTTATC ATGTCTGGA ATAACTTCGTATAATGTATGCTATAC

GAAGTTAT<u>GCTAGTAACTATAACGGTCCTAAGGTAGCGA</u> *GCTAGC*)

GATGCCACCGAGGACCAGTTGT GCTGCAAGGAA CACTGAAGCG

CTCCACC (FIG. 9C).

See, also, FIG. 3.

The nucleotide sequence across the downstream insertion point after deletion of the neomycin cassette (77 bp remaining between a human ANGPTL8 3'UTR and a mouse Angptl8 3'UTR) included the following, which indicates human and mouse genomic sequence juxtaposed with remaining cassette sequence (contained within the parentheses below with XhoI and NheI recognition sites italicized, a loxP site in bold, and an I-CeuI restriction site underlined):

(SEQ ID NO: 18)
(GGGAGACCCC ACCCAGCATG ATGTATGAAT ACCTCCCATT

CAAGTGCCCA (*GTCGAG* ATAACTTCGTATAATGTATGCTATACGA

AGTTAT<u>GCTAGTAACTATAACGGTCCTAAGGTAGCGA</u> *GCTAGC*)

GATGCCACCG AGGACCAGTT GTGCTGCAAG GAACACTGAA

GCGCTCCACC (FIG. 9D).

See, also, FIG. 3.

Figure 4:
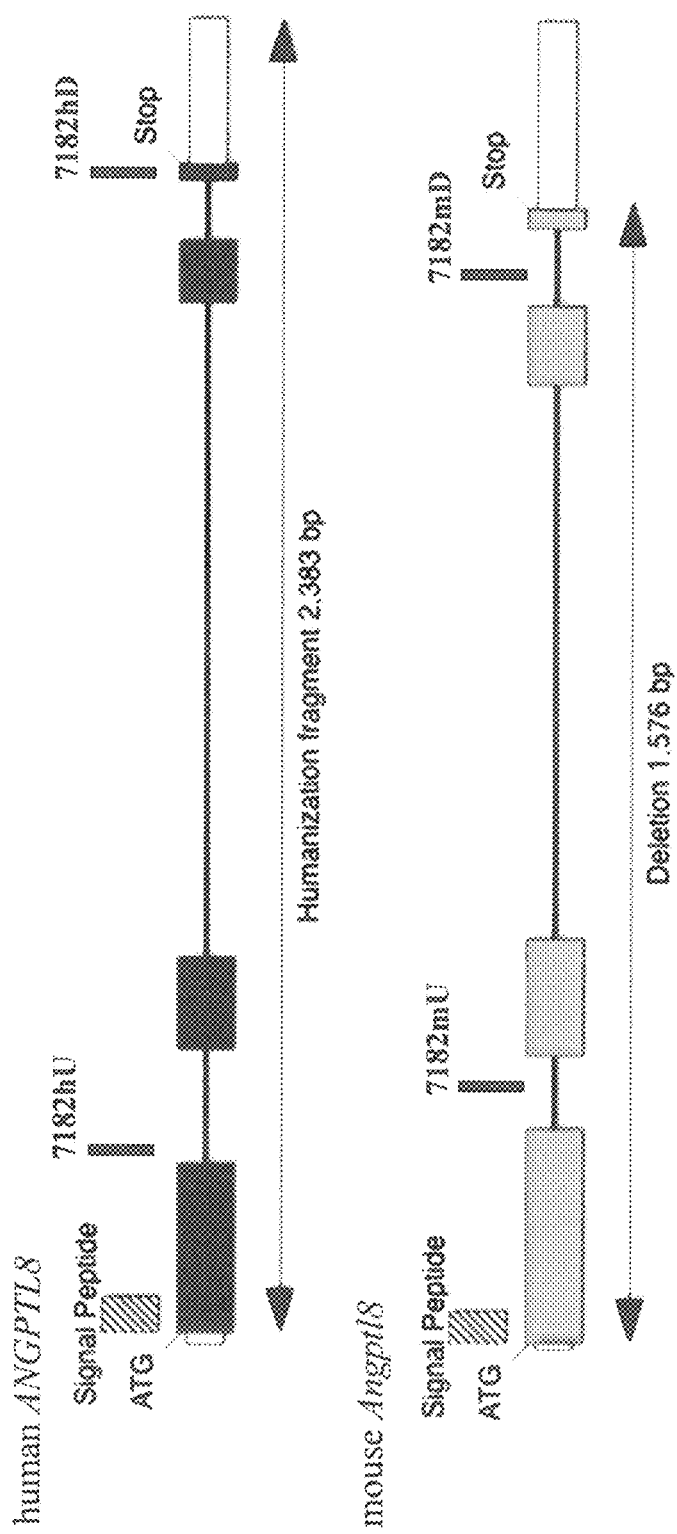
FIG. 4 shows a representative diagram, not to scale, of the genomic organization of mouse and human Angiopoietin-like protein 8 (ANGPTL8) genes indicating the approximate locations of probes employed in an assay described in Example 1. Lengths of an exemplary synthetic DNA fragment employed in humanization of an endogenous murine Angptl8 gene and corresponding deletion are indicated below each respective gene and are described in Example 1.

Positive ES cell clones were then used to implant female mice using the VELOCIMOUSE® method (see, e.g., U.S. Pat. No. 7,294,754 and Poueymirou et al., 2007, Nature Biotech. 25(1):91-99) to generate a litter of pups containing an insertion of human ANGPTL8 exons 1-4 (including human ANGPTL8 3' UTR) into an endogenous Angptl8 locus of a mouse. Mice bearing the human ANGPTL8 exons 1-4 (i.e., the 2,383 bp synthetic DNA fragment) in place of endogenous Angptl8 exons 1-4 were again confirmed and identified by genotyping of DNA isolated from tail snips using an assay as previously described (Valenzuela et al., supra) that detected the presence of the human ANGPTL8 sequences (FIG. 4). Pups are genotyped and cohorts of animals heterozygous for the human ANGPTL8 sequences are selected for characterization.

TABLE 1

| Name | Primer | Sequence (5'-3') |
| --- | --- | --- |
| 7182mU | Forward | GGTGTTGGTGGCAGGTAAGAGT (SEQ ID NO: 19) |
| | Probe | TGAGGAAATGGTAAACCCAGAACAGA (SEQ ID NO: 20) |
| | Reverse | TGGTGTGTCATCAGGGTATGTTTC (SEQ ID NO: 21) |
| 7182mD | Forward | TGAGCCTGGTGGGATTACTCT (SEQ ID NO: 22) |
| | Probe | TAGCAGTGGAAGTTGCCTAGGTCC (SEQ ID NO: 23) |
| | Reverse | CCGTCAAGGCCAGTGCTT (SEQ ID NO: 24) |
| 7182hU | Forward | GCAAGCCTGTTGGAGACTCAG (SEQ ID NO: 25) |
| | Probe | CACCGTAGCTGCGACACTGTGG (SEQ ID NO: 26) |
| | Reverse | AGACACGAACTCCTCTTTGGA (SEQ ID NO: 27) |
| 7182hD | Forward | TGGGCTGAGCCACATCTC (SEQ ID NO: 28) |
| | Probe | CAGACTCCACACAGCGGCGCT (SEQ ID NO: 29) |
| | Reverse | TCAGTTCCATCCAGGCAGATTC (SEQ ID NO: 30) |

Example 2. Expression of Human ANGPTL8 in Non-Human Animals

This Example demonstrates that non-human animals (e.g., rodents) containing an engineered Angptl8 gene according to Example 1 express (or secrete) human (or humanized) ANGPTL8 polypeptide that is detectable in the plasma of the non-human animal. In particular, as described below, non-human animals having an engineered Angptl8 gene demonstrate augmented triglyceride levels as compared to wild-type non-human animals (e.g., wild-type rodents) that contain a wild-type Angptl8 gene.

Briefly, venous Hood was collected at non-fasted conditions from wild-type (n=9) and mice homozygous for an engineered Angptl8 gene (n=8) in EDTA tubes from the retroorbital plexus. Plasma was isolated by centrifugation of collected blood at 4,000 rpm for 10 minutes. Plasma was analyzed for expression of human ANGPTL8 by an ELISA assay using an anti-ANGPLT8 antibody.

The data demonstrated that human ANGPTL8 was secreted into the plasma of mice homozygous for a humanized Angptl8 gene. In particular, protein expression of human ANGPTL8 averaged about 400 ng/mL for all humanized mice from which blood was collected. Thus, rodents containing an engineered Angptl8 gene according to Example 1 detectably express (and secrete) human ANGPTL8 in the plasma. In particular, such expression (or secretion) of human ANGPTL8 is under the control of rodent Angptl8 regulatory elements (e.g., a rodent Angptl8 promoter) in these animals.

In another experiment, plasma from wild-type and mice homozygous for an engineered Angptl8 gene (as described above) collected at non-fasted conditions was also used to determine plasma lipid levels.

Briefly, plasma lipids (triglycerides, total cholesterol, low-density lipoprotein cholesterol [LDL-C], high-density lipoprotein cholesterol [HDL-C]) were measured using serum chemistry analyzer ADVIA® 1800 (Siemens) according to manufacturer's specifications. Representative results are set forth in FIG. 5.

Figure 5:
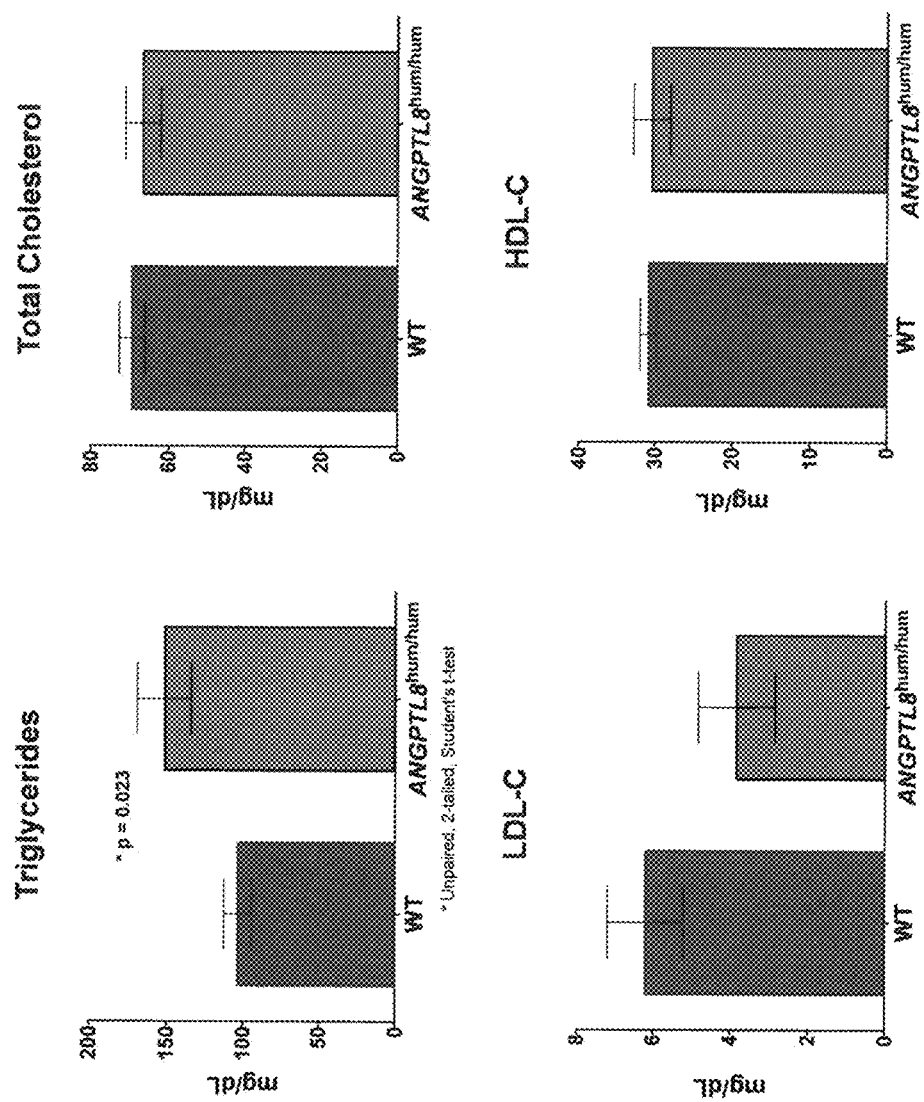
FIG. 5 shows representative levels of triglycerides, total cholesterol, low-density lipoprotein cholesterol (LDL-C) and high-density lipoprotein cholesterol (HLD-C) in wild-type (WT) and mice homozygous for a humanized Angptl8 gene (ANGPTL8$^{hum/hum}$) as described in Example 2. Lipid levels are presented as mg/dL in plasma separated from venous blood.

As shown in FIG. 5, rodents having an engineered Angptl8 gene as described herein demonstrate augmented triglyceride levels as compared to wild-type rodents.

Example 3. Tissue Expression of Human ANGPTL8 in Non-Human Animals

This Example demonstrates that non-human animals (e.g., rodents) containing an engineered Angptl8 gene according to Example 1 express (or secrete) human (or humanized) ANGPTL8 polypeptide that is detectable in various tissues of the non-human animal. In particular, as described below, non-human animals having an engineered Angptl8 gene demonstrate expression of human ANGPTL8 in liver and adipose tissues.

Briefly, RNA preparation and RNAseq read mapping was performed as previously described (Mastaitis, J. et al., 2015, Proc. Natl. Acad. Sci. U.S.A. 112(6):1845-9) using tissues from mice homozygous for an engineered Angptl8 gene, as described in Example 1, collected at re-fed conditions. Representative results are set forth in FIG. 6.

Figure 6:
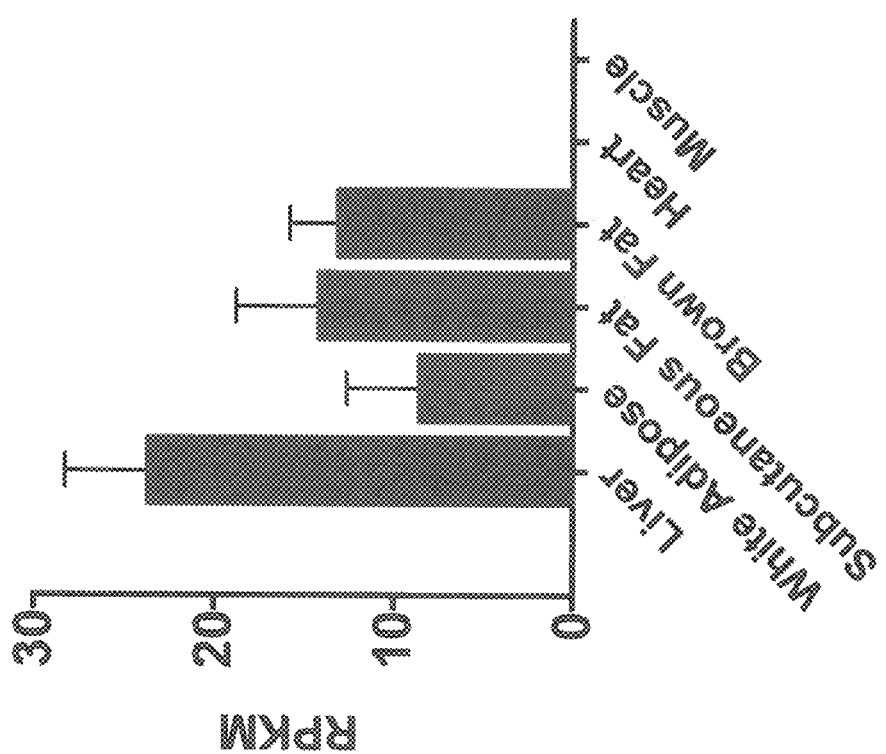
FIG. 6 shows representative tissue-specific (liver and adipose tissues) expression of human ANGPTL8 in mice homozygous for a humanized Angptl8 gene as described in Example 3. The expression levels are shown as reads per kilo base of transcript per million mapped reads (RPKM)

As shown in FIG. 6, human ANGPTL8 expression was identified in liver and adipose tissues (e.g., white adipose, subcutaneous and brown fat) of humanized Anptl8 mice. This Example demonstrates that the engineering of a murine Angptl8 gene as described herein results in expression of a human ANGPTL8 polypeptide in a tissue-specific manner and, therefore, provide an in vivo animal model for determining the efficacy of anti-ANGPTL8 therapeutics to lower triglyceride levels in vivo.

Example 4. In Vivo Efficacy of ANGPTL8 Modulators

This Example demonstrates that non-human animals (e.g., rodents) modified to contain a humanized Angptl8 gene according to Example 1 can be used in an in vivo assay to screen Angptl8 modulators (e.g., anti-ANGPTL8 antibodies) for their triglyceride-lowering efficacy. In this Example, representative anti-ANGPTL8 antibodies are screened in mice homozygous for a humanized Angptl8 gene to determine the efficacy of monoclonal antibody therapy to lower elevated triglycerides.

Briefly, mice homozygous for an engineered Angptl8 gene (as described above) were pre-bled 5 days before the experiment and sorted into treatment groups (n=5 per treatment group) based on their triglyceride levels so that the mean triglyceride level across each group was equal. Anti-ANGPTL8 antibodies or control (isotype-matched human IgG4 control with irrelevant specificity) were administered at 10 mg/kg dose by subcutaneous injection on Day 0 of the study. Mice were bled at 4 days after injection and serum triglyceride levels were determined by ADVIA® 1800 Serum Chemistry Analyzer (Siemens). Results were expressed as Mean±SEM for each group for all tested antibodies. Representative results are set forth in FIG. 7.

Figure 7:
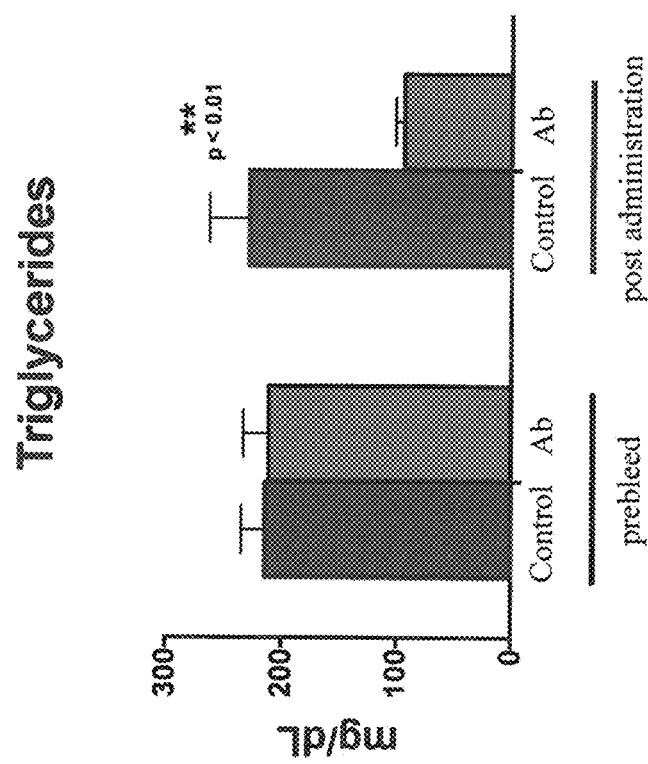
FIG. 7 shows representative serum triglyceride levels in mice homozygous for a humanized Angptl8 gene as described in Example 4 before and after administration of the anti-ANGPTL8 antibody or control (isotype-matched human IgG with irrelevant specificity). Serum triglyceride levels are presented as mg/dL prior (prebleed) and after (post administration) treatment with antibody.

As shown in FIG. 7, anti-ANGPTL8 antibody therapy significantly reduced circulating triglyceride levels as compared to control antibody. Further, these data suggest that mice containing an engineered Angptl8 gene as described in Example 1 express human ANGPTL8 and can be used in screening therapeutics for the treatment of elevated triglyceride levels. Taken together, the present disclosure demonstrates that non-human animals provided herein offer an in viva system for assessing the triglyceride-lowering efficacy of anti-ANGPTL8 antibodies and, in some embodiments, provide an in vivo animal model for hypertriglyceridemia.

EQUIVALENTS

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such dements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein. The publications, websites and other reference materials referenced herein to describe the background of the invention and to provide additional detail regarding its practice are hereby incorporated by reference.

The invention claimed is:

1. A mouse whose genome comprises an engineered Angptl8 gene at an endogenous mouse Angptl8 locus,
wherein the engineered Angptl8 gene comprises the 5' untranslated portion of exon 1 of the endogenous mouse Angptl8 gene, the coding portion of exon 1 of a human ANGPTL8 gene, and exons 2-4 of the human ANGPTL8 gene,
wherein the engineered Angptl8 gene encodes a human ANGPTL8 protein and is operably linked to the endogenous mouse Angptl8 promoter,
wherein the human ANGPTL8 protein is expressed in the mouse from the engineered Angptl8 gene, and
wherein the mouse has an increased triglyceride level when compared to a wild type mouse.

2. The mouse of claim 1, wherein the engineered Angptl8 gene comprises the 3' untranslated regions (UTRs) of the endogenous mouse Angptl8 gene.

3. The mouse of claim 1, wherein the human ANGPTL8 protein comprises the amino acid sequence as set forth in SEQ ID NO: 6.

4. The mouse of claim 1, wherein the human ANGPTL8 protein comprises amino acid residues 22-198 of SEQ ID NO: 6.

5. An isolated mouse cell or tissue, wherein the genome of the cell or tissue comprises an engineered Angptl8 gene at an endogenous mouse Angptl8 locus,
wherein the engineered Angptl8 gene comprises the 5' untranslated portion of exon 1 of the endogenous mouse Angptl8 gene, the coding portion of exon 1 of a human ANGPTL8 gene, and exons 2-4 of the human ANGPTL8 gene, and
wherein the engineered Angptl8 gene encodes a human ANGPTL8 protein and is operably linked to the endogenous mouse Angptl8 promoter.

6. The isolated mouse cell or tissue of claim 5, wherein the isolated mouse cell is a mouse embryonic stem cell.

7. A mouse embryo comprising the mouse embryonic stem cell of claim 6.

8. A method of making a mouse whose genome comprises an engineered Angptl8 gene that encodes a human ANGPTL8 polypeptide, wherein the mouse has an increased triglyceride level when compared to a wild type mouse, the method comprising:
modifying the genome of a mouse cell in vitro so that the modified genome comprises an engineered Angptl8 gene at a mouse endogenous Angptl8locus,
wherein the engineered Angptl8 gene comprises the 5' untranslated portion of exon 1 of the endogenous mouse Angptl8 gene, the coding portion of exon 1 of a human ANGPTL8 gene, and exons 2-4 of the human ANGPTL8 gene, and
wherein the engineered Angptl8 gene encodes a human ANGPTL8 polypeptide and is operably linked to the endogenous mouse Angptl8 promoter, and
producing a mouse from said mouse cell, wherein the genome of the mouse comprises the engineered Angptl8 gene that encodes the human ANGPTL8 polypeptide, wherein the human ANGPTL8 polypeptide is expressed in the mouse from the engineered Angptl8gene, and
wherein the mouse has an increased triglyceride level when compared to a wild type mouse.

9. The method of claim 8, wherein the method comprises
(a) inserting a nucleic acid encoding the human ANGPTL8 polypeptide into an endogenous Angptl8 locus in a mouse embryonic stem cell, thereby forming the engineered Angptl8 gene at the endogenous Angptl8 locus;
(b) obtaining a mouse embryonic stem cell comprising the engineered Angptl8 gene from (a); and,
(c) creating a mouse using the mouse embryonic stem cell of (b).

10. The method of claim 9, the method further comprises a step of breeding the mouse generated in (c) so that a mouse homozygous for the engineered Angptl8 gene is created.

11. The method of claim 8, wherein the human ANGPTL8 polypeptide comprises amino acid residues 22-198 of SEQ ID NO:6.

12. A method of assessing triglyceride-lowering efficacy of a drug that targets human ANGPTL8, the method comprising the steps of
a) administering the drug to the mouse of claim 1; and
b) performing an assay to determine if the drug that targets human ANGPTL8 lowers triglyceride levels in said mouse.

13. The method of claim 12, wherein the drug targeting human ANGPTL8 is an ANGPTL8 antagonist.

14. The method of claim 12, wherein the drug targeting human ANGPTL8 is an ANGPTL8 agonist.

15. The method of claim 12, wherein the drug targeting human ANGPTL8 is an anti-ANGPTL8 antibody.

16. The method of claim 12, wherein the drug targeting human ANGPTL8 is administered to the rodent intravenously, intraperitoneally, or subcutaneously.

* * * * *